(12) United States Patent
Reed

(10) Patent No.: US 8,153,598 B2
(45) Date of Patent: Apr. 10, 2012

(54) PKD LIGANDS AND POLYNUCLEOTIDES ENCODING PKD LIGANDS

(75) Inventor: Thomas D. Reed, Blacksburg, VA (US)

(73) Assignee: Intrexon Corporation, Blacksburg, VA (US)

( * ) Notice: Subject to any disclaimer, the term of this patent is extended or adjusted under 35 U.S.C. 154(b) by 785 days.

(21) Appl. No.: 12/090,462

(22) PCT Filed: Oct. 18, 2006

(86) PCT No.: PCT/US2006/060062
§ 371 (c)(1),
(2), (4) Date: Dec. 15, 2008

(87) PCT Pub. No.: WO2007/048103
PCT Pub. Date: Apr. 26, 2007

(65) Prior Publication Data
US 2009/0215173 A1    Aug. 27, 2009

Related U.S. Application Data

(60) Provisional application No. 60/728,259, filed on Oct. 19, 2005.

(51) Int. Cl.
*A61K 38/16* (2006.01)
*C12P 19/34* (2006.01)
*C12N 15/64* (2006.01)

(52) U.S. Cl. ...... 514/21.3; 530/324; 435/91.1; 435/91.4

(58) Field of Classification Search .......... None
See application file for complete search history.

(56) References Cited

U.S. PATENT DOCUMENTS

| | | |
|---|---|---|
| 7,071,295 B2 | 7/2006 | Reed |
| 2004/0185556 A1 | 9/2004 | Reed |
| 2008/0032947 A1 | 2/2008 | Reed |
| 2008/0050808 A1 | 2/2008 | Reed et al. |
| 2008/0051360 A1 | 2/2008 | Reed et al. |
| 2008/0213834 A1 | 9/2008 | Reed et al. |
| 2008/0220475 A1 | 9/2008 | Reed et al. |
| 2009/0186379 A1 | 7/2009 | Reed |
| 2009/0215173 A1 | 8/2009 | Reed |
| 2009/0215866 A1 | 8/2009 | Reed |

FOREIGN PATENT DOCUMENTS

| | | |
|---|---|---|
| WO | WO 2005/040336 A2 | 5/2005 |
| WO | WO 2005/116231 A1 | 12/2005 |
| WO | WO 2007/048103 A2 | 4/2007 |
| WO | WO 2007/076166 A2 | 7/2007 |
| WO | WO 2008/119058 A2 | 10/2008 |

OTHER PUBLICATIONS

Ji, Y., et al., "Targeted Inhibition of $Ca^{2+}$/Calmodulin-dependant Protein Kinase II in Cardiac Longitudinal Sarcoplasmic Reticulum Results in Decreased Phospholamban Phosphorylation at Threonine 17," *J. Biol. Chem.* 278:25063-25071, The American Society for Biochemistry and Molecular Biology, Inc. (2003).

U.S. Appl. No. 11/983,235, inventor Reed, Thomas D., filed Nov. 8, 2007.

U.S. Appl. No. 12/532,912, inventors Bachinsky et al., U.S. national phase of International Application No. PCT/US08/058531, filed Mar. 27, 2008.

*Primary Examiner* — Cecilia J Tsang
*Assistant Examiner* — Satyanarayana R Gudibande
(74) *Attorney, Agent, or Firm* — Sterne, Kessler, Goldstein & Fox P.L.L.C.

(57) ABSTRACT

The invention relates to kinase ligands and polyligands. In particular, the invention relates to ligands, homopolyligands, and heteropolyligands that modulate protein kinase D (PKD) activity. The ligands and polyligands are utilized as research tools or as therapeutics. The invention includes linkage of the ligands and polyligands to cellular localization signals, epitope tags and/or reporters. The invention also includes polynucleotides encoding the ligands and polyligands.

19 Claims, 10 Drawing Sheets

| LIGAND X | LIGAND X |

FIGURE 1A

| LIGAND X | LIGAND X | LIGAND X |

FIGURE 1B

| LIGAND X | LIGAND X | LIGAND X | LIGAND X | LIGAND X |

FIGURE 1C

| LIGAND X | SPACER | LIGAND X |

FIGURE 2A

| LIGAND X | SPACER | LIGAND X | SPACER | LIGAND X |

FIGURE 2B

| LIGAND X | LIGAND X | SPACER | LIGAND X | SPACER | LIGAND X |

FIGURE 2C

| LIGAND X | LIGAND Y |

FIGURE 3A

| LIGAND X | LIGAND Y | LIGAND Z |

FIGURE 3B

| LIGAND X | LIGAND Y | LIGAND X | LIGAND Z | LIGAND Z |

FIGURE 3C

| LIGAND B | SPACER | LIGAND A |

FIGURE 4A

| LIGAND X | SPACER | LIGAND Y | SPACER | LIGAND Z |

FIGURE 4B

| LIGAND X | LIGAND Y | SPACER | LIGAND Y | LIGAND X |

FIGURE 4C

| LIGAND X | LIGAND X | EPITOPE |

FIGURE 5A

| EPITOPE | LIGAND X | LIGAND Y |

FIGURE 5B

| LIGAND X | SPACER | LIGAND X | EPITOPE |

FIGURE 5C

| EPITOPE | LIGAND X | SPACER | LIGAND Y |

FIGURE 5D

| LIGAND X | SPACER | LIGAND Y | SPACER | LIGAND B | EPITOPE |

FIGURE 5E

| EPITOPE | LIGAND X | SPACER | LIGAND Y | LIGAND B |

FIGURE 5F

| LIGAND X | EPITOPE |

FIGURE 5G

| LIGAND X | LIGAND X | REPORTER |

FIGURE 6A

| REPORTER | LIGAND X | LIGAND Y |

FIGURE 6B

| LIGAND X | SPACER | LIGAND X | REPORTER |

FIGURE 6C

| REPORTER | LIGAND X | SPACER | LIGAND Y |

FIGURE 6D

| LIGAND X | SPACER | LIGAND Y | SPACER | LIGAND B | REPORTER |

FIGURE 6E

| REPORTER | LIGAND X | SPACER | LIGAND Y | LIGAND B |

FIGURE 6F

| LIGAND X | REPORTER |

FIGURE 6G

| LIGAND X | LIGAND X | LOCALIZATION SIGNAL |

FIGURE 7A

| LOCALIZATION SIGNAL | LIGAND X | LIGAND Y |

FIGURE 7B

| LIGAND X | SPACER | LIGAND X | LOCALIZATION SIGNAL |

FIGURE 7C

| LOCALIZATION SIGNAL | LIGAND X | SPACER | LIGAND Y |

FIGURE 7D

| LIGAND X | SPACER | LIGAND Y | LIGAND B | LOCALIZATION SIGNAL |

FIGURE 7E

| LOCALIZATION SIGNAL | LIGAND X | SPACER | LIGAND Y | SPACER | LIGAND B |

FIGURE 7F

| LOCALIZATION SIGNAL | LIGAND Y |

FIGURE 7G

| EPITOPE | LIGAND X | LIGAND X | LOCALIZATION SIGNAL |

FIGURE 8A

| LOCALIZATION SIGNAL | LIGAND X | LIGAND Y | EPITOPE |

FIGURE 8B

| EPITOPE | LIGAND X | SPACER | LIGAND X | LOCALIZATION SIGNAL |

FIGURE 8C

| LOCALIZATION SIGNAL | LIGAND X | SPACER | LIGAND Y | EPITOPE |

FIGURE 8D

| EPITOPE | LIGAND X | LIGAND Y | LIGAND B | LOCALIZATION SIGNAL |

FIGURE 8E

| LOCALIZATION SIGNAL | LIGAND Z | SPACER | LIGAND Y | LIGAND B | EPITOPE |

FIGURE 8F

| EPITOPE | LIGAND B | LOCALIZATION SIGNAL |

FIGURE 8G

| PROMOTER | OPTIONAL EPITOPE | OPTIONAL REPORTER | LIGAND, HOMOPOLYLIGAND, or HETEROPOLYLIGAND | OPTIONAL LOCALIZATION SIGNAL | STOP | POLY-A |

FIGURE 9A

| PROMOTER | OPTIONAL REPORTER | OPTIONAL EPITOPE | LIGAND, HOMOPOLYLIGAND, or HETEROPOLYLIGAND | OPTIONAL LOCALIZATION SIGNAL | STOP | POLY-A |

FIGURE 9B

| PROMOTER | LIGAND, HOMOPOLYLIGAND, or HETEROPOLYLIGAND | OPTIONAL REPORTER | OPTIONAL EPITOPE | OPTIONAL LOCALIZATION SIGNAL | STOP | POLY-A |

FIGURE 9C

| PROMOTER | LIGAND, HOMOPOLYLIGAND, or HETEROPOLYLIGAND | OPTIONAL EPITOPE | OPTIONAL REPORTER | OPTIONAL LOCALIZATION SIGNAL | STOP | POLY-A |

FIGURE 9D

| PROMOTER | LIGAND, HOMOPOLYLIGAND, or HETEROPOLYLIGAND | LOCALIZATION SIGNAL | STOP | POLY-A |

FIGURE 9E

| PROMOTER | LOCALIZATION SIGNAL | LIGAND, HOMOPOLYLIGAND, or HETEROPOLYLIGAND | STOP | POLY-A |

FIGURE 9F

| PROMOTER | LIGAND, HOMOPOLYLIGAND, or HETEROPOLYLIGAND | STOP | POLY-A |

FIGURE 9G

SEQUENCE LISTING

```
<160> NUMBER OF SEQ ID NOS: 132

<210> SEQ ID NO 1
<211> LENGTH: 9
<212> TYPE: PRT
<213> ORGANISM: artificial
<220> FEATURE:
<223> OTHER INFORMATION: synthetic

<400> SEQUENCE: 1

Leu Ala Arg Arg Leu Ser Phe Ile Gly
1               5

<210> SEQ ID NO 2
<211> LENGTH: 28
<212> TYPE: PRT
<213> ORGANISM: artificial
<220> FEATURE:
<223> OTHER INFORMATION: synthetic

<400> SEQUENCE: 2

Asp Phe Gly Ile Ser Ala Gln Ile Gly Ala Thr Leu Ala Arg Arg Leu
1               5                   10                  15

Ser Phe Ile Gly Thr Pro Tyr Trp Met Ala Pro Glu
            20                  25

<210> SEQ ID NO 3
<211> LENGTH: 8
<212> TYPE: PRT
<213> ORGANISM: artificial
<220> FEATURE:
<223> OTHER INFORMATION: synthetic

<400> SEQUENCE: 3

Leu Val Arg Gln Met Ser Val Ala
1               5

<210> SEQ ID NO 4
```

```
<211> LENGTH: 14
<212> TYPE: PRT
<213> ORGANISM: artificial
<220> FEATURE:
<223> OTHER INFORMATION: synthetic

<400> SEQUENCE: 4

Ala Ala Leu Val Arg Gln Met Ser Val Ala Phe Phe Phe Lys
1               5                   10

<210> SEQ ID NO 5
<211> LENGTH: 9
<212> TYPE: PRT
<213> ORGANISM: artificial
<220> FEATURE:
<223> OTHER INFORMATION: synthetic

<400> SEQUENCE: 5

Leu Ser Arg Gln Leu Ser Ser Gly Val
1               5

<210> SEQ ID NO 6
<211> LENGTH: 22
<212> TYPE: PRT
<213> ORGANISM: artificial
<220> FEATURE:
<223> OTHER INFORMATION: synthetic

<400> SEQUENCE: 6

Ala Tyr Ser Arg Ala Leu Ser Arg Gln Leu Ser Ser Gly Val Ser Glu
1               5                   10                  15

Ile Arg His Thr Ala Asp
            20

<210> SEQ ID NO 7
<211> LENGTH: 42
<212> TYPE: PRT
<213> ORGANISM: artificial
<220> FEATURE:
<223> OTHER INFORMATION: synthetic

<400> SEQUENCE: 7

Ala Ile Glu Ser Pro Ala Val Ala Ala Pro Ala Tyr Ser Arg Ala Leu
1               5                   10                  15

Ser Arg Gln Leu Ser Ser Gly Val Ser Glu Ile Arg His Thr Ala Asp
            20                  25                  30

Arg Trp Arg Val Ser Leu Asp Val Asn His
        35                  40

<210> SEQ ID NO 8
<211> LENGTH: 62
<212> TYPE: PRT
<213> ORGANISM: artificial
<220> FEATURE:
<223> OTHER INFORMATION: synthetic

<400> SEQUENCE: 8

Pro Gly Tyr Val Arg Pro Leu Pro Ala Ala Ile Glu Ser Pro Ala
1               5                   10                  15

Val Ala Ala Pro Ala Tyr Ser Arg Ala Leu Ser Arg Gln Leu Ser Ser
            20                  25                  30

Gly Val Ser Glu Ile Arg His Thr Ala Asp Arg Trp Arg Val Ser Leu
        35                  40                  45

Asp Val Asn His Phe Ala Pro Asp Glu Arg Thr Val Lys Thr
    50                  55                  60
```

```
<210> SEQ ID NO 9
<211> LENGTH: 10
<212> TYPE: PRT
<213> ORGANISM: artificial
<220> FEATURE:
<223> OTHER INFORMATION: synthetic

<400> SEQUENCE: 9

Leu Lys Arg Thr Ala Ser Asn Pro Lys Val
1               5                   10

<210> SEQ ID NO 10
<211> LENGTH: 21
<212> TYPE: PRT
<213> ORGANISM: artificial
<220> FEATURE:
<223> OTHER INFORMATION: synthetic

<400> SEQUENCE: 10

Ser Leu Ser Ser Asn Leu Lys Arg Thr Ala Ser Asn Pro Lys Val Glu
1               5                   10                  15

Asn Glu Asp Glu Pro
            20

<210> SEQ ID NO 11
<211> LENGTH: 41
<212> TYPE: PRT
<213> ORGANISM: artificial
<220> FEATURE:
<223> OTHER INFORMATION: synthetic

<400> SEQUENCE: 11

Arg Ser Lys Ser Asp Ala Thr Ala Ser Ile Ser Leu Ser Ser Asn Leu
1               5                   10                  15

Lys Arg Thr Ala Ser Asn Pro Lys Val Glu Asn Glu Asp Glu Pro Val
            20                  25                  30

Arg Leu Ala Pro Glu Arg Glu Phe Ile
        35                  40

<210> SEQ ID NO 12
<211> LENGTH: 61
<212> TYPE: PRT
<213> ORGANISM: artificial
<220> FEATURE:
<223> OTHER INFORMATION: synthetic

<400> SEQUENCE: 12

Gly Leu Ser Pro Ser Lys Arg Thr His Gln Arg Ser Lys Ser Asp Ala
1               5                   10                  15

Thr Ala Ser Ile Ser Leu Ser Ser Asn Leu Lys Arg Thr Ala Ser Asn
            20                  25                  30

Pro Lys Val Glu Asn Glu Asp Glu Pro Val Arg Leu Ala Pro Glu Arg
        35                  40                  45

Glu Phe Ile Lys Ser Leu Met Ala Ile Gly Lys Arg Leu
    50                  55                  60

<210> SEQ ID NO 13
<211> LENGTH: 9
<212> TYPE: PRT
<213> ORGANISM: artificial
<220> FEATURE:
<223> OTHER INFORMATION: synthetic

<400> SEQUENCE: 13
```

```
Leu Arg Lys Thr Val Ser Glu Pro Asn
1               5

<210> SEQ ID NO 14
<211> LENGTH: 8
<212> TYPE: PRT
<213> ORGANISM: artificial
<220> FEATURE:
<223> OTHER INFORMATION: synthetic

<400> SEQUENCE: 14

Leu Leu Arg Lys Glu Ser Ala Pro
1               5

<210> SEQ ID NO 15
<211> LENGTH: 9
<212> TYPE: PRT
<213> ORGANISM: artificial
<220> FEATURE:
<223> OTHER INFORMATION: synthetic

<400> SEQUENCE: 15

Leu Ser Arg Ala Gln Ser Ser Pro Ala
1               5

<210> SEQ ID NO 16
<211> LENGTH: 9
<212> TYPE: PRT
<213> ORGANISM: artificial
<220> FEATURE:
<223> OTHER INFORMATION: synthetic

<400> SEQUENCE: 16

Leu Ser Arg Thr Arg Ser Glu Pro Leu
1               5

<210> SEQ ID NO 17
<211> LENGTH: 21
<212> TYPE: PRT
<213> ORGANISM: artificial
<220> FEATURE:
<223> OTHER INFORMATION: synthetic

<400> SEQUENCE: 17

Pro Glu His Phe Pro Leu Arg Lys Thr Val Ser Glu Pro Asn Leu Lys
1               5                   10                  15

Leu Arg Tyr Lys Pro
            20

<210> SEQ ID NO 18
<211> LENGTH: 41
<212> TYPE: PRT
<213> ORGANISM: artificial
<220> FEATURE:
<223> OTHER INFORMATION: synthetic

<400> SEQUENCE: 18

Pro Pro Val Pro Ser Leu Pro Ser Asp Pro Glu His Phe Pro Leu
1               5                   10                  15

Arg Lys Thr Val Ser Glu Pro Asn Leu Lys Leu Arg Tyr Lys Pro Lys
            20                  25                  30

Lys Ser Leu Glu Arg Arg Lys Asn Pro
        35                  40

<210> SEQ ID NO 19
```

<211> LENGTH: 87
<212> TYPE: PRT
<213> ORGANISM: artificial
<220> FEATURE:
<223> OTHER INFORMATION: synthetic

<400> SEQUENCE: 19

Ala Thr Arg Ser Met Leu Ser Ser Phe Leu Pro Pro Val Pro Ser Leu
1               5                   10                  15

Pro Ser Asp Pro Pro Glu His Phe Pro Leu Arg Lys Thr Val Ser Glu
            20                  25                  30

Pro Asn Leu Lys Leu Arg Tyr Lys Pro Lys Lys Ser Leu Glu Arg Arg
        35                  40                  45

Lys Asn Pro Leu Leu Arg Lys Glu Ser Ala Pro Pro Ser Leu Arg Arg
    50                  55                  60

Arg Pro Ala Glu Thr Leu Gly Asp Ser Ser Pro Ser Ser Ser Ser Thr
65                  70                  75                  80

Pro Ala Ser Gly Cys Ser Ser
                85

<210> SEQ ID NO 20
<211> LENGTH: 21
<212> TYPE: PRT
<213> ORGANISM: artificial
<220> FEATURE:
<223> OTHER INFORMATION: synthetic

<400> SEQUENCE: 20

Arg Arg Lys Asn Pro Leu Leu Arg Lys Glu Ser Ala Pro Pro Ser Leu
1               5                   10                  15

Arg Arg Arg Pro Ala
            20

<210> SEQ ID NO 21
<211> LENGTH: 41
<212> TYPE: PRT
<213> ORGANISM: artificial
<220> FEATURE:
<223> OTHER INFORMATION: synthetic

<400> SEQUENCE: 21

Leu Arg Tyr Lys Pro Lys Lys Ser Leu Glu Arg Arg Lys Asn Pro Leu
1               5                   10                  15

Leu Arg Lys Glu Ser Ala Pro Pro Ser Leu Arg Arg Arg Pro Ala Glu
            20                  25                  30

Thr Leu Gly Asp Ser Ser Pro Ser Ser
        35                  40

<210> SEQ ID NO 22
<211> LENGTH: 21
<212> TYPE: PRT
<213> ORGANISM: artificial
<220> FEATURE:
<223> OTHER INFORMATION: synthetic

<400> SEQUENCE: 22

Gly Leu His Trp Pro Leu Ser Arg Thr Arg Ser Glu Pro Leu Pro Pro
1               5                   10                  15

Ser Ala Thr Ala Pro
            20

<210> SEQ ID NO 23
<211> LENGTH: 41

```
<212> TYPE: PRT
<213> ORGANISM: artificial
<220> FEATURE:
<223> OTHER INFORMATION: synthetic

<400> SEQUENCE: 23

Leu Met Thr Thr Glu Arg Leu Ser Gly Ser Gly Leu His Trp Pro Leu
1               5                   10                  15

Ser Arg Thr Arg Ser Glu Pro Leu Pro Pro Ser Ala Thr Ala Pro Pro
            20                  25                  30

Pro Pro Gly Pro Met Gln Pro Arg Leu
        35                  40

<210> SEQ ID NO 24
<211> LENGTH: 61
<212> TYPE: PRT
<213> ORGANISM: artificial
<220> FEATURE:
<223> OTHER INFORMATION: synthetic

<400> SEQUENCE: 24

Gly Pro Leu Pro Phe His Phe Ala Gln Ser Leu Met Thr Thr Glu Arg
1               5                   10                  15

Leu Ser Gly Ser Gly Leu His Trp Pro Leu Ser Arg Thr Arg Ser Glu
            20                  25                  30

Pro Leu Pro Pro Ser Ala Thr Ala Pro Pro Pro Pro Gly Pro Met Gln
        35                  40                  45

Pro Arg Leu Glu Gln Leu Lys Thr His Val Gln Val Ile
    50                  55                  60

<210> SEQ ID NO 25
<211> LENGTH: 21
<212> TYPE: PRT
<213> ORGANISM: artificial
<220> FEATURE:
<223> OTHER INFORMATION: synthetic

<400> SEQUENCE: 25

Gly Gly His Arg Pro Leu Ser Arg Ala Gln Ser Ser Pro Ala Ala Pro
1               5                   10                  15

Ala Ser Leu Ser Ala
            20

<210> SEQ ID NO 26
<211> LENGTH: 41
<212> TYPE: PRT
<213> ORGANISM: artificial
<220> FEATURE:
<223> OTHER INFORMATION: synthetic

<400> SEQUENCE: 26

Gly Asp Thr Val Leu Leu Pro Leu Ala Gln Gly Gly His Arg Pro Leu
1               5                   10                  15

Ser Arg Ala Gln Ser Ser Pro Ala Ala Pro Ala Ser Leu Ser Ala Pro
            20                  25                  30

Glu Pro Ala Ser Gln Ala Arg Val Leu
        35                  40

<210> SEQ ID NO 27
<211> LENGTH: 61
<212> TYPE: PRT
<213> ORGANISM: artificial
<220> FEATURE:
<223> OTHER INFORMATION: synthetic
```

-continued

<400> SEQUENCE: 27

Leu Ala Gly Arg Leu Pro Arg Gly Ser Thr Gly Asp Thr Val Leu Leu
1               5                   10                  15

Pro Leu Ala Gln Gly Gly His Arg Pro Leu Ser Arg Ala Gln Ser Ser
            20                  25                  30

Pro Ala Ala Pro Ala Ser Leu Ser Ala Pro Glu Pro Ala Ser Gln Ala
        35                  40                  45

Arg Val Leu Ser Ser Ser Glu Thr Pro Ala Arg Thr Leu
    50                  55                  60

<210> SEQ ID NO 28
<211> LENGTH: 9
<212> TYPE: PRT
<213> ORGANISM: artificial
<220> FEATURE:
<223> OTHER INFORMATION: synthetic

<400> SEQUENCE: 28

Ile Thr Arg Gln Met Ser Phe Asp Leu
1               5

<210> SEQ ID NO 29
<211> LENGTH: 17
<212> TYPE: PRT
<213> ORGANISM: artificial
<220> FEATURE:
<223> OTHER INFORMATION: synthetic

<400> SEQUENCE: 29

Arg Gln Met Gln Arg Thr Ile Thr Arg Gln Met Ser Phe Asp Leu Thr
1               5                   10                  15

Lys

<210> SEQ ID NO 30
<211> LENGTH: 21
<212> TYPE: PRT
<213> ORGANISM: artificial
<220> FEATURE:
<223> OTHER INFORMATION: synthetic

<400> SEQUENCE: 30

Gln Met Gln Arg Thr Ile Thr Arg Gln Met Ser Phe Asp Leu Thr Lys
1               5                   10                  15

Leu Leu Val Thr Glu
            20

<210> SEQ ID NO 31
<211> LENGTH: 41
<212> TYPE: PRT
<213> ORGANISM: artificial
<220> FEATURE:
<223> OTHER INFORMATION: synthetic

<400> SEQUENCE: 31

Leu Asn Arg Arg Asp Thr Tyr Arg Arg Gln Met Gln Arg Thr Ile
1               5                   10                  15

Thr Arg Gln Met Ser Phe Asp Leu Thr Lys Leu Leu Val Thr Glu Asp
            20                  25                  30

Trp Phe Ser Asp Ile Ser Pro Gln Thr
        35                  40

<210> SEQ ID NO 32

<211> LENGTH: 61
<212> TYPE: PRT
<213> ORGANISM: artificial
<220> FEATURE:
<223> OTHER INFORMATION: synthetic

<400> SEQUENCE: 32

Glu Met Thr Lys Leu Gly Ser Lys Thr Ala Leu Asn Arg Arg Asp Thr
1               5                   10                  15

Tyr Arg Arg Arg Gln Met Gln Arg Thr Ile Thr Arg Gln Met Ser Phe
                20                  25                  30

Asp Leu Thr Lys Leu Leu Val Thr Glu Asp Trp Phe Ser Asp Ile Ser
            35                  40                  45

Pro Gln Thr Met Arg Arg Leu Leu Asn Ile Val Ser Val
    50                  55                  60

<210> SEQ ID NO 33
<211> LENGTH: 10
<212> TYPE: PRT
<213> ORGANISM: artificial
<220> FEATURE:
<223> OTHER INFORMATION: synthetic

<400> SEQUENCE: 33

Arg Lys Asn Ile Asp Ala Leu Ser Gly Met
1               5                   10

<210> SEQ ID NO 34
<211> LENGTH: 10
<212> TYPE: PRT
<213> ORGANISM: artificial
<220> FEATURE:
<223> OTHER INFORMATION: synthetic

<400> SEQUENCE: 34

Ile Arg Arg Arg Ser Ser Asn Tyr Arg Ala
1               5                   10

<210> SEQ ID NO 35
<211> LENGTH: 21
<212> TYPE: PRT
<213> ORGANISM: artificial
<220> FEATURE:
<223> OTHER INFORMATION: synthetic

<400> SEQUENCE: 35

Gly Asp Trp Arg Lys Asn Ile Asp Ala Leu Ser Gly Met Glu Gly Arg
1               5                   10                  15

Lys Lys Lys Phe Glu
            20

<210> SEQ ID NO 36
<211> LENGTH: 32
<212> TYPE: PRT
<213> ORGANISM: artificial
<220> FEATURE:
<223> OTHER INFORMATION: synthetic

<400> SEQUENCE: 36

Glu Asp Thr Glu Lys Glu Asn Arg Glu Val Gly Asp Trp Arg Lys Asn
1               5                   10                  15

Ile Asp Ala Leu Ser Gly Met Glu Gly Arg Lys Lys Lys Phe Glu Ser
            20                  25                  30

<210> SEQ ID NO 37

```
<211> LENGTH: 42
<212> TYPE: PRT
<213> ORGANISM: artificial
<220> FEATURE:
<223> OTHER INFORMATION: synthetic

<400> SEQUENCE: 37

Leu Arg Ala His Leu Lys Gln Val Lys Lys Glu Asp Thr Glu Lys Glu
1               5                   10                  15

Asn Arg Glu Val Gly Asp Trp Arg Lys Asn Ile Asp Ala Leu Ser Gly
            20                  25                  30

Met Glu Gly Arg Lys Lys Lys Phe Glu Ser
        35                  40

<210> SEQ ID NO 38
<211> LENGTH: 20
<212> TYPE: PRT
<213> ORGANISM: artificial
<220> FEATURE:
<223> OTHER INFORMATION: synthetic

<400> SEQUENCE: 38

Ala Pro Ala Pro Ile Arg Arg Arg Ser Ser Asn Tyr Arg Ala Tyr Ala
1               5                   10                  15

Thr Glu Pro His
            20

<210> SEQ ID NO 39
<211> LENGTH: 41
<212> TYPE: PRT
<213> ORGANISM: artificial
<220> FEATURE:
<223> OTHER INFORMATION: synthetic

<400> SEQUENCE: 39

Gly Ser Ser Asp Ala Ala Arg Glu Pro Arg Pro Ala Pro Ala Pro Ile
1               5                   10                  15

Arg Arg Arg Ser Ser Asn Tyr Arg Ala Tyr Ala Thr Glu Pro His Ala
            20                  25                  30

Lys Lys Lys Ser Lys Ile Ser Ala Ser
        35                  40

<210> SEQ ID NO 40
<211> LENGTH: 53
<212> TYPE: PRT
<213> ORGANISM: artificial
<220> FEATURE:
<223> OTHER INFORMATION: synthetic

<400> SEQUENCE: 40

Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr Ala Thr Glu
            20                  25                  30

Pro His Ala Lys Lys Lys Ser Lys Ile Ser Ala Ser Arg Lys Leu Gln
        35                  40                  45

Leu Lys Thr Leu Leu
    50

<210> SEQ ID NO 41
<211> LENGTH: 8
<212> TYPE: PRT
<213> ORGANISM: artificial
<220> FEATURE:
```

<223> OTHER INFORMATION: synthetic

<400> SEQUENCE: 41

Leu Ala Glu Arg Ile Ser Val Leu
1               5

<210> SEQ ID NO 42
<211> LENGTH: 11
<212> TYPE: PRT
<213> ORGANISM: artificial
<220> FEATURE:
<223> OTHER INFORMATION: synthetic

<400> SEQUENCE: 42

Met Gln Gly Leu Ala Glu Arg Ile Ser Val Leu
1               5                   10

<210> SEQ ID NO 43
<211> LENGTH: 21
<212> TYPE: PRT
<213> ORGANISM: artificial
<220> FEATURE:
<223> OTHER INFORMATION: synthetic

<400> SEQUENCE: 43

Gly Gly Ala Cys Pro Pro Gln Asp His Asp Met Gln Gly Leu Ala Glu
1               5                   10                  15

Arg Ile Ser Val Leu
            20

<210> SEQ ID NO 44
<211> LENGTH: 31
<212> TYPE: PRT
<213> ORGANISM: artificial
<220> FEATURE:
<223> OTHER INFORMATION: synthetic

<400> SEQUENCE: 44

Gly Ser Gly Leu Pro Thr Asp Arg Asp Leu Gly Gly Ala Cys Pro Pro
1               5                   10                  15

Gln Asp His Asp Met Gln Gly Leu Ala Glu Arg Ile Ser Val Leu
            20                  25                  30

<210> SEQ ID NO 45
<211> LENGTH: 8
<212> TYPE: PRT
<213> ORGANISM: artificial
<220> FEATURE:
<223> OTHER INFORMATION: synthetic

<400> SEQUENCE: 45

Leu Ala Glu Arg Ile Ser Ile Leu
1               5

<210> SEQ ID NO 46
<211> LENGTH: 11
<212> TYPE: PRT
<213> ORGANISM: artificial
<220> FEATURE:
<223> OTHER INFORMATION: synthetic

<400> SEQUENCE: 46

Met Gln Gly Leu Ala Glu Arg Ile Ser Ile Leu
1               5                   10

<210> SEQ ID NO 47

```
<211> LENGTH: 21
<212> TYPE: PRT
<213> ORGANISM: artificial
<220> FEATURE:
<223> OTHER INFORMATION: synthetic

<400> SEQUENCE: 47

Gly Gly Ala Cys Leu Pro Gln Asp His Glu Met Gln Gly Leu Ala Glu
1               5                   10                  15

Arg Ile Ser Ile Leu
            20

<210> SEQ ID NO 48
<211> LENGTH: 29
<212> TYPE: PRT
<213> ORGANISM: artificial
<220> FEATURE:
<223> OTHER INFORMATION: synthetic

<400> SEQUENCE: 48

Gly Thr Pro Ala Glu Gly Asp Leu Gly Gly Ala Cys Leu Pro Gln Asp
1               5                   10                  15

His Glu Met Gln Gly Leu Ala Glu Arg Ile Ser Ile Leu
            20                  25

<210> SEQ ID NO 49
<211> LENGTH: 10
<212> TYPE: PRT
<213> ORGANISM: artificial
<220> FEATURE:
<223> OTHER INFORMATION: synthetic

<400> SEQUENCE: 49

Leu Leu Arg Ser Met Ser Ala Ala Phe Cys
1               5                   10

<210> SEQ ID NO 50
<211> LENGTH: 22
<212> TYPE: PRT
<213> ORGANISM: artificial
<220> FEATURE:
<223> OTHER INFORMATION: synthetic

<400> SEQUENCE: 50

Leu Gly Arg Arg Arg Pro Leu Leu Arg Ser Met Ser Ala Ala Phe Cys
1               5                   10                  15

Ser Leu Leu Ala Pro Glu
            20

<210> SEQ ID NO 51
<211> LENGTH: 39
<212> TYPE: PRT
<213> ORGANISM: artificial
<220> FEATURE:
<223> OTHER INFORMATION: synthetic

<400> SEQUENCE: 51

Arg Gly Ser Pro Ala Thr Ser Pro His Leu Gly Arg Arg Arg Pro Leu
1               5                   10                  15

Leu Arg Ser Met Ser Ala Ala Phe Cys Ser Leu Leu Ala Pro Glu Arg
            20                  25                  30

Gln Val Gly Arg Ala Ala Ala
        35

<210> SEQ ID NO 52
```

```
<211> LENGTH: 60
<212> TYPE: PRT
<213> ORGANISM: artificial
<220> FEATURE:
<223> OTHER INFORMATION: synthetic

<400> SEQUENCE: 52

Ser Ser Glu Glu Gly Val Pro Gly Ser Arg Gly Ser Pro Ala Thr
1               5                   10                  15

Ser Pro His Leu Gly Arg Arg Pro Leu Leu Arg Ser Met Ser Ala
                20                  25                  30

Ala Phe Cys Ser Leu Leu Ala Pro Glu Arg Gln Val Gly Arg Ala Ala
            35                  40                  45

Ala Ala Leu Met Gln Asp Arg His Thr Ala Ala Gly
        50                  55                  60

<210> SEQ ID NO 53
<211> LENGTH: 28
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (17)..(17)
<223> OTHER INFORMATION: Xaa can be any naturally occurring amino acid

<400> SEQUENCE: 53

Asp Phe Gly Ile Ser Ala Gln Ile Gly Ala Thr Leu Ala Arg Arg Leu
1               5                   10                  15

Xaa Phe Ile Gly Thr Pro Tyr Trp Met Ala Pro Glu
                20                  25

<210> SEQ ID NO 54
<211> LENGTH: 14
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 54

Ala Ala Leu Val Arg Gln Met Xaa Val Ala Phe Phe Phe Lys
1               5                   10

<210> SEQ ID NO 55
<211> LENGTH: 22
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (11)..(12)
<223> OTHER INFORMATION: Xaa can be any naturally occurring amino acid

<400> SEQUENCE: 55

Ala Tyr Ser Arg Ala Leu Ser Arg Gln Leu Xaa Xaa Gly Val Ser Glu
1               5                   10                  15

Ile Arg His Thr Ala Asp
                20

<210> SEQ ID NO 56
<211> LENGTH: 42
```

```
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (21)..(22)
<223> OTHER INFORMATION: Xaa can be any naturally occurring amino acid

<400> SEQUENCE: 56

Ala Ile Glu Ser Pro Ala Val Ala Ala Pro Ala Tyr Ser Arg Ala Leu
1               5                   10                  15

Ser Arg Gln Leu Xaa Xaa Gly Val Ser Glu Ile Arg His Thr Ala Asp
            20                  25                  30

Arg Trp Arg Val Ser Leu Asp Val Asn His
        35                  40

<210> SEQ ID NO 57
<211> LENGTH: 62
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (31)..(32)
<223> OTHER INFORMATION: Xaa can be any naturally occurring amino acid

<400> SEQUENCE: 57

Pro Gly Tyr Val Arg Pro Leu Pro Ala Ala Ile Glu Ser Pro Ala
1               5                   10                  15

Val Ala Ala Pro Ala Tyr Ser Arg Ala Leu Ser Arg Gln Leu Xaa Xaa
            20                  25                  30

Gly Val Ser Glu Ile Arg His Thr Ala Asp Arg Trp Arg Val Ser Leu
        35                  40                  45

Asp Val Asn His Phe Ala Pro Asp Glu Arg Thr Val Lys Thr
    50                  55                  60

<210> SEQ ID NO 58
<211> LENGTH: 21
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 58

Ser Leu Ser Ser Asn Leu Lys Arg Thr Ala Xaa Asn Pro Lys Val Glu
1               5                   10                  15

Asn Glu Asp Glu Pro
            20

<210> SEQ ID NO 59
<211> LENGTH: 41
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 59
```

-continued

```
Arg Ser Lys Ser Asp Ala Thr Ala Ser Ile Ser Leu Ser Ser Asn Leu
1               5                   10                  15

Lys Arg Thr Ala Xaa Asn Pro Lys Val Glu Asn Glu Asp Glu Pro Val
            20                  25                  30

Arg Leu Ala Pro Glu Arg Glu Phe Ile
            35                  40

<210> SEQ ID NO 60
<211> LENGTH: 61
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (31)..(31)
<223> OTHER INFORMATION: Xaa can be any naturally occurring amino acid

<400> SEQUENCE: 60

Gly Leu Ser Pro Ser Lys Arg Thr His Gln Arg Ser Lys Ser Asp Ala
1               5                   10                  15

Thr Ala Ser Ile Ser Leu Ser Ser Asn Leu Lys Arg Thr Ala Xaa Asn
            20                  25                  30

Pro Lys Val Glu Asn Glu Asp Glu Pro Val Arg Leu Ala Pro Glu Arg
            35                  40                  45

Glu Phe Ile Lys Ser Leu Met Ala Ile Gly Lys Arg Leu
            50                  55                  60

<210> SEQ ID NO 61
<211> LENGTH: 21
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 61

Pro Glu His Phe Pro Leu Arg Lys Thr Val Xaa Glu Pro Asn Leu Lys
1               5                   10                  15

Leu Arg Tyr Lys Pro
            20

<210> SEQ ID NO 62
<211> LENGTH: 41
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 62

Pro Pro Val Pro Ser Leu Pro Ser Asp Pro Glu His Phe Pro Leu
1               5                   10                  15

Arg Lys Thr Val Xaa Glu Pro Asn Leu Lys Leu Arg Tyr Lys Pro Lys
            20                  25                  30

Lys Ser Leu Glu Arg Arg Lys Asn Pro
            35                  40

<210> SEQ ID NO 63
```

```
<211> LENGTH: 87
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid

<400> SEQUENCE: 63

Ala Thr Arg Ser Met Leu Ser Ser Phe Leu Pro Pro Val Pro Ser Leu
1               5                   10                  15

Pro Ser Asp Pro Pro Glu His Phe Pro Leu Arg Lys Thr Val Xaa Glu
            20                  25                  30

Pro Asn Leu Lys Leu Arg Tyr Lys Pro Lys Lys Ser Leu Glu Arg Arg
        35                  40                  45

Lys Asn Pro Leu Leu Arg Lys Glu Xaa Ala Pro Pro Ser Leu Arg Arg
    50                  55                  60

Arg Pro Ala Glu Thr Leu Gly Asp Ser Ser Pro Ser Ser Ser Ser Thr
65                  70                  75                  80

Pro Ala Ser Gly Cys Ser Ser
                85

<210> SEQ ID NO 64
<211> LENGTH: 21
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 64

Arg Arg Lys Asn Pro Leu Leu Arg Lys Glu Xaa Ala Pro Pro Ser Leu
1               5                   10                  15

Arg Arg Arg Pro Ala
            20

<210> SEQ ID NO 65
<211> LENGTH: 41
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 65

Leu Arg Tyr Lys Pro Lys Lys Ser Leu Glu Arg Arg Lys Asn Pro Leu
1               5                   10                  15

Leu Arg Lys Glu Xaa Ala Pro Pro Ser Leu Arg Arg Arg Pro Ala Glu
            20                  25                  30

Thr Leu Gly Asp Ser Ser Pro Ser Ser
        35                  40

<210> SEQ ID NO 66
<211> LENGTH: 21
```

```
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 66

Gly Leu His Trp Pro Leu Ser Arg Thr Arg Xaa Glu Pro Leu Pro Pro
1               5                   10                  15

Ser Ala Thr Ala Pro
            20

<210> SEQ ID NO 67
<211> LENGTH: 41
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 67

Leu Met Thr Thr Glu Arg Leu Ser Gly Ser Gly Leu His Trp Pro Leu
1               5                   10                  15

Ser Arg Thr Arg Xaa Glu Pro Leu Pro Pro Ser Ala Thr Ala Pro Pro
            20                  25                  30

Pro Pro Gly Pro Met Gln Pro Arg Leu
        35                  40

<210> SEQ ID NO 68
<211> LENGTH: 61
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (31)..(31)
<223> OTHER INFORMATION: Xaa can be any naturally occurring amino acid

<400> SEQUENCE: 68

Gly Pro Leu Pro Phe His Phe Ala Gln Ser Leu Met Thr Thr Glu Arg
1               5                   10                  15

Leu Ser Gly Ser Gly Leu His Trp Pro Leu Ser Arg Thr Arg Xaa Glu
            20                  25                  30

Pro Leu Pro Pro Ser Ala Thr Ala Pro Pro Pro Gly Pro Met Gln
        35                  40                  45

Pro Arg Leu Glu Gln Leu Lys Thr His Val Gln Val Ile
    50                  55                  60

<210> SEQ ID NO 69
<211> LENGTH: 21
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 69
```

```
Gly Gly His Arg Pro Leu Ser Arg Ala Gln Xaa Ser Pro Ala Ala Pro
1               5                   10                  15

Ala Ser Leu Ser Ala
            20

<210> SEQ ID NO 70
<211> LENGTH: 41
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 70

Gly Asp Thr Val Leu Leu Pro Leu Ala Gln Gly Gly His Arg Pro Leu
1               5                   10                  15

Ser Arg Ala Gln Xaa Ser Pro Ala Ala Pro Ala Ser Leu Ser Ala Pro
            20                  25                  30

Glu Pro Ala Ser Gln Ala Arg Val Leu
        35                  40

<210> SEQ ID NO 71
<211> LENGTH: 61
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (31)..(31)
<223> OTHER INFORMATION: Xaa can be any naturally occurring amino acid

<400> SEQUENCE: 71

Leu Ala Gly Arg Leu Pro Arg Gly Ser Thr Gly Asp Thr Val Leu Leu
1               5                   10                  15

Pro Leu Ala Gln Gly Gly His Arg Pro Leu Ser Arg Ala Gln Xaa Ser
            20                  25                  30

Pro Ala Ala Pro Ala Ser Leu Ser Ala Pro Glu Pro Ala Ser Gln Ala
        35                  40                  45

Arg Val Leu Ser Ser Ser Glu Thr Pro Ala Arg Thr Leu
    50                  55                  60

<210> SEQ ID NO 72
<211> LENGTH: 17
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (12)..(12)
<223> OTHER INFORMATION: Xaa can be any naturally occurring amino acid

<400> SEQUENCE: 72

Arg Gln Met Gln Arg Thr Ile Thr Arg Gln Met Xaa Phe Asp Leu Thr
1               5                   10                  15

Lys

<210> SEQ ID NO 73
<211> LENGTH: 21
<212> TYPE: PRT
<213> ORGANISM: artificial
<220> FEATURE:
```

```
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 73

Gln Met Gln Arg Thr Ile Thr Arg Gln Met Xaa Phe Asp Leu Thr Lys
1               5                   10                  15

Leu Leu Val Thr Glu
            20

<210> SEQ ID NO 74
<211> LENGTH: 41
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 74

Leu Asn Arg Arg Asp Thr Tyr Arg Arg Arg Gln Met Gln Arg Thr Ile
1               5                   10                  15

Thr Arg Gln Met Xaa Phe Asp Leu Thr Lys Leu Leu Val Thr Glu Asp
            20                  25                  30

Trp Phe Ser Asp Ile Ser Pro Gln Thr
        35                  40

<210> SEQ ID NO 75
<211> LENGTH: 61
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (31)..(31)
<223> OTHER INFORMATION: Xaa can be any naturally occurring amino acid

<400> SEQUENCE: 75

Glu Met Thr Lys Leu Gly Ser Lys Thr Ala Leu Asn Arg Arg Asp Thr
1               5                   10                  15

Tyr Arg Arg Arg Gln Met Gln Arg Thr Ile Thr Arg Gln Met Xaa Phe
            20                  25                  30

Asp Leu Thr Lys Leu Leu Val Thr Glu Asp Trp Phe Ser Asp Ile Ser
        35                  40                  45

Pro Gln Thr Met Arg Arg Leu Leu Asn Ile Val Ser Val
    50                  55                  60

<210> SEQ ID NO 76
<211> LENGTH: 21
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 76

Gly Asp Trp Arg Lys Asn Ile Asp Ala Leu Xaa Gly Met Glu Gly Arg
1               5                   10                  15
```

```
Lys Lys Lys Phe Glu
            20

<210> SEQ ID NO 77
<211> LENGTH: 32
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 77

Glu Asp Thr Glu Lys Glu Asn Arg Glu Val Gly Asp Trp Arg Lys Asn
1               5                   10                  15

Ile Asp Ala Leu Xaa Gly Met Glu Gly Arg Lys Lys Lys Phe Glu Ser
            20                  25                  30

<210> SEQ ID NO 78
<211> LENGTH: 42
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (31)..(31)
<223> OTHER INFORMATION: Xaa can be any naturally occurring amino acid

<400> SEQUENCE: 78

Leu Arg Ala His Leu Lys Gln Val Lys Lys Glu Asp Thr Glu Lys Glu
1               5                   10                  15

Asn Arg Glu Val Gly Asp Trp Arg Lys Asn Ile Asp Ala Leu Xaa Gly
            20                  25                  30

Met Glu Gly Arg Lys Lys Lys Phe Glu Ser
        35                  40

<210> SEQ ID NO 79
<211> LENGTH: 20
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (9)..(10)
<223> OTHER INFORMATION: Xaa can be any naturally occurring amino acid

<400> SEQUENCE: 79

Ala Pro Ala Pro Ile Arg Arg Arg Xaa Xaa Asn Tyr Arg Ala Tyr Ala
1               5                   10                  15

Thr Glu Pro His
            20

<210> SEQ ID NO 80
<211> LENGTH: 41
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (20)..(21)
<223> OTHER INFORMATION: Xaa can be any naturally occurring amino acid

<400> SEQUENCE: 80
```

```
Gly Ser Ser Asp Ala Ala Arg Glu Pro Arg Pro Ala Pro Ala Pro Ile
1               5                   10                  15

Arg Arg Arg Xaa Xaa Asn Tyr Arg Ala Tyr Ala Thr Glu Pro His Ala
            20                  25                  30

Lys Lys Lys Ser Lys Ile Ser Ala Ser
            35                  40
```

<210> SEQ ID NO 81
<211> LENGTH: 53
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (23)..(24)
<223> OTHER INFORMATION: Xaa can be any naturally occurring amino acid

<400> SEQUENCE: 81

```
Met Ala Asp Gly Ser Ser Asp Ala Ala Arg Glu Pro Arg Pro Ala Pro
1               5                   10                  15

Ala Pro Ile Arg Arg Arg Xaa Xaa Asn Tyr Arg Ala Tyr Ala Thr Glu
            20                  25                  30

Pro His Ala Lys Lys Lys Ser Lys Ile Ser Ala Ser Arg Lys Leu Gln
        35                  40                  45

Leu Lys Thr Leu Leu
    50
```

<210> SEQ ID NO 82
<211> LENGTH: 11
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 82

```
Met Gln Gly Leu Ala Glu Arg Ile Xaa Val Leu
1               5                   10
```

<210> SEQ ID NO 83
<211> LENGTH: 21
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (19)..(19)
<223> OTHER INFORMATION: Xaa can be any naturally occurring amino acid

<400> SEQUENCE: 83

```
Gly Gly Ala Cys Pro Pro Gln Asp His Asp Met Gln Gly Leu Ala Glu
1               5                   10                  15

Arg Ile Xaa Val Leu
            20
```

<210> SEQ ID NO 84
<211> LENGTH: 31
<212> TYPE: PRT
<213> ORGANISM: artificial
<220> FEATURE:
<223> OTHER INFORMATION: synthetic
<220> FEATURE:

<221> NAME/KEY: misc_feature
<222> LOCATION: (29)..(29)
<223> OTHER INFORMATION: Xaa can be any naturally occurring amino acid

<400> SEQUENCE: 84

Gly Ser Gly Leu Pro Thr Asp Arg Asp Leu Gly Gly Ala Cys Pro Pro
1               5                   10                  15

Gln Asp His Asp Met Gln Gly Leu Ala Glu Arg Ile Xaa Val Leu
            20                  25                  30

<210> SEQ ID NO 85
<211> LENGTH: 11
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 85

Met Gln Gly Leu Ala Glu Arg Ile Xaa Ile Leu
1               5                   10

<210> SEQ ID NO 86
<211> LENGTH: 21
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (19)..(19)
<223> OTHER INFORMATION: Xaa can be any naturally occurring amino acid

<400> SEQUENCE: 86

Gly Gly Ala Cys Leu Pro Gln Asp His Glu Met Gln Gly Leu Ala Glu
1               5                   10                  15

Arg Ile Xaa Ile Leu
            20

<210> SEQ ID NO 87
<211> LENGTH: 29
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: Xaa can be any naturally occurring amino acid

<400> SEQUENCE: 87

Gly Thr Pro Ala Glu Gly Asp Leu Gly Gly Ala Cys Leu Pro Gln Asp
1               5                   10                  15

His Glu Met Gln Gly Leu Ala Glu Arg Ile Xaa Ile Leu
            20                  25

<210> SEQ ID NO 88
<211> LENGTH: 9
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

```
<400> SEQUENCE: 88

Leu Ala Arg Arg Leu Xaa Phe Ile Gly
1               5

<210> SEQ ID NO 89
<211> LENGTH: 8
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 89

Leu Val Arg Gln Met Xaa Val Ala
1               5

<210> SEQ ID NO 90
<211> LENGTH: 9
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 90

Leu Ser Arg Gln Leu Xaa Ser Gly Val
1               5

<210> SEQ ID NO 91
<211> LENGTH: 10
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 91

Leu Lys Arg Thr Ala Xaa Asn Pro Lys Val
1               5                   10

<210> SEQ ID NO 92
<211> LENGTH: 9
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 92

Leu Arg Lys Thr Val Xaa Glu Pro Asn
1               5

<210> SEQ ID NO 93
<211> LENGTH: 8
<212> TYPE: PRT
<213> ORGANISM: artificial
<220> FEATURE:
```

```
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 93

Leu Leu Arg Lys Glu Xaa Ala Pro
1               5

<210> SEQ ID NO 94
<211> LENGTH: 9
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 94

Leu Ser Arg Ala Gln Xaa Ser Pro Ala
1               5

<210> SEQ ID NO 95
<211> LENGTH: 9
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 95

Leu Ser Arg Thr Arg Xaa Glu Pro Leu
1               5

<210> SEQ ID NO 96
<211> LENGTH: 8
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 96

Leu Ala Glu Arg Ile Xaa Ile Leu
1               5

<210> SEQ ID NO 97
<211> LENGTH: 8
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 97

Leu Ala Glu Arg Ile Xaa Val Leu
1               5
```

```
<210> SEQ ID NO 98
<211> LENGTH: 9
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 98

Ile Thr Arg Gln Met Xaa Phe Asp Leu
1               5

<210> SEQ ID NO 99
<211> LENGTH: 10
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 99

Arg Lys Asn Ile Asp Ala Leu Xaa Gly Met
1               5                   10

<210> SEQ ID NO 100
<211> LENGTH: 10
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (5)..(6)
<223> OTHER INFORMATION: Xaa can be any naturally occurring amino acid

<400> SEQUENCE: 100

Ile Arg Arg Arg Xaa Xaa Asn Tyr Arg Ala
1               5                   10

<210> SEQ ID NO 101
<211> LENGTH: 10
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 101

Leu Leu Arg Ser Met Xaa Ala Ala Phe Cys
1               5                   10

<210> SEQ ID NO 102
<211> LENGTH: 22
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (12)..(12)
<223> OTHER INFORMATION: Xaa can be any naturally occurring amino acid

<400> SEQUENCE: 102
```

```
Leu Gly Arg Arg Arg Pro Leu Leu Arg Ser Met Xaa Ala Ala Phe Cys
1               5                   10                  15

Ser Leu Leu Ala Pro Glu
            20
```

<210> SEQ ID NO 103
<211> LENGTH: 39
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 103

```
Arg Gly Ser Pro Ala Thr Ser Pro His Leu Gly Arg Arg Pro Leu
1               5                   10                  15

Leu Arg Ser Met Xaa Ala Ala Phe Cys Ser Leu Leu Ala Pro Glu Arg
                20                  25                  30

Gln Val Gly Arg Ala Ala Ala
            35
```

<210> SEQ ID NO 104
<211> LENGTH: 60
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (31)..(31)
<223> OTHER INFORMATION: Xaa can be any naturally occurring amino acid

<400> SEQUENCE: 104

```
Ser Ser Glu Glu Glu Gly Val Pro Gly Ser Arg Gly Ser Pro Ala Thr
1               5                   10                  15

Ser Pro His Leu Gly Arg Arg Pro Leu Leu Arg Ser Met Xaa Ala
            20                  25                  30

Ala Phe Cys Ser Leu Leu Ala Pro Glu Arg Gln Val Gly Arg Ala Ala
            35                  40                  45

Ala Ala Leu Met Gln Asp Arg His Thr Ala Ala Gly
        50                  55                  60
```

<210> SEQ ID NO 105
<211> LENGTH: 79
<212> TYPE: PRT
<213> ORGANISM: artificial
<220> FEATURE:
<223> OTHER INFORMATION: synthetic

<400> SEQUENCE: 105

```
Asp Phe Gly Ile Ser Ala Gln Ile Gly Ala Thr Leu Ala Arg Arg Leu
1               5                   10                  15

Ala Phe Ile Gly Thr Pro Tyr Trp Met Ala Pro Glu Ala Gly Ala Gly
                20                  25                  30

Ala Tyr Ser Arg Ala Leu Ser Arg Gln Leu Ala Ser Gly Val Ser Glu
            35                  40                  45

Ile Arg His Thr Ala Asp Gly Ala Gly Ala Ser Leu Ser Ser Asn Leu
        50                  55                  60

Lys Arg Thr Ala Ala Asn Pro Lys Val Glu Asn Glu Asp Glu Pro
65                  70                  75
```

<210> SEQ ID NO 106
<211> LENGTH: 237
<212> TYPE: DNA
<213> ORGANISM: artificial
<220> FEATURE:
<223> OTHER INFORMATION: synthetic

<400> SEQUENCE: 106
gacttcggca tcagcgccca gatcggcgcc accctggcca ggaggctggc cttcatcggc    60
accccctact ggatggcccc cgaggccggc gccggcgcct acagcagggc cctgagcagg   120
cagctggcca gcggcgtgag cgagatcagg cacaccgccg acggcgccgg cgccagcctg   180
agcagcaacc tgaagaggac cgccgccaac cccaaggtgg agaacgagga cgagccc      237

<210> SEQ ID NO 107
<211> LENGTH: 237
<212> TYPE: DNA
<213> ORGANISM: artificial
<220> FEATURE:
<223> OTHER INFORMATION: synthetic

<400> SEQUENCE: 107
gacttcggca tcagcgccca gatcggagcc accctggcta ggaggctggc cttcatcggc    60
accccctact ggatggctcc cgaggctggc gctggagcct acagcagagc cctgagcagg   120
cagctcgcca gcggcgtgag cgagatcagg cacaccgccg acggcgctgg agccagcctg   180
agcagcaacc tgaagaggac cgccgccaac cccaaggtgg agaacgagga cgagccc      237

<210> SEQ ID NO 108
<211> LENGTH: 265
<212> TYPE: DNA
<213> ORGANISM: artificial
<220> FEATURE:
<223> OTHER INFORMATION: synthetic

<400> SEQUENCE: 108
gccggcgact cggcatcag cgcccagatc ggagccaccc tggctaggag gctggccttc    60
atcggcaccc cctactggat ggctcccgag gctggcgctg gagcctacag cagagccctg   120
agcaggcagc tcgccagcgg cgtgagcgag atcaggcaca ccgccgacgg cgctggagcc   180
agcctgagca gcaacctgaa gaggaccgcc gccaaccccaa ggtggagaa cgaggacgag   240 cccccggggg aggcggaat cgatt                                          265

<210> SEQ ID NO 109
<211> LENGTH: 91
<212> TYPE: PRT
<213> ORGANISM: artificial
<220> FEATURE:
<223> OTHER INFORMATION: synthetic

<400> SEQUENCE: 109

Pro Glu His Phe Pro Leu Arg Lys Thr Val Ala Glu Pro Asn Leu Lys
1               5                   10                  15

Leu Arg Tyr Lys Pro Ala Gly Ala Gly Leu Arg Tyr Lys Pro Lys Lys
            20                  25                  30

Ser Leu Glu Arg Arg Lys Asn Pro Leu Leu Arg Lys Glu Ala Ala Pro
        35                  40                  45

Pro Ser Leu Arg Arg Arg Pro Ala Glu Thr Leu Gly Asp Ser Ser Pro
    50                  55                  60

Ser Ser Gly Ala Gly Ala Gly Leu His Trp Pro Leu Ser Arg Thr Arg

```
                65                  70                  75                  80

Ala Glu Pro Leu Pro Pro Ser Ala Thr Ala Pro
                85                  90

<210> SEQ ID NO 110
<211> LENGTH: 273
<212> TYPE: DNA
<213> ORGANISM: artificial
<220> FEATURE:
<223> OTHER INFORMATION: synthetic

<400> SEQUENCE: 110
cccgagcact tcccctgag gaagaccgtg gccgagccca acctgaagct gaggtacaag    60
cccgccggcg ccggcctgag gtacaagccc aagaagagcc tggagaggag gaagaacccc   120
ctgctgagga aggaggccgc cccccccagc ctgaggagga ggcccgccga ccctgggc     180 gacagcagcc ccagcagcgg cgccggcgcc ggcctgcact ggcccctgag caggaccagg   240
gccgagcccc tgcccccag cgccaccgcc ccc                                 273

<210> SEQ ID NO 111
<211> LENGTH: 273
<212> TYPE: DNA
<213> ORGANISM: artificial
<220> FEATURE:
<223> OTHER INFORMATION: synthetic

<400> SEQUENCE: 111
cccgagcact tcccctgag gaagaccgtg gccgagccca acctgaagct gaggtacaag    60
cccgccggag ctggcctgag gtacaagccc aagaaagcc tggagaggag gaagaacccc    120
ctgctgagga aggaggccgc cccccctagc ctgaggagga ggcccgccga ccctgggc     180 gacagcagcc ctagcagcgg agctggcgct ggcctgcact ggcccctgag caggaccagg   240
gccgagcccc tgcccctag cgccaccgcc ccc                                 273

<210> SEQ ID NO 112
<211> LENGTH: 301
<212> TYPE: DNA
<213> ORGANISM: artificial
<220> FEATURE:
<223> OTHER INFORMATION: synthetic

<400> SEQUENCE: 112
gccggccccg agcacttccc cctgaggaag accgtggccg agcccaacct gaagctgagg    60
tacaagcccg ccggagctgg cctgaggtac aagcccaaga aaagcctgga gaggaggaag   120 aacccctgc tgaggaagga ggccgccccc cctagcctga ggaggaggcc cgccgagacc    180
ctgggcgaca gcagccctag cagcggagct ggcgctggcc tgcactggcc cctgagcagg    240
accagggccg agccctgcc cctagcgcc accgccccc cgggggagg cggaatcgat        300 t                                                                   301

<210> SEQ ID NO 113
<211> LENGTH: 89
<212> TYPE: PRT
<213> ORGANISM: artificial
<220> FEATURE:
<223> OTHER INFORMATION: synthetic

<400> SEQUENCE: 113

Asp Phe Gly Ile Ser Ala Gln Ile Gly Ala Thr Leu Ala Arg Arg Leu
1               5                   10                  15
```

```
Ala Phe Ile Gly Thr Pro Tyr Trp Met Ala Pro Glu Ala Ala Leu Val
            20                  25                  30

Arg Gln Met Ala Val Ala Phe Phe Lys Pro Ala Gly Ala Gly Ala
        35                  40                  45

Ala Leu Val Arg Gln Met Ala Val Ala Phe Phe Lys Asp Phe Gly
    50                  55                  60

Ile Ser Ala Gln Ile Gly Ala Thr Leu Ala Arg Arg Leu Ala Phe Ile
65              70                  75                  80

Gly Thr Pro Tyr Trp Met Ala Pro Glu
                85
```

<210> SEQ ID NO 114
<211> LENGTH: 267
<212> TYPE: DNA
<213> ORGANISM: artificial
<220> FEATURE:
<223> OTHER INFORMATION: synthetic

<400> SEQUENCE: 114

```
gacttcggca tcagcgccca gatcggcgcc accctggcca ggaggctggc cttcatcggc    60
acccccctact ggatggcccc cgaggccgcc ctggtgaggc agatggccgt ggccttcttc   120
ttcaagcccg ccggcgccgg cgctgctctc gtcagacaaa tggctgtcgc ttttttttt    180
aaagattttg gaatttccgc tcaaattgga gctacactcg ctagaagact cgcttttatt   240
ggaacacctt attggatggc tcctgaa                                       267
```

<210> SEQ ID NO 115
<211> LENGTH: 267
<212> TYPE: DNA
<213> ORGANISM: artificial
<220> FEATURE:
<223> OTHER INFORMATION: synthetic

<400> SEQUENCE: 115

```
gacttcggca tcagcgccca gatcggagcc accctggcta ggaggctggc cttcatcggc    60
acccccctact ggatggcccc cgaggctgcc ctggtgaggc agatggccgt ggccttcttc   120
ttcaagcccg ccggagccgg agctgctctc gtcagacaaa tggctgtcgc ttttttttt    180
aaagattttg gaatttccgc tcaaattgga gctacactcg ctagaagact cgcttttatt   240
ggaacacctt attggatggc tcctgaa                                       267
```

<210> SEQ ID NO 116
<211> LENGTH: 295
<212> TYPE: DNA
<213> ORGANISM: artificial
<220> FEATURE:
<223> OTHER INFORMATION: synthetic

<400> SEQUENCE: 116

```
gccggcgact tcggcatcag cgcccagatc ggagccaccc tggctaggag gctggccttc    60
atcggcaccc cctactggat ggcccccgag gctgccctgg tgaggcagat ggccgtggcc   120
ttcttcttca gcccgccgg agccggagct gctctcgtca acaaatggc tgtcgctttt    180
ttttttaaag attttggaat tccgctcaa attggagcta cactcgctag aagactcgct   240
tttattggaa caccttattg gatggctcct gaacccgggg gaggcggaat cgatt        295
```

<210> SEQ ID NO 117
<211> LENGTH: 210
<212> TYPE: PRT
<213> ORGANISM: human

```
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid

<400> SEQUENCE: 117

Met Ala Asp Gly Ser Ser Asp Ala Ala Arg Glu Pro Arg Pro Ala Pro
1               5                   10                  15

Ala Pro Ile Arg Arg Arg Xaa Xaa Asn Tyr Arg Ala Tyr Ala Thr Glu
            20                  25                  30

Pro His Ala Lys Lys Lys Ser Lys Ile Ser Ala Ser Arg Lys Leu Gln
        35                  40                  45

Leu Lys Thr Leu Leu Leu Gln Ile Ala Lys Gln Glu Leu Glu Arg Glu
    50                  55                  60

Ala Glu Glu Arg Arg Gly Glu Lys Gly Arg Ala Leu Ser Thr Arg Cys
65                  70                  75                  80

Gln Pro Leu Glu Leu Ala Gly Leu Gly Phe Ala Glu Leu Gln Asp Leu
                85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
        115                 120                 125

Thr Gln Lys Ile Phe Asp Leu Arg Gly Lys Phe Lys Arg Pro Thr Leu
    130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Xaa Gly Met Glu Gly Arg Lys Lys Lys Phe
        195                 200                 205

Glu Ser
    210

<210> SEQ ID NO 118
<211> LENGTH: 882
<212> TYPE: PRT
<213> ORGANISM: human
<220> FEATURE:
<221> NAME/KEY: misc_feature
<222> LOCATION: (850)..(850)
<223> OTHER INFORMATION: Xaa can be any naturally occurring amino acid
<220> FEATURE:
<221> NAME/KEY: misc_feature
<222> LOCATION: (853)..(853)
<223> OTHER INFORMATION: Xaa can be any naturally occurring amino acid

<400> SEQUENCE: 118

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60
```

-continued

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
            85                  90                  95

His Phe Leu Val Tyr Ala Trp Asp Ser Thr Tyr Arg Lys Phe Ser Thr
            100                 105                 110

Lys Val Thr Leu Asn Thr Val Gly His His Arg Pro Pro His
        115                 120                 125

Gln Ala Ser Val Ser Gly Ile Gln Ala Glu Leu Leu Thr Phe Pro Asn
130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
            165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
            245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285

Ala Asp Asp Asp Val Asn Thr Tyr Asn Ala Ala Ile Ala Tyr Thr Ile
        290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
            325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
        355                 360                 365

Asn Asp Asn Pro Pro Ile Phe Asn Pro Thr Thr Tyr Lys Gly Gln Val
370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
            405                 410                 415

Asn Asp Asp Gly Gly Gln Phe Val Val Thr Asn Pro Val Asn Asn
            420                 425                 430

Asp Gly Ile Leu Lys Thr Ala Lys Gly Leu Asp Phe Glu Ala Lys Gln
        435                 440                 445

Gln Tyr Ile Leu His Val Ala Val Thr Asn Val Val Pro Phe Glu Val
        450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser

```
                    485                 490                 495
Glu Asp Phe Gly Val Gly Gln Glu Ile Thr Ser Tyr Thr Ala Gln Glu
                500                 505                 510

Pro Asp Thr Phe Met Glu Gln Lys Ile Thr Tyr Arg Ile Trp Arg Asp
            515                 520                 525

Thr Ala Asn Trp Leu Glu Ile Asn Pro Asp Thr Gly Ala Ile Phe Thr
        530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Ile Leu Ser Asp Val Asn Asp Asn Ala
                580                 585                 590

Pro Ile Pro Glu Pro Arg Thr Ile Phe Phe Cys Glu Arg Asn Pro Lys
            595                 600                 605

Pro Gln Val Ile Asn Ile Asp Ala Asp Leu Pro Pro Asn Thr Ser
        610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
                660                 665                 670

Gln Asn Lys Asp Gln Val Thr Thr Leu Glu Val Ser Val Cys Asp Cys
            675                 680                 685

Glu Gly Ala Ala Gly Val Cys Arg Lys Ala Gln Pro Val Glu Ala Gly
        690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Phe Leu Arg Arg Arg Ala Val
                725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Glu Glu Asp Gln Asp Phe Asp
        755                 760                 765

Leu Ser Gln Leu His Arg Gly Leu Asp Ala Arg Pro Glu Val Thr Arg
770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
                820                 825                 830

Phe Asp Tyr Glu Gly Ser Gly Ser Glu Ala Ala Ser Leu Ser Ser Leu
            835                 840                 845

Asn Xaa Ser Glu Xaa Asp Lys Asp Gln Asp Tyr Asp Tyr Leu Asn Glu
        850                 855                 860

Trp Gly Asn Arg Phe Lys Lys Leu Ala Asp Met Tyr Gly Gly Gly Glu
865                 870                 875                 880

Asp Asp

<210> SEQ ID NO 119
<211> LENGTH: 1123
<212> TYPE: PRT
```

```
<213> ORGANISM: human
<220> FEATURE:
<221> NAME/KEY: misc_feature
<222> LOCATION: (260)..(260)
<223> OTHER INFORMATION: Xaa can be any naturally occurring amino acid
<220> FEATURE:
<221> NAME/KEY: misc_feature
<222> LOCATION: (499)..(499)
<223> OTHER INFORMATION: Xaa can be any naturally occurring amino acid

<400> SEQUENCE: 119
```

Met Asn Ser Pro Asn Glu Ser Ala Asp Gly Met Ser Gly Arg Glu Pro
1               5                   10                  15

Ser Leu Glu Ile Leu Pro Arg Thr Ser Leu His Ser Ile Pro Val Thr
            20                  25                  30

Val Glu Val Lys Pro Val Leu Pro Arg Ala Met Pro Ser Ser Met Gly
        35                  40                  45

Gly Gly Gly Gly Gly Ser Pro Ser Pro Val Glu Leu Arg Gly Ala Leu
    50                  55                  60

Val Gly Ser Val Asp Pro Thr Leu Arg Glu Gln Gln Leu Gln Gln Glu
65                  70                  75                  80

Leu Leu Ala Leu Lys Gln Gln Gln Leu Gln Lys Gln Leu Leu Phe
                85                  90                  95

Ala Glu Phe Gln Lys Gln His Asp His Leu Thr Arg Gln His Glu Val
                100                 105                 110

Gln Leu Gln Lys His Leu Lys Gln Gln Glu Met Leu Ala Ala Lys
            115                 120                 125

Gln Gln Gln Glu Met Leu Ala Ala Lys Arg Gln Gln Glu Leu Glu Gln
    130                 135                 140

Gln Arg Gln Arg Glu Gln Gln Arg Gln Glu Glu Leu Glu Lys Gln Arg
145                 150                 155                 160

Leu Glu Gln Gln Leu Leu Ile Leu Arg Asn Lys Glu Lys Ser Lys Glu
                165                 170                 175

Ser Ala Ile Ala Ser Thr Glu Val Lys Leu Arg Leu Gln Glu Phe Leu
                180                 185                 190

Leu Ser Lys Ser Lys Glu Pro Thr Pro Gly Gly Leu Asn His Ser Leu
                195                 200                 205

Pro Gln His Pro Lys Cys Trp Gly Ala His His Ala Ser Leu Asp Gln
                210                 215                 220

Ser Ser Pro Pro Gln Ser Gly Pro Pro Gly Thr Pro Pro Ser Tyr Lys
225                 230                 235                 240

Leu Pro Leu Pro Gly Pro Tyr Asp Ser Arg Asp Asp Phe Pro Leu Arg
                245                 250                 255

Lys Thr Ala Xaa Glu Pro Asn Leu Lys Val Arg Ser Arg Leu Lys Gln
                260                 265                 270

Lys Val Ala Glu Arg Arg Ser Ser Pro Leu Leu Arg Arg Lys Asp Gly
            275                 280                 285

Thr Val Ile Ser Thr Phe Lys Lys Arg Ala Val Glu Ile Thr Gly Ala
    290                 295                 300

Gly Pro Gly Ala Ser Ser Val Cys Asn Ser Ala Pro Gly Ser Gly Pro
305                 310                 315                 320

Ser Ser Pro Asn Ser Ser His Ser Thr Ile Ala Glu Asn Gly Phe Thr
                325                 330                 335

Gly Ser Val Pro Asn Ile Pro Thr Glu Met Leu Pro Gln His Arg Ala
                340                 345                 350

Leu Pro Leu Asp Ser Ser Pro Asn Gln Phe Ser Leu Tyr Thr Ser Pro
                355                 360                 365

```
Ser Leu Pro Asn Ile Ser Leu Gly Leu Gln Ala Thr Val Thr Val Thr
    370                 375                 380

Asn Ser His Leu Thr Ala Ser Pro Lys Leu Ser Thr Gln Gln Glu Ala
385                 390                 395                 400

Glu Arg Gln Ala Leu Gln Ser Leu Arg Gln Gly Thr Leu Thr Gly Gly
                405                 410                 415

Lys Phe Met Ser Thr Ser Ser Ile Pro Gly Cys Leu Leu Gly Val Ala
            420                 425                 430

Leu Glu Gly Asp Gly Ser Pro His Gly His Ala Ser Leu Leu Gln His
        435                 440                 445

Val Leu Leu Glu Gln Ala Arg Gln Gln Ser Thr Leu Ile Ala Val
    450                 455                 460

Pro Leu His Gly Gln Ser Pro Leu Val Thr Gly Glu Arg Val Ala Thr
465                 470                 475                 480

Ser Met Arg Thr Val Gly Lys Leu Pro Arg His Arg Pro Leu Ser Arg
                485                 490                 495

Thr Gln Xaa Ser Pro Leu Pro Gln Ser Pro Gln Ala Leu Gln Gln Leu
            500                 505                 510

Val Met Gln Gln Gln His Gln Gln Phe Leu Glu Lys Gln Lys Gln Gln
    515                 520                 525

Gln Leu Gln Leu Gly Lys Ile Leu Thr Lys Thr Gly Glu Leu Pro Arg
530                 535                 540

Gln Pro Thr Thr His Pro Glu Glu Thr Glu Glu Leu Thr Glu Gln
545                 550                 555                 560

Gln Glu Val Leu Leu Gly Glu Gly Ala Leu Thr Met Pro Arg Glu Gly
                565                 570                 575

Ser Thr Glu Ser Glu Ser Thr Gln Glu Asp Leu Glu Glu Glu Asp Glu
            580                 585                 590

Glu Asp Asp Gly Glu Glu Glu Asp Cys Ile Gln Val Lys Asp Glu
        595                 600                 605

Glu Gly Glu Ser Gly Ala Glu Glu Gly Pro Asp Leu Glu Glu Pro Gly
    610                 615                 620

Ala Gly Tyr Lys Lys Leu Phe Ser Asp Ala Gln Pro Leu Gln Pro Leu
625                 630                 635                 640

Gln Val Tyr Gln Ala Pro Leu Ser Leu Ala Thr Val Pro His Gln Ala
                645                 650                 655

Leu Gly Arg Thr Gln Ser Ser Pro Ala Ala Pro Gly Gly Met Lys Ser
            660                 665                 670

Pro Pro Asp Gln Pro Val Lys His Leu Phe Thr Thr Gly Val Val Tyr
        675                 680                 685

Asp Thr Phe Met Leu Lys His Gln Cys Met Cys Gly Asn Thr His Val
    690                 695                 700

His Pro Glu His Ala Gly Arg Ile Gln Ser Ile Trp Ser Arg Leu Gln
705                 710                 715                 720

Glu Thr Gly Leu Leu Ser Lys Cys Glu Arg Ile Arg Gly Arg Lys Ala
                725                 730                 735

Thr Leu Asp Glu Ile Gln Thr Val His Ser Glu Tyr His Thr Leu Leu
            740                 745                 750

Tyr Gly Thr Ser Pro Leu Asn Arg Gln Lys Leu Asp Ser Lys Lys Leu
        755                 760                 765

Leu Gly Pro Ile Ser Gln Lys Met Tyr Ala Val Leu Pro Cys Gly Gly
    770                 775                 780

Ile Gly Val Asp Ser Asp Thr Val Trp Asn Glu Met His Ser Ser Ser
```

```
                785                 790                 795                 800
Ala Val Arg Met Ala Val Gly Cys Leu Leu Glu Leu Ala Phe Lys Val
            805                 810                 815

Ala Ala Gly Glu Leu Lys Asn Gly Phe Ala Ile Ile Arg Pro Pro Gly
            820                 825                 830

His His Ala Glu Glu Ser Thr Ala Met Gly Phe Cys Phe Phe Asn Ser
            835                 840                 845

Val Ala Ile Thr Ala Lys Leu Leu Gln Gln Lys Leu Asn Val Gly Lys
            850                 855                 860

Val Leu Ile Val Asp Trp Asp Ile His His Gly Asn Gly Thr Gln Gln
865                 870                 875                 880

Ala Phe Tyr Asn Asp Pro Ser Val Leu Tyr Ile Ser Leu His Arg Tyr
            885                 890                 895

Asp Asn Gly Asn Phe Phe Pro Gly Ser Gly Ala Pro Glu Glu Val Gly
            900                 905                 910

Gly Gly Pro Gly Val Gly Tyr Asn Val Asn Val Ala Trp Thr Gly Gly
            915                 920                 925

Val Asp Pro Pro Ile Gly Asp Val Glu Tyr Leu Thr Ala Phe Arg Thr
            930                 935                 940

Val Val Met Pro Ile Ala His Glu Phe Ser Pro Asp Val Val Leu Val
945                 950                 955                 960

Ser Ala Gly Phe Asp Ala Val Glu Gly His Leu Ser Pro Leu Gly Gly
            965                 970                 975

Tyr Ser Val Thr Ala Arg Cys Phe Gly His Leu Thr Arg Gln Leu Met
            980                 985                 990

Thr Leu Ala Gly Gly Arg Val Val  Leu Ala Leu Glu Gly  Gly His Asp
        995                 1000                1005

Leu Thr  Ala Ile Cys Asp Ala  Ser Glu Ala Cys Val  Ser Ala Leu
    1010                1015                1020

Leu Ser  Val Glu Leu Gln Pro  Leu Asp Glu Ala Val  Leu Gln Gln
    1025                1030                1035

Lys Pro  Asn Ile Asn Ala Val  Ala Thr Leu Glu Lys  Val Ile Glu
    1040                1045                1050

Ile Gln  Ser Lys His Trp Ser  Cys Val Gln Lys Phe  Ala Ala Gly
    1055                1060                1065

Leu Gly  Arg Ser Leu Arg Glu  Ala Gln Ala Gly Glu  Thr Glu Glu
    1070                1075                1080

Ala Glu  Thr Val Ser Ala Met  Ala Leu Leu Ser Val  Gly Ala Glu
    1085                1090                1095

Gln Ala  Gln Ala Ala Ala Ala  Arg Glu His Ser Pro  Arg Pro Ala
    1100                1105                1110

Glu Glu  Pro Met Glu Gln Glu  Pro Ala Leu
    1115                1120

<210> SEQ ID NO 120
<211> LENGTH: 954
<212> TYPE: PRT
<213> ORGANISM: human
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: misc_feature
```

```
<222> LOCATION: (360)..(360)
<223> OTHER INFORMATION: Xaa can be any naturally occurring amino acid
<220> FEATURE:
<221> NAME/KEY: misc_feature
<222> LOCATION: (488)..(488)
<223> OTHER INFORMATION: Xaa can be any naturally occurring amino acid

<400> SEQUENCE: 120

Met His Ser Pro Gly Ala Asp Gly Thr Gln Val Ser Pro Gly Ala His
1               5                   10                  15

Tyr Cys Ser Pro Thr Gly Ala Gly Cys Pro Arg Pro Cys Ala Asp Thr
            20                  25                  30

Pro Gly Pro Gln Pro Gln Pro Met Asp Leu Arg Val Gly Gln Arg Pro
        35                  40                  45

Pro Val Glu Pro Pro Glu Pro Thr Leu Leu Ala Leu Gln Arg Pro
    50                  55                  60

Gln Arg Leu His His His Leu Phe Leu Ala Gly Leu Gln Gln Arg
65              70                  75                  80

Ser Val Glu Pro Met Arg Leu Ser Met Asp Thr Pro Met Pro Glu Leu
                85                  90                  95

Gln Val Gly Pro Gln Glu Gln Glu Leu Arg Gln Leu Leu His Lys Asp
            100                 105                 110

Lys Ser Lys Arg Ser Ala Val Ala Ser Ser Val Val Lys Gln Lys Leu
        115                 120                 125

Ala Glu Val Ile Leu Lys Lys Gln Gln Ala Ala Leu Glu Arg Thr Val
    130                 135                 140

His Pro Asn Ser Pro Gly Ile Pro Tyr Arg Thr Leu Glu Pro Leu Glu
145                 150                 155                 160

Thr Glu Gly Ala Thr Arg Ser Met Leu Ser Ser Phe Leu Pro Pro Val
                165                 170                 175

Pro Ser Leu Pro Ser Asp Pro Pro Glu His Phe Pro Leu Arg Lys Thr
            180                 185                 190

Val Xaa Glu Pro Asn Leu Lys Leu Arg Tyr Lys Pro Lys Lys Ser Leu
        195                 200                 205

Glu Arg Arg Lys Asn Pro Leu Leu Arg Lys Glu Xaa Ala Pro Pro Ser
210                 215                 220

Leu Arg Arg Arg Pro Ala Glu Thr Leu Gly Asp Ser Ser Pro Ser Ser
225                 230                 235                 240

Ser Ser Thr Pro Ala Ser Gly Cys Ser Ser Pro Asn Asp Ser Glu His
            245                 250                 255

Gly Pro Asn Pro Ile Leu Gly Ser Glu Ala Asp Ser Asp Arg Arg Thr
        260                 265                 270

His Pro Thr Leu Gly Pro Arg Gly Pro Ile Leu Gly Ser Pro His Thr
    275                 280                 285

Pro Leu Phe Leu Pro His Gly Leu Glu Pro Glu Ala Gly Gly Thr Leu
290                 295                 300

Pro Ser Arg Leu Gln Pro Ile Leu Leu Leu Asp Pro Ser Gly Ser His
305                 310                 315                 320

Ala Pro Leu Leu Thr Val Pro Gly Leu Gly Pro Leu Pro Phe His Phe
            325                 330                 335

Ala Gln Ser Leu Met Thr Thr Glu Arg Leu Ser Gly Ser Gly Leu His
        340                 345                 350

Trp Pro Leu Ser Arg Thr Arg Xaa Glu Pro Leu Pro Pro Ser Ala Thr
    355                 360                 365

Ala Pro Pro Pro Gly Pro Met Gln Pro Arg Leu Glu Gln Leu Lys
370                 375                 380
```

```
Thr His Val Gln Val Ile Lys Arg Ser Ala Lys Pro Ser Glu Lys Pro
385                 390                 395                 400

Arg Leu Arg Gln Ile Pro Ser Ala Glu Asp Leu Glu Thr Asp Gly Gly
            405                 410                 415

Gly Pro Gly Gln Val Val Asp Asp Gly Leu Glu His Arg Glu Leu Gly
            420                 425                 430

His Gly Gln Pro Glu Ala Arg Gly Pro Ala Pro Leu Gln Gln His Pro
            435                 440                 445

Gln Val Leu Leu Trp Glu Gln Arg Leu Ala Gly Arg Leu Pro Arg
    450                 455                 460

Gly Ser Thr Gly Asp Thr Val Leu Leu Pro Leu Ala Gln Gly Gly His
465                 470                 475                 480

Arg Pro Leu Ser Arg Ala Gln Xaa Ser Pro Ala Ala Pro Ala Ser Leu
            485                 490                 495

Ser Ala Pro Glu Pro Ala Ser Gln Ala Arg Val Leu Ser Ser Ser Glu
            500                 505                 510

Thr Pro Ala Arg Thr Leu Pro Phe Thr Thr Gly Leu Ile Tyr Asp Ser
            515                 520                 525

Val Met Leu Lys His Gln Cys Ser Cys Gly Asp Asn Ser Arg His Pro
530                 535                 540

Glu His Ala Gly Arg Ile Gln Ser Ile Trp Ser Arg Leu Gln Glu Arg
545                 550                 555                 560

Gly Leu Arg Ser Gln Cys Glu Cys Leu Arg Gly Arg Lys Ala Ser Leu
            565                 570                 575

Glu Glu Leu Gln Ser Val His Ser Glu Arg His Val Leu Leu Tyr Gly
            580                 585                 590

Thr Asn Pro Leu Ser Arg Leu Lys Leu Asp Asn Gly Lys Leu Ala Gly
            595                 600                 605

Leu Leu Ala Gln Arg Met Phe Val Met Leu Pro Cys Gly Gly Val Gly
            610                 615                 620

Val Asp Thr Asp Thr Ile Trp Asn Glu Leu His Ser Ser Asn Ala Ala
625                 630                 635                 640

Arg Trp Ala Ala Gly Ser Val Thr Asp Leu Ala Phe Lys Val Ala Ser
            645                 650                 655

Arg Glu Leu Lys Asn Gly Phe Ala Val Val Arg Pro Pro Gly His His
            660                 665                 670

Ala Asp His Ser Thr Ala Met Gly Phe Cys Phe Phe Asn Ser Val Ala
            675                 680                 685

Ile Ala Cys Arg Gln Leu Gln Gln Gln Ser Lys Ala Ser Lys Ile Leu
            690                 695                 700

Ile Val Asp Trp Asp Val His His Gly Asn Gly Thr Gln Gln Thr Phe
705                 710                 715                 720

Tyr Gln Asp Pro Ser Val Leu Tyr Ile Ser Leu His Arg His Asp Asp
            725                 730                 735

Gly Asn Phe Phe Pro Gly Ser Gly Ala Val Asp Glu Val Gly Ala Gly
            740                 745                 750

Ser Gly Glu Gly Phe Asn Val Asn Val Ala Trp Ala Gly Gly Leu Asp
            755                 760                 765

Pro Pro Met Gly Asp Pro Glu Tyr Leu Ala Ala Phe Arg Ile Val Val
            770                 775                 780

Met Pro Ile Ala Arg Glu Phe Ser Pro Asp Leu Val Leu Val Ser Ala
785                 790                 795                 800

Gly Phe Asp Ala Ala Glu Gly His Pro Ala Pro Leu Gly Gly Tyr His
```

```
                    805                 810                 815
Val Ser Ala Lys Cys Phe Gly Tyr Met Thr Gln Gln Leu Met Asn Leu
            820                 825                 830

Ala Gly Gly Ala Val Val Leu Ala Leu Glu Gly Gly His Asp Leu Thr
        835                 840                 845

Ala Ile Cys Asp Ala Ser Glu Ala Cys Val Ala Ala Leu Leu Gly Asn
    850                 855                 860

Arg Val Asp Pro Leu Ser Glu Glu Gly Trp Lys Gln Lys Pro Asn Leu
865                 870                 875                 880

Asn Ala Ile Arg Ser Leu Glu Ala Val Ile Arg Val His Ser Lys Tyr
                885                 890                 895

Trp Gly Cys Met Gln Arg Leu Ala Ser Cys Pro Asp Ser Trp Val Pro
            900                 905                 910

Arg Val Pro Gly Ala Asp Lys Glu Glu Val Glu Ala Val Thr Ala Leu
        915                 920                 925

Ala Ser Leu Ser Val Gly Ile Leu Ala Glu Asp Arg Pro Ser Glu Gln
    930                 935                 940

Leu Val Glu Glu Glu Pro Met Asn Leu
945                 950

<210> SEQ ID NO 121
<211> LENGTH: 833
<212> TYPE: PRT
<213> ORGANISM: human
<220> FEATURE:
<221> NAME/KEY: misc_feature
<222> LOCATION: (171)..(171)
<223> OTHER INFORMATION: Xaa can be any naturally occurring amino acid

<400> SEQUENCE: 121

Met Asp Val Val Asp Pro Asp Ile Phe Asn Arg Asp Pro Arg Asp His
1               5                   10                  15

Tyr Asp Leu Leu Gln Arg Leu Gly Gly Gly Thr Tyr Gly Glu Val Phe
            20                  25                  30

Lys Ala Arg Asp Lys Val Ser Gly Asp Leu Val Ala Leu Lys Met Val
        35                  40                  45

Lys Met Glu Pro Asp Asp Asp Val Ser Thr Leu Gln Lys Glu Ile Leu
    50                  55                  60

Ile Leu Lys Thr Cys Arg His Ala Asn Ile Val Ala Tyr His Gly Ser
65                  70                  75                  80

Tyr Leu Trp Leu Gln Lys Leu Trp Ile Cys Met Glu Phe Cys Gly Ala
                85                  90                  95

Gly Ser Leu Gln Asp Ile Tyr Gln Val Thr Gly Ser Leu Ser Glu Leu
            100                 105                 110

Gln Ile Ser Tyr Val Cys Arg Glu Val Leu Gln Gly Leu Ala Tyr Leu
        115                 120                 125

His Ser Gln Lys Lys Ile His Arg Asp Ile Lys Gly Ala Asn Ile Leu
    130                 135                 140

Ile Asn Asp Ala Gly Glu Val Arg Leu Ala Asp Phe Gly Ile Ser Ala
145                 150                 155                 160

Gln Ile Gly Ala Thr Leu Ala Arg Arg Leu Xaa Phe Ile Gly Thr Pro
                165                 170                 175

Tyr Trp Met Ala Pro Glu Val Ala Ala Val Ala Leu Lys Gly Gly Tyr
            180                 185                 190

Asn Glu Leu Cys Asp Ile Trp Ser Leu Gly Ile Thr Ala Ile Glu Leu
        195                 200                 205
```

-continued

Ala Glu Leu Gln Pro Pro Leu Phe Asp Val His Pro Leu Arg Val Leu
    210                 215                 220

Phe Leu Met Thr Lys Ser Gly Tyr Gln Pro Arg Leu Lys Glu Lys
225             230                 235                 240

Gly Lys Trp Ser Ala Ala Phe His Asn Phe Ile Lys Val Thr Leu Thr
                245                 250                 255

Lys Ser Pro Lys Lys Arg Pro Ser Ala Thr Lys Met Leu Ser His Gln
            260                 265                 270

Leu Val Ser Gln Pro Gly Leu Asn Arg Gly Leu Ile Leu Asp Leu Leu
        275                 280                 285

Asp Lys Leu Lys Asn Pro Gly Lys Gly Pro Ser Ile Gly Asp Ile Glu
    290                 295                 300

Asp Glu Glu Pro Glu Leu Pro Pro Ala Ile Pro Arg Arg Ile Arg Ser
305                 310                 315                 320

Thr His Arg Ser Ser Ser Leu Gly Ile Pro Asp Ala Asp Cys Cys Arg
                325                 330                 335

Arg His Met Glu Phe Arg Lys Leu Arg Gly Met Glu Thr Arg Pro Pro
            340                 345                 350

Ala Asn Thr Ala Arg Leu Gln Pro Pro Arg Asp Leu Arg Ser Ser Ser
        355                 360                 365

Pro Arg Lys Gln Leu Ser Glu Ser Ser Asp Asp Tyr Asp Asp Val
    370                 375                 380

Asp Ile Pro Thr Pro Ala Glu Asp Thr Pro Pro Pro Leu Pro Pro Lys
385                 390                 395                 400

Pro Lys Phe Arg Ser Pro Ser Asp Glu Gly Pro Gly Ser Met Gly Asp
                405                 410                 415

Asp Gly Gln Leu Ser Pro Gly Val Leu Val Arg Cys Ala Ser Gly Pro
            420                 425                 430

Pro Pro Asn Ser Pro Arg Pro Gly Pro Pro Ser Thr Ser Ser Pro
        435                 440                 445

His Leu Thr Ala His Ser Glu Pro Ser Leu Trp Asn Pro Pro Ser Arg
    450                 455                 460

Glu Leu Asp Lys Pro Pro Leu Leu Pro Pro Lys Lys Glu Lys Met Lys
465                 470                 475                 480

Arg Lys Gly Cys Ala Leu Leu Val Lys Leu Phe Asn Gly Cys Pro Leu
                485                 490                 495

Arg Ile His Ser Thr Ala Ala Trp Thr His Pro Ser Thr Lys Asp Gln
            500                 505                 510

His Leu Leu Leu Gly Ala Glu Gly Ile Phe Ile Leu Asn Arg Asn
        515                 520                 525

Asp Gln Glu Ala Thr Leu Glu Met Leu Phe Pro Ser Arg Thr Thr Trp
    530                 535                 540

Val Tyr Ser Ile Asn Asn Val Leu Met Ser Leu Ser Gly Lys Thr Pro
545                 550                 555                 560

His Leu Tyr Ser His Ser Ile Leu Gly Leu Leu Glu Arg Lys Glu Thr
                565                 570                 575

Arg Ala Gly Asn Pro Ile Ala His Ile Ser Pro His Arg Leu Leu Ala
            580                 585                 590

Arg Lys Asn Met Val Ser Thr Lys Ile Gln Asp Thr Lys Gly Cys Arg
        595                 600                 605

Ala Cys Cys Val Ala Glu Gly Ala Ser Ser Gly Gly Pro Phe Leu Cys
    610                 615                 620

Gly Ala Leu Glu Thr Ser Val Val Leu Leu Gln Trp Tyr Gln Pro Met
625                 630                 635                 640

```
Asn Lys Phe Leu Leu Val Arg Gln Val Leu Phe Pro Leu Pro Thr Pro
                645                 650                 655
Leu Ser Val Phe Ala Leu Leu Thr Gly Pro Gly Ser Glu Leu Pro Ala
                660                 665                 670
Val Cys Ile Gly Val Ser Pro Gly Arg Pro Gly Lys Ser Val Leu Phe
                675                 680                 685
His Thr Val Arg Phe Gly Ala Leu Ser Cys Trp Leu Gly Glu Met Ser
                690                 695                 700
Thr Glu His Arg Gly Pro Val Gln Val Thr Gln Val Glu Glu Asp Met
705                 710                 715                 720
Val Met Val Leu Met Asp Gly Ser Val Lys Leu Val Thr Pro Glu Gly
                725                 730                 735
Ser Pro Val Arg Gly Leu Arg Thr Pro Glu Ile Pro Met Thr Glu Ala
                740                 745                 750
Val Glu Ala Val Ala Met Val Gly Gly Gln Leu Gln Ala Phe Trp Lys
                755                 760                 765
His Gly Val Gln Val Trp Ala Leu Gly Ser Asp Gln Leu Leu Gln Glu
                770                 775                 780
Leu Arg Asp Pro Thr Leu Thr Phe Arg Leu Leu Gly Ser Pro Arg Leu
785                 790                 795                 800
Glu Cys Ser Gly Thr Ile Ser Pro His Cys Asn Leu Leu Leu Pro Gly
                805                 810                 815
Ser Ser Asn Ser Pro Ala Ser Ala Ser Arg Val Ala Gly Ile Thr Gly
                820                 825                 830
Leu

<210> SEQ ID NO 122
<211> LENGTH: 205
<212> TYPE: PRT
<213> ORGANISM: human
<220> FEATURE:
<221> NAME/KEY: misc_feature
<222> LOCATION: (82)..(82)
<223> OTHER INFORMATION: Xaa can be any naturally occurring amino acid

<400> SEQUENCE: 122

Met Thr Glu Arg Arg Val Pro Phe Ser Leu Leu Arg Gly Pro Ser Trp
1               5                   10                  15
Asp Pro Phe Arg Asp Trp Tyr Pro His Ser Arg Leu Phe Asp Gln Ala
                20                  25                  30
Phe Gly Leu Pro Arg Leu Pro Glu Glu Trp Ser Gln Trp Leu Gly Gly
                35                  40                  45
Ser Ser Trp Pro Gly Tyr Val Arg Pro Leu Pro Pro Ala Ala Ile Glu
                50                  55                  60
Ser Pro Ala Val Ala Ala Pro Ala Tyr Ser Arg Ala Leu Ser Arg Gln
65                  70                  75                  80
Leu Xaa Ser Gly Val Ser Glu Ile Arg His Thr Ala Asp Arg Trp Arg
                85                  90                  95
Val Ser Leu Asp Val Asn His Phe Ala Pro Asp Glu Leu Thr Val Lys
                100                 105                 110
Thr Lys Asp Gly Val Val Glu Ile Thr Gly Lys His Glu Glu Arg Gln
                115                 120                 125
Asp Glu His Gly Tyr Ile Ser Arg Cys Phe Thr Arg Lys Tyr Thr Leu
                130                 135                 140
Pro Pro Gly Val Asp Pro Thr Gln Val Ser Ser Ser Leu Ser Pro Glu
145                 150                 155                 160
```

Gly Thr Leu Thr Val Glu Ala Pro Met Pro Lys Leu Ala Thr Gln Ser
              165                 170                 175

Asn Glu Ile Thr Ile Pro Val Thr Phe Glu Ser Arg Ala Gln Leu Gly
              180                 185                 190

Gly Pro Glu Ala Ala Lys Ser Asp Glu Thr Ala Ala Lys
              195                 200                 205

<210> SEQ ID NO 123
<211> LENGTH: 1771
<212> TYPE: PRT
<213> ORGANISM: human
<220> FEATURE:
<221> NAME/KEY: misc_feature
<222> LOCATION: (918)..(918)
<223> OTHER INFORMATION: Xaa can be any naturally occurring amino acid

<400> SEQUENCE: 123

Met Ser Val Leu Ile Ser Gln Ser Val Ile Asn Tyr Val Glu Glu
1               5                   10                  15

Asn Ile Pro Ala Leu Lys Ala Leu Leu Glu Lys Cys Lys Asp Val Asp
                20                  25                  30

Glu Arg Asn Glu Cys Gly Gln Thr Pro Leu Met Ile Ala Ala Glu Gln
            35                  40                  45

Gly Asn Leu Glu Ile Val Lys Glu Leu Ile Lys Asn Gly Ala Asn Cys
        50                  55                  60

Asn Leu Glu Asp Leu Asp Asn Trp Thr Ala Leu Ile Ser Ala Ser Lys
65                  70                  75                  80

Glu Gly His Val His Ile Val Glu Leu Leu Lys Cys Gly Val Asn
                85                  90                  95

Leu Glu His Arg Asp Met Gly Gly Trp Thr Ala Leu Met Trp Ala Cys
            100                 105                 110

Tyr Lys Gly Arg Thr Asp Val Val Glu Leu Leu Leu Ser His Gly Ala
        115                 120                 125

Asn Pro Ser Val Thr Gly Leu Tyr Ser Val Tyr Pro Ile Ile Trp Ala
    130                 135                 140

Ala Gly Arg Gly His Ala Asp Ile Val His Leu Leu Leu Gln Asn Gly
145                 150                 155                 160

Ala Lys Val Asn Cys Ser Asp Lys Tyr Gly Thr Thr Pro Leu Val Trp
                165                 170                 175

Ala Ala Arg Lys Gly His Leu Glu Cys Val Lys His Leu Leu Ala Met
            180                 185                 190

Gly Ala Asp Val Asp Gln Glu Gly Ala Asn Ser Met Thr Ala Leu Ile
        195                 200                 205

Val Ala Val Lys Gly Gly Tyr Thr Gln Ser Val Lys Glu Ile Leu Lys
    210                 215                 220

Arg Asn Pro Asn Val Asn Leu Thr Asp Lys Asp Gly Asn Thr Ala Leu
225                 230                 235                 240

Met Ile Ala Ser Lys Glu Gly His Thr Glu Ile Val Gln Asp Leu Leu
                245                 250                 255

Asp Ala Gly Thr Tyr Val Asn Ile Pro Asp Arg Ser Gly Asp Thr Val
            260                 265                 270

Leu Ile Gly Ala Val Arg Gly Gly His Val Glu Ile Val Arg Ala Leu
        275                 280                 285

Leu Gln Lys Tyr Ala Asp Ile Asp Ile Arg Gly Gln Asp Asn Lys Thr
    290                 295                 300

Ala Leu Tyr Trp Ala Val Glu Lys Gly Asn Ala Thr Met Val Arg Asp

```
            305                 310                 315                 320
Ile Leu Gln Cys Asn Pro Asp Thr Glu Ile Cys Thr Lys Asp Gly Glu
                325                 330                 335

Thr Pro Leu Ile Lys Ala Thr Lys Met Arg Asn Ile Glu Val Val Glu
                340                 345                 350

Leu Leu Leu Asp Lys Gly Ala Lys Val Ser Ala Val Asp Lys Lys Gly
                355                 360                 365

Asp Thr Pro Leu His Ile Ala Ile Arg Gly Arg Ser Arg Lys Leu Ala
370                 375                 380

Glu Leu Leu Leu Arg Asn Pro Lys Asp Gly Arg Leu Leu Tyr Arg Pro
385                 390                 395                 400

Asn Lys Ala Gly Glu Thr Pro Tyr Asn Ile Asp Cys Ser His Gln Lys
                405                 410                 415

Ser Ile Leu Thr Gln Ile Phe Gly Ala Arg His Leu Ser Pro Thr Glu
                420                 425                 430

Thr Asp Gly Asp Met Leu Gly Tyr Asp Leu Tyr Ser Ser Ala Leu Ala
                435                 440                 445

Asp Ile Leu Ser Glu Pro Thr Met Gln Pro Pro Ile Cys Val Gly Leu
450                 455                 460

Tyr Ala Gln Trp Gly Ser Gly Lys Ser Phe Leu Leu Lys Lys Leu Glu
465                 470                 475                 480

Asp Glu Met Lys Thr Phe Ala Gly Gln Gln Ile Glu Pro Leu Phe Gln
                485                 490                 495

Phe Ser Trp Leu Ile Val Phe Leu Thr Leu Leu Leu Cys Gly Gly Leu
                500                 505                 510

Gly Leu Leu Phe Ala Phe Thr Val His Pro Asn Leu Gly Ile Ala Val
                515                 520                 525

Ser Leu Ser Phe Leu Ala Leu Leu Tyr Ile Phe Phe Ile Val Ile Tyr
                530                 535                 540

Phe Gly Gly Arg Arg Glu Gly Glu Ser Trp Asn Trp Ala Trp Val Leu
545                 550                 555                 560

Ser Thr Arg Leu Ala Arg His Ile Gly Tyr Leu Glu Leu Leu Leu Lys
                565                 570                 575

Leu Met Phe Val Asn Pro Pro Glu Leu Pro Glu Gln Thr Thr Lys Ala
                580                 585                 590

Leu Pro Val Arg Phe Leu Phe Thr Asp Tyr Asn Arg Leu Ser Ser Val
                595                 600                 605

Gly Gly Glu Thr Ser Leu Ala Glu Met Ile Ala Thr Leu Ser Asp Ala
                610                 615                 620

Cys Glu Arg Glu Phe Gly Phe Leu Ala Thr Arg Leu Phe Arg Val Phe
625                 630                 635                 640

Lys Thr Glu Asp Thr Gln Gly Lys Lys Lys Trp Lys Lys Thr Cys Cys
                645                 650                 655

Leu Pro Ser Phe Val Ile Phe Leu Phe Ile Ile Gly Cys Ile Ile Ser
                660                 665                 670

Gly Ile Thr Leu Leu Ala Ile Phe Arg Val Asp Pro Lys His Leu Thr
                675                 680                 685

Val Asn Ala Val Leu Ile Ser Ile Ala Ser Val Val Gly Leu Ala Phe
                690                 695                 700

Val Leu Asn Cys Arg Thr Trp Trp Gln Val Leu Asp Ser Leu Leu Asn
705                 710                 715                 720

Ser Gln Arg Lys Arg Leu His Asn Ala Ala Ser Lys Leu His Lys Leu
                725                 730                 735
```

-continued

```
Lys Ser Glu Gly Phe Met Lys Val Leu Lys Cys Glu Val Glu Leu Met
            740                 745                 750

Ala Arg Met Ala Lys Thr Ile Asp Ser Phe Thr Gln Asn Gln Thr Arg
            755                 760                 765

Leu Val Val Ile Ile Asp Gly Leu Asp Ala Cys Glu Gln Asp Lys Val
            770                 775             780

Leu Gln Met Leu Asp Thr Val Arg Val Leu Phe Ser Lys Gly Pro Phe
785             790                 795                 800

Ile Ala Ile Phe Ala Ser Asp Pro His Ile Ile Lys Ala Ile Asn
                805                 810             815

Gln Asn Leu Asn Ser Val Leu Arg Asp Ser Asn Ile Asn Gly His Asp
            820                 825                 830

Tyr Met Arg Asn Ile Val His Leu Pro Val Phe Leu Asn Ser Arg Gly
            835                 840                 845

Leu Ser Asn Ala Arg Lys Phe Leu Val Thr Ser Ala Thr Asn Gly Asp
            850                 855                 860

Val Pro Cys Ser Asp Thr Thr Gly Ile Gln Glu Asp Ala Asp Arg Arg
865             870                 875                 880

Val Ser Gln Asn Ser Leu Gly Glu Met Thr Lys Leu Gly Ser Lys Thr
                885                 890                 895

Ala Leu Asn Arg Arg Asp Thr Tyr Arg Arg Gln Met Gln Arg Thr
            900                 905                 910

Ile Thr Arg Gln Met Xaa Phe Asp Leu Thr Lys Leu Val Thr Glu
            915                 920                 925

Asp Trp Phe Ser Asp Ile Ser Pro Gln Thr Met Arg Arg Leu Leu Asn
            930                 935                 940

Ile Val Ser Val Thr Gly Arg Leu Leu Arg Ala Asn Gln Ile Ser Phe
945                 950                 955                 960

Asn Trp Asp Arg Leu Ala Ser Trp Ile Asn Leu Thr Glu Gln Trp Pro
                965                 970                 975

Tyr Arg Thr Ser Trp Leu Ile Leu Tyr Leu Glu Glu Thr Glu Gly Ile
            980                 985                 990

Pro Asp Gln Met Thr Leu Lys Thr Ile Tyr Glu Arg Ile Ser Lys Asn
            995                 1000                1005

Ile Pro Thr Thr Lys Asp Val Glu Pro Leu Leu Glu Ile Asp Gly
    1010                1015                1020

Asp Ile Arg Asn Phe Glu Val Phe Leu Ser Ser Arg Thr Pro Val
    1025                1030                1035

Leu Val Ala Arg Asp Val Lys Val Phe Leu Pro Cys Thr Val Asn
    1040                1045                1050

Leu Asp Pro Lys Leu Arg Glu Ile Ile Ala Asp Val Arg Ala Ala
    1055                1060                1065

Arg Glu Gln Ile Ser Ile Gly Gly Leu Ala Tyr Pro Pro Leu Pro
    1070                1075                1080

Leu His Glu Gly Pro Pro Arg Ala Pro Ser Gly Tyr Ser Gln Pro
    1085                1090                1095

Pro Ser Val Cys Ser Ser Thr Ser Phe Asn Gly Pro Phe Ala Gly
    1100                1105                1110

Gly Val Val Ser Pro Gln Pro His Ser Ser Tyr Tyr Ser Gly Met
    1115                1120                1125

Thr Gly Pro Gln His Pro Tyr Asn Arg Pro Phe Phe Ala Pro
    1130                1135                1140

Tyr Leu Tyr Thr Pro Arg Tyr Tyr Pro Gly Gly Ser Gln His Leu
    1145                1150                1155
```

```
Ile Ser Arg Pro Ser Val Lys Thr Ser Leu Pro Arg Asp Gln Asn
    1160                1165                1170

Asn Gly Leu Glu Val Ile Lys Glu Asp Ala Ala Glu Gly Leu Ser
    1175                1180                1185

Ser Pro Thr Asp Ser Ser Arg Gly Ser Gly Pro Ala Pro Gly Pro
    1190                1195                1200

Val Val Leu Leu Asn Ser Leu Asn Val Asp Ala Val Cys Glu Lys
    1205                1210                1215

Leu Lys Gln Ile Glu Gly Leu Asp Gln Ser Met Leu Pro Gln Tyr
    1220                1225                1230

Cys Thr Thr Ile Lys Lys Ala Asn Ile Asn Gly Arg Val Leu Ala
    1235                1240                1245

Gln Cys Asn Ile Asp Glu Leu Lys Lys Glu Met Asn Met Asn Phe
    1250                1255                1260

Gly Asp Trp His Leu Phe Arg Ser Thr Val Leu Glu Met Arg Asn
    1265                1270                1275

Ala Glu Ser His Val Val Pro Glu Asp Pro Arg Phe Leu Ser Glu
    1280                1285                1290

Ser Ser Ser Gly Pro Ala Pro His Gly Glu Pro Ala Arg Arg Ala
    1295                1300                1305

Ser His Asn Glu Leu Pro His Thr Glu Leu Ser Ser Gln Thr Pro
    1310                1315                1320

Tyr Thr Leu Asn Phe Ser Phe Glu Glu Leu Asn Thr Leu Gly Leu
    1325                1330                1335

Asp Glu Gly Ala Pro Arg His Ser Asn Leu Ser Trp Gln Ser Gln
    1340                1345                1350

Thr Arg Arg Thr Pro Ser Leu Ser Ser Leu Asn Ser Gln Asp Ser
    1355                1360                1365

Ser Ile Glu Ile Ser Lys Leu Thr Asp Lys Val Gln Ala Glu Tyr
    1370                1375                1380

Arg Asp Ala Tyr Arg Glu Tyr Ile Ala Gln Met Ser Gln Leu Glu
    1385                1390                1395

Gly Gly Pro Gly Ser Thr Thr Ile Ser Gly Arg Ser Ser Pro His
    1400                1405                1410

Ser Thr Tyr Tyr Met Gly Gln Ser Ser Ser Gly Gly Ser Ile His
    1415                1420                1425

Ser Asn Leu Glu Gln Glu Lys Gly Lys Asp Ser Glu Pro Lys Pro
    1430                1435                1440

Asp Asp Gly Arg Lys Ser Phe Leu Met Lys Arg Gly Asp Val Ile
    1445                1450                1455

Asp Tyr Ser Ser Ser Gly Val Ser Thr Asn Asp Ala Ser Pro Leu
    1460                1465                1470

Asp Pro Ile Thr Glu Glu Asp Glu Lys Ser Asp Gln Ser Gly Ser
    1475                1480                1485

Lys Leu Leu Pro Gly Lys Lys Ser Ser Glu Arg Ser Ser Leu Phe
    1490                1495                1500

Gln Thr Asp Leu Lys Leu Lys Gly Ser Gly Leu Arg Tyr Gln Lys
    1505                1510                1515

Leu Pro Ser Asp Glu Asp Glu Ser Gly Thr Glu Glu Ser Asp Asn
    1520                1525                1530

Thr Pro Leu Leu Lys Asp Asp Lys Asp Arg Lys Ala Glu Gly Lys
    1535                1540                1545

Val Glu Arg Val Pro Lys Ser Pro Glu His Ser Ala Glu Pro Ile
```

```
                1550            1555            1560

Arg Thr Phe Ile Lys Ala Lys Glu Tyr Leu Ser Asp Ala Leu Leu
    1565            1570            1575

Asp Lys Lys Asp Ser Ser Asp Ser Gly Val Arg Ser Ser Glu Ser
1580            1585            1590

Ser Pro Asn His Ser Leu His Asn Glu Val Ala Asp Asp Ser Gln
    1595            1600            1605

Leu Glu Lys Ala Asn Leu Ile Glu Leu Glu Asp Asp Ser His Ser
    1610            1615            1620

Gly Lys Arg Gly Ile Pro His Ser Leu Ser Gly Leu Gln Asp Pro
1625            1630            1635

Ile Ile Ala Arg Met Ser Ile Cys Ser Glu Asp Lys Lys Ser Pro
    1640            1645            1650

Ser Glu Cys Ser Leu Ile Ala Ser Ser Pro Glu Glu Asn Trp Pro
    1655            1660            1665

Ala Cys Gln Lys Ala Tyr Asn Leu Asn Arg Thr Pro Ser Thr Val
    1670            1675            1680

Thr Leu Asn Asn Asn Ser Ala Pro Ala Asn Arg Ala Asn Gln Asn
1685            1690            1695

Phe Asp Glu Met Glu Gly Ile Arg Glu Thr Ser Gln Val Ile Leu
    1700            1705            1710

Arg Pro Ser Ser Ser Pro Asn Pro Thr Thr Ile Gln Asn Glu Asn
    1715            1720            1725

Leu Lys Ser Met Thr His Lys Arg Ser Gln Arg Ser Ser Tyr Thr
    1730            1735            1740

Arg Leu Ser Lys Asp Pro Pro Glu Leu His Ala Ala Ala Ser Ser
    1745            1750            1755

Glu Ser Thr Gly Phe Gly Glu Glu Arg Glu Ser Ile Leu
    1760            1765            1770

<210> SEQ ID NO 124
<211> LENGTH: 801
<212> TYPE: PRT
<213> ORGANISM: mouse
<220> FEATURE:
<221> NAME/KEY: misc_feature
<222> LOCATION: (294)..(294)
<223> OTHER INFORMATION: Xaa can be any naturally occurring amino acid

<400> SEQUENCE: 124

Met Gly Asp Thr Val Val Glu Pro Ala Pro Leu Lys Pro Thr Ser Glu
1               5                   10                  15

Pro Thr Ser Gly Pro Pro Gly Asn Asn Gly Gly Ser Leu Leu Ser Val
            20                  25                  30

Ile Thr Glu Gly Val Gly Glu Leu Ser Val Ile Asp Pro Glu Val Ala
        35                  40                  45

Gln Lys Ala Cys Gln Glu Val Leu Glu Lys Val Lys Leu Leu His Gly
    50                  55                  60

Gly Val Ala Val Ser Ser Arg Gly Thr Pro Leu Glu Leu Val Asn Gly
65                  70                  75                  80

Asp Gly Val Asp Ser Glu Ile Arg Cys Leu Asp Asp Pro Pro Ala Gln
                85                  90                  95

Ile Arg Glu Glu Glu Asp Glu Met Gly Ala Ala Val Ala Ser Gly Thr
            100                 105                 110

Ala Lys Gly Ala Arg Arg Arg Gln Asn Asn Ser Ala Lys Gln Ser
        115                 120                 125
```

-continued

```
Trp Leu Leu Arg Leu Phe Glu Ser Lys Leu Phe Asp Ile Ser Met Ala
    130                 135                 140

Ile Ser Tyr Leu Tyr Asn Ser Lys Glu Pro Gly Val Gln Ala Tyr Ile
145                 150                 155                 160

Gly Asn Arg Leu Phe Cys Phe Arg Asn Glu Asp Val Asp Phe Tyr Leu
                165                 170                 175

Pro Gln Leu Leu Asn Met Tyr Ile His Met Asp Glu Asp Val Gly Asp
            180                 185                 190

Ala Ile Lys Pro Tyr Ile Val His Arg Cys Arg Gln Ser Ile Asn Phe
        195                 200                 205

Ser Leu Gln Cys Ala Leu Leu Leu Gly Ala Tyr Ser Ser Asp Met His
    210                 215                 220

Ile Ser Thr Gln Arg His Ser Arg Gly Thr Lys Leu Arg Lys Leu Ile
225                 230                 235                 240

Leu Ser Asp Glu Leu Lys Pro Ala His Arg Lys Arg Glu Leu Pro Ser
                245                 250                 255

Leu Ser Pro Ala Pro Asp Thr Gly Leu Ser Pro Ser Lys Arg Thr His
            260                 265                 270

Gln Arg Ser Lys Ser Asp Ala Thr Ala Ser Ile Ser Leu Ser Ser Asn
        275                 280                 285

Leu Lys Arg Thr Ala Xaa Asn Pro Lys Val Glu Asn Glu Asp Glu Pro
    290                 295                 300

Val Arg Leu Ala Pro Glu Arg Glu Phe Ile Lys Ser Leu Met Ala Ile
305                 310                 315                 320

Gly Lys Arg Leu Ala Thr Leu Pro Thr Lys Gln Lys Thr Gln Arg
                325                 330                 335

Leu Ile Ser Glu Leu Ser Leu Leu Asn His Lys Leu Pro Ala Arg Val
            340                 345                 350

Trp Leu Pro Thr Ala Gly Phe Asp His His Val Val Arg Val Pro His
        355                 360                 365

Thr Gln Ala Val Val Leu Asn Ser Lys Asp Lys Ala Pro Tyr Leu Ile
    370                 375                 380

Tyr Val Glu Val Leu Glu Cys Glu Asn Phe Asp Thr Thr Ser Val Pro
385                 390                 395                 400

Ala Arg Ile Pro Glu Asn Arg Ile Arg Ser Thr Arg Ser Val Glu Asn
                405                 410                 415

Leu Pro Glu Cys Gly Ile Thr His Glu Gln Arg Ala Gly Ser Phe Ser
            420                 425                 430

Thr Val Pro Asn Tyr Asp Asn Asp Glu Ala Trp Ser Val Asp Asp
        435                 440                 445

Ile Gly Glu Leu Gln Val Glu Leu Pro Glu Val His Thr Asn Ser Cys
    450                 455                 460

Asp Asn Ile Ser Gln Phe Ser Val Asp Ser Ile Thr Ser Gln Glu Ser
465                 470                 475                 480

Lys Glu Pro Val Phe Ile Ala Ala Gly Asp Ile Arg Arg Leu Ser
                485                 490                 495

Glu Gln Leu Ala His Thr Pro Thr Ala Phe Lys Arg Asp Pro Glu Asp
            500                 505                 510

Pro Ser Ala Val Ala Leu Lys Glu Pro Trp Gln Glu Lys Val Arg Arg
        515                 520                 525

Ile Arg Glu Gly Ser Pro Tyr Gly His Leu Pro Asn Trp Arg Leu Leu
    530                 535                 540

Ser Val Ile Val Lys Cys Gly Asp Asp Leu Arg Gln Glu Leu Leu Ala
545                 550                 555                 560
```

```
Phe Gln Val Leu Lys Gln Leu Gln Ser Ile Trp Glu Gln Glu Arg Val
                565                 570                 575

Pro Leu Trp Ile Lys Pro Tyr Lys Ile Leu Val Ile Ser Ala Asp Ser
            580                 585                 590

Gly Met Ile Glu Pro Val Val Asn Ala Val Ser Ile His Gln Val Lys
        595                 600                 605

Lys Gln Ser Gln Leu Ser Leu Leu Asp Tyr Phe Leu Gln Glu His Gly
    610                 615                 620

Ser Tyr Thr Thr Glu Ala Phe Leu Ser Ala Gln Arg Asn Phe Val Gln
625                 630                 635                 640

Ser Cys Ala Gly Tyr Cys Leu Val Cys Tyr Leu Leu Gln Val Lys Asp
                645                 650                 655

Arg His Asn Gly Asn Ile Leu Leu Asp Ala Glu Gly His Ile Ile His
            660                 665                 670

Ile Asp Phe Gly Phe Ile Leu Ser Ser Ser Pro Arg Asn Leu Gly Phe
        675                 680                 685

Glu Thr Ser Ala Phe Lys Leu Thr Thr Glu Phe Val Asp Val Met Gly
    690                 695                 700

Gly Leu Asp Gly Asp Met Phe Asn Tyr Tyr Lys Met Leu Met Leu Gln
705                 710                 715                 720

Gly Leu Ile Ala Ala Arg Lys His Met Asp Lys Val Val Gln Ile Val
                725                 730                 735

Glu Ile Met Gln Gln Gly Ser Gln Leu Pro Cys Phe His Gly Ser Ser
            740                 745                 750

Thr Ile Arg Asn Leu Lys Glu Arg Phe His Met Ser Met Thr Glu Glu
        755                 760                 765

Gln Leu Gln Leu Val Glu Gln Met Val Asp Gly Ser Met Arg Ser
    770                 775                 780

Ile Thr Thr Lys Leu Tyr Asp Gly Phe Gln Tyr Leu Thr Asn Gly Ile
785                 790                 795                 800

Met
```

<210> SEQ ID NO 125
<211> LENGTH: 415
<212> TYPE: PRT
<213> ORGANISM: human
<220> FEATURE:
<221> NAME/KEY: misc_feature
<222> LOCATION: (386)..(386)
<223> OTHER INFORMATION: Xaa can be any naturally occurring amino acid

<400> SEQUENCE: 125

```
Met Ser Ser Asn Cys Thr Ser Thr Thr Ala Val Ala Val Ala Pro Leu
1               5                   10                  15

Ser Ala Ser Lys Thr Lys Thr Lys Lys Lys His Phe Val Cys Gln Lys
            20                  25                  30

Val Lys Leu Phe Arg Ala Ser Glu Pro Ile Leu Ser Val Leu Met Trp
        35                  40                  45

Gly Val Asn His Thr Ile Asn Glu Leu Ser Asn Val Pro Val Pro Val
    50                  55                  60

Met Leu Met Pro Asp Asp Phe Lys Ala Tyr Ser Lys Ile Lys Val Asp
65                  70                  75                  80

Asn His Leu Phe Asn Lys Glu Asn Leu Pro Ser Arg Phe Lys Phe Lys
                85                  90                  95

Glu Tyr Cys Pro Met Val Phe Arg Asn Leu Arg Glu Arg Phe Gly Ile
            100                 105                 110
```

Asp Asp Gln Asp Tyr Gln Asn Ser Val Thr Arg Ser Ala Pro Ile Asn
            115                 120                 125

Ser Asp Ser Gln Gly Arg Cys Gly Thr Arg Phe Leu Thr Thr Tyr Asp
    130                 135                 140

Arg Arg Phe Val Ile Lys Thr Val Ser Ser Glu Asp Val Ala Glu Met
145                 150                 155                 160

His Asn Ile Leu Lys Lys Tyr His Gln Phe Ile Val Glu Cys His Gly
                165                 170                 175

Asn Thr Leu Leu Pro Gln Phe Leu Gly Met Tyr Arg Leu Thr Val Asp
            180                 185                 190

Gly Val Glu Thr Tyr Met Val Val Thr Arg Asn Val Phe Ser His Arg
        195                 200                 205

Leu Thr Val His Arg Lys Tyr Asp Leu Lys Gly Ser Thr Val Ala Arg
    210                 215                 220

Glu Ala Ser Asp Lys Glu Lys Ala Lys Asp Leu Pro Thr Phe Lys Asp
225                 230                 235                 240

Asn Asp Phe Leu Asn Glu Gly Gln Lys Leu His Val Gly Glu Glu Ser
                245                 250                 255

Lys Lys Asn Phe Leu Glu Lys Leu Lys Arg Asp Val Glu Phe Leu Ala
            260                 265                 270

Gln Leu Lys Ile Met Asp Tyr Ser Leu Leu Val Gly Ile His Asp Val
        275                 280                 285

Asp Arg Ala Glu Gln Glu Glu Met Glu Val Glu Glu Arg Ala Glu Asp
    290                 295                 300

Glu Glu Cys Glu Asn Asp Gly Val Gly Gly Asn Leu Leu Cys Ser Tyr
305                 310                 315                 320

Gly Thr Pro Pro Asp Ser Pro Gly Asn Leu Leu Ser Phe Pro Arg Phe
                325                 330                 335

Phe Gly Pro Gly Glu Phe Asp Pro Ser Val Asp Val Tyr Ala Met Lys
            340                 345                 350

Ser His Glu Ser Ser Pro Lys Lys Glu Val Tyr Phe Met Ala Ile Ile
        355                 360                 365

Asp Ile Leu Thr Pro Tyr Asp Thr Lys Lys Lys Ala Ala His Ala Ala
    370                 375                 380

Lys Xaa Val Lys His Gly Ala Gly Ala Glu Ile Ser Thr Val Asn Pro
385                 390                 395                 400

Glu Gln Tyr Ser Lys Arg Phe Asn Glu Phe Met Ser Asn Ile Leu
                405                 410                 415

<210> SEQ ID NO 126
<211> LENGTH: 416
<212> TYPE: PRT
<213> ORGANISM: mouse
<220> FEATURE:
<221> NAME/KEY: misc_feature
<222> LOCATION: (386)..(386)
<223> OTHER INFORMATION: Xaa can be any naturally occurring amino acid

<400> SEQUENCE: 126

Met Ser Ser Asn Cys Thr Ser Thr Thr Ala Val Ala Val Ala Pro Leu
1               5                   10                  15

Ser Ala Ser Lys Thr Lys Thr Lys Lys His Phe Val Cys Gln Lys
            20                  25                  30

Val Lys Leu Phe Arg Ala Ser Glu Pro Ile Leu Ser Val Leu Met Trp
        35                  40                  45

Gly Val Asn His Thr Ile Asn Glu Leu Ser Asn Val Pro Val Pro Val

```
                    50                  55                  60
Met Leu Met Pro Asp Asp Phe Lys Ala Tyr Ser Lys Ile Lys Val Asp
 65                  70                  75                  80

Asn His Leu Phe Asn Lys Glu Asn Leu Pro Ser Arg Phe Lys Phe Lys
                     85                  90                  95

Glu Tyr Cys Pro Met Val Phe Arg Asn Leu Arg Glu Arg Phe Gly Ile
                100                 105                 110

Asp Asp Gln Asp Tyr Gln Asn Ser Val Thr Arg Ser Ala Pro Ile Asn
                115                 120                 125

Ser Asp Ser Gln Gly Arg Cys Gly Thr Arg Phe Leu Thr Thr Tyr Asp
130                 135                 140

Arg Arg Phe Val Ile Lys Thr Val Ser Ser Glu Asp Val Ala Glu Met
145                 150                 155                 160

His Asn Ile Leu Lys Lys Tyr His Gln Phe Ile Val Glu Cys His Gly
                165                 170                 175

Asn Thr Leu Leu Pro Gln Phe Leu Gly Met Tyr Arg Leu Thr Val Asp
                180                 185                 190

Gly Val Glu Thr Tyr Met Val Val Thr Arg Asn Val Phe Ser His Arg
                195                 200                 205

Leu Thr Val His Arg Lys Tyr Asp Leu Lys Gly Ser Thr Val Ala Arg
210                 215                 220

Glu Ala Ser Asp Lys Glu Lys Ala Lys Asp Leu Pro Thr Phe Lys Asp
225                 230                 235                 240

Asn Asp Phe Leu Asn Glu Gly Gln Lys Leu His Val Gly Glu Glu Ser
                245                 250                 255

Lys Lys Asn Phe Leu Glu Lys Leu Lys Arg Asp Val Glu Phe Leu Ala
                260                 265                 270

Gln Leu Lys Ile Met Asp Tyr Ser Leu Leu Val Gly Ile His Asp Val
                275                 280                 285

Asp Arg Ala Glu Gln Glu Glu Met Glu Val Glu Arg Ala Glu Glu
290                 295                 300

Glu Glu Cys Glu Asn Asp Gly Val Gly Gly Ser Leu Leu Cys Ser Tyr
305                 310                 315                 320

Gly Thr Pro Pro Asp Ser Pro Gly Asn Leu Leu Ser Phe Pro Arg Phe
                325                 330                 335

Phe Gly Pro Gly Glu Phe Asp Pro Ser Val Asp Val Tyr Ala Met Lys
                340                 345                 350

Ser His Glu Ser Ala Pro Lys Lys Glu Val Tyr Phe Met Ala Ile Ile
                355                 360                 365

Asp Ile Leu Thr Pro Tyr Asp Ala Lys Lys Ala Ala His Ala Ala
370                 375                 380

Lys Xaa Val Lys His Gly Ala Gly Ala Glu Ile Ser Thr Val Asn Pro
385                 390                 395                 400

Glu Gln Tyr Ser Lys Arg Phe Asn Glu Phe Met Ser Asn Ile Leu Thr
                405                 410                 415

<210> SEQ ID NO 127
<211> LENGTH: 420
<212> TYPE: PRT
<213> ORGANISM: rat
<220> FEATURE:
<221> NAME/KEY: misc_feature
<222> LOCATION: (390)..(390)
<223> OTHER INFORMATION: Xaa can be any naturally occurring amino acid

<400> SEQUENCE: 127
```

-continued

```
Met Ala Ser Ser Val Pro Pro Ala Thr Ala Pro Ala Ala Ala Gly
1               5                   10                  15

Gly Pro Gly Pro Gly Phe Gly Phe Ala Ser Lys Thr Lys Lys His
                20                  25                  30

Phe Val Gln Gln Lys Val Lys Val Phe Arg Ala Ala Asp Pro Leu Val
        35                  40                  45

Gly Val Phe Leu Trp Gly Val Ala His Ser Ile Asn Glu Leu Ser Gln
50                      55                  60

Val Pro Pro Val Met Leu Leu Pro Asp Asp Phe Lys Ala Ser Ser
65                  70                  75                  80

Lys Ile Lys Val Asn Asn His Leu Phe His Arg Glu Asn Leu Pro Ser
                85                  90                  95

His Phe Lys Phe Lys Glu Tyr Cys Pro Gln Val Phe Arg Asn Leu Arg
            100                 105                 110

Asp Arg Phe Ala Ile Asp Asp His Asp Tyr Leu Val Ser Leu Thr Arg
            115                 120                 125

Ser Pro Pro Ser Glu Thr Glu Gly Ser Asp Gly Arg Phe Leu Ile Ser
        130                 135                 140

Tyr Asp Arg Thr Leu Val Ile Lys Glu Val Ser Ser Glu Asp Ile Ala
145                 150                 155                 160

Asp Met His Ser Asn Leu Ser Asn Tyr His Gln Tyr Ile Val Lys Cys
            165                 170                 175

His Gly Asn Thr Leu Leu Pro Gln Phe Leu Gly Met Tyr Arg Val Ser
            180                 185                 190

Val Glu Asn Glu Asp Ser Tyr Met Leu Val Met Arg Asn Met Phe Ser
        195                 200                 205

His Arg Leu Pro Val His Arg Lys Tyr Asp Leu Lys Gly Ser Leu Val
210                 215                 220

Ser Arg Glu Ala Ser Asp Lys Glu Lys Val Lys Glu Leu Pro Thr Leu
225                 230                 235                 240

Lys Asp Met Asp Phe Leu Asn Lys Asn Gln Lys Val Tyr Ile Gly Glu
            245                 250                 255

Glu Glu Lys Lys Val Phe Leu Gly Lys Leu Lys Arg Asp Val Glu Phe
        260                 265                 270

Leu Val Gln Leu Lys Ile Met Asp Tyr Ser Leu Leu Leu Gly Ile His
        275                 280                 285

Asp Ile Ile Arg Gly Ser Glu Pro Glu Glu Gly Pro Val Arg Glu
290                 295                 300

Glu Glu Ser Glu Trp Asp Gly Asp Cys Asn Leu Thr Gly Pro Pro Ala
305                 310                 315                 320

Leu Val Gly Ser Tyr Gly Thr Ser Pro Glu Gly Ile Gly Gly Tyr Ile
            325                 330                 335

His Ser His Arg Pro Leu Gly Pro Gly Glu Phe Glu Ser Phe Ile Asp
            340                 345                 350

Val Tyr Ala Ile Arg Ser Ala Glu Gly Ala Pro Glu Gly Gly Val Phe
        355                 360                 365

His Gly Leu Ile Asp Ile Leu Thr Gln Tyr Asp Ala Lys Lys Lys Ala
        370                 375                 380

Ala His Ala Ala Lys Xaa Val Lys His Gly Ala Gly Ala Glu Ile Ser
385                 390                 395                 400

Thr Val His Pro Glu Gln Tyr Ala Lys Arg Phe Leu Asp Phe Ile Ser
            405                 410                 415

Asn Ile Phe Ala
            420
```

<210> SEQ ID NO 128
<211> LENGTH: 783
<212> TYPE: PRT
<213> ORGANISM: human
<220> FEATURE:
<221> NAME/KEY: misc_feature
<222> LOCATION: (351)..(351)
<223> OTHER INFORMATION: Xaa can be any naturally occurring amino acid

<400> SEQUENCE: 128

```
Met Glu Ser Pro Gly Glu Ser Gly Ala Gly Ser Pro Gly Ala Pro Ser
1               5                   10                  15

Pro Ser Ser Phe Thr Thr Gly His Leu Ala Arg Glu Lys Pro Ala Gln
                20                  25                  30

Asp Pro Leu Tyr Asp Val Pro Asn Ala Ser Gly Gly Gln Ala Gly Gly
            35                  40                  45

Pro Gln Arg Pro Gly Arg Val Val Ser Leu Arg Glu Arg Leu Leu Leu
        50                  55                  60

Thr Arg Pro Val Trp Leu Gln Leu Gln Ala Asn Ala Ala Ala Ala Leu
65                  70                  75                  80

His Met Leu Arg Thr Glu Pro Pro Gly Thr Phe Leu Val Arg Lys Ser
                85                  90                  95

Asn Thr Arg Gln Cys Gln Ala Leu Cys Met Arg Leu Pro Glu Ala Ser
                100                 105                 110

Gly Pro Ser Phe Val Ser Ser His Tyr Ile Leu Glu Ser Pro Gly Gly
            115                 120                 125

Val Ser Leu Glu Gly Ser Glu Leu Met Phe Pro Asp Leu Val Gln Leu
        130                 135                 140

Ile Cys Ala Tyr Cys His Thr Arg Asp Ile Leu Leu Leu Pro Leu Gln
145                 150                 155                 160

Leu Pro Arg Ala Ile His His Ala Ala Thr His Lys Glu Leu Glu Ala
                165                 170                 175

Ile Ser His Leu Gly Ile Glu Phe Trp Ser Ser Ser Leu Asn Ile Lys
                180                 185                 190

Ala Gln Arg Gly Pro Ala Gly Gly Pro Val Leu Pro Gln Leu Lys Ala
            195                 200                 205

Arg Ser Pro Gln Glu Leu Asp Gln Gly Thr Gly Ala Ala Leu Cys Phe
        210                 215                 220

Phe Asn Pro Leu Phe Pro Gly Asp Leu Gly Pro Thr Lys Arg Glu Lys
225                 230                 235                 240

Phe Lys Arg Ser Phe Lys Val Arg Val Ser Thr Glu Thr Ser Ser Pro
                245                 250                 255

Leu Ser Pro Pro Ala Val Pro Pro Pro Val Pro Val Leu Pro Gly Gly
                260                 265                 270

Ala Val Pro Ser Gln Thr Glu Arg Leu Pro Pro Cys Gln Leu Leu Arg
            275                 280                 285

Arg Glu Ser Ser Val Gly Tyr Arg Val Pro Ala Gly Ser Gly Pro Ser
        290                 295                 300

Leu Pro Pro Met Pro Ser Leu Gln Glu Val Asp Cys Gly Ser Pro Ser
305                 310                 315                 320

Ser Ser Glu Glu Glu Gly Val Pro Gly Ser Arg Gly Ser Pro Ala Thr
                325                 330                 335

Ser Pro His Leu Gly Arg Arg Pro Leu Leu Arg Ser Met Xaa Ala
            340                 345                 350

Ala Phe Cys Ser Leu Leu Ala Pro Glu Arg Gln Val Gly Arg Ala Ala
```

```
               355                 360                 365
Ala Ala Leu Met Gln Asp Arg His Thr Ala Ala Gly Gln Leu Val Gln
    370                 375                 380

Asp Leu Leu Thr Gln Val Arg Ala Gly Pro Glu Pro Gln Glu Leu Gln
385                 390                 395                 400

Gly Ile Arg Gln Ala Leu Ser Arg Ala Arg Ala Met Leu Ser Ala Glu
                405                 410                 415

Leu Gly Pro Glu Lys Leu Leu Ser Pro Lys Arg Leu Glu His Val Leu
            420                 425                 430

Glu Lys Ser Leu His Cys Ser Val Leu Lys Pro Leu Arg Pro Ile Leu
        435                 440                 445

Ala Ala Arg Leu Arg Arg Leu Ala Ala Asp Gly Ser Leu Gly Arg
    450                 455                 460

Leu Ala Glu Gly Leu Arg Leu Ala Arg Ala Gln Gly Pro Gly Ala Phe
465                 470                 475                 480

Gly Ser His Leu Ser Leu Pro Ser Pro Val Glu Leu Glu Gln Val Arg
                485                 490                 495

Gln Lys Leu Leu Gln Leu Leu Arg Thr Tyr Ser Pro Ser Ala Gln Val
            500                 505                 510

Lys Arg Leu Leu Gln Ala Cys Lys Leu Leu Tyr Met Ala Leu Arg Thr
        515                 520                 525

Gln Glu Gly Glu Gly Ala Gly Ala Asp Glu Phe Leu Pro Leu Leu Ser
    530                 535                 540

Leu Val Leu Ala His Cys Asp Leu Pro Glu Leu Leu Leu Glu Ala Glu
545                 550                 555                 560

Tyr Met Ser Glu Leu Leu Glu Pro Ser Leu Leu Thr Gly Glu Gly Gly
                565                 570                 575

Tyr Tyr Leu Thr Ser Leu Ser Ala Ser Leu Ala Leu Leu Ser Gly Leu
            580                 585                 590

Gly Gln Ala His Thr Leu Pro Leu Ser Pro Val Gln Glu Leu Arg Arg
        595                 600                 605

Ser Leu Ser Leu Trp Glu Gln Arg Arg Leu Pro Ala Thr His Cys Phe
    610                 615                 620

Gln His Leu Leu Arg Val Ala Tyr Gln Asp Pro Ser Ser Gly Cys Thr
625                 630                 635                 640

Ser Lys Thr Leu Ala Val Pro Pro Glu Ala Ser Ile Ala Thr Leu Asn
                645                 650                 655

Gln Leu Cys Ala Thr Lys Phe Arg Val Thr Gln Pro Asn Thr Phe Gly
            660                 665                 670

Leu Phe Leu Tyr Lys Glu Gln Gly Tyr His Arg Leu Pro Pro Gly Ala
        675                 680                 685

Leu Ala His Arg Leu Pro Thr Thr Gly Tyr Leu Val Tyr Arg Arg Ala
    690                 695                 700

Glu Trp Pro Glu Thr Gln Gly Ala Val Thr Glu Glu Gly Ser Gly
705                 710                 715                 720

Gln Ser Glu Ala Arg Ser Arg Gly Glu Glu Gln Gly Cys Gln Gly Asp
                725                 730                 735

Gly Asp Ala Gly Val Lys Ala Ser Pro Arg Asp Ile Arg Glu Gln Ser
            740                 745                 750

Glu Thr Thr Ala Glu Gly Gly Gln Gly Gln Ala Gln Glu Gly Pro Ala
        755                 760                 765

Gln Pro Gly Glu Pro Glu Ala Glu Gly Ser Arg Ala Ala Glu Glu
    770                 775                 780
```

-continued

```
<210> SEQ ID NO 129
<211> LENGTH: 1210
<212> TYPE: PRT
<213> ORGANISM: human
<220> FEATURE:
<221> NAME/KEY: misc_feature
<222> LOCATION: (678)..(678)
<223> OTHER INFORMATION: Xaa can be any naturally occurring amino acid
<220> FEATURE:
<221> NAME/KEY: misc_feature
<222> LOCATION: (693)..(693)
<223> OTHER INFORMATION: Xaa can be any naturally occurring amino acid

<400> SEQUENCE: 129

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
```

-continued

```
                  340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
        370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
            660                 665                 670
Ile Val Arg Lys Arg Xaa Leu Arg Arg Leu Leu Gln Glu Arg Glu Leu
        675                 680                 685
Val Glu Pro Leu Xaa Pro Ser Gly Glu Ala Pro Asn Gln Ala Leu Leu
    690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
        755                 760                 765
```

```
Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
            805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
            885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185
```

Gly Ser Thr Ala Glu Asn Ala Glu Tyr Leu Arg Val Ala Pro Gln
    1190             1195                1200

Ser Ser Glu Phe Ile Gly Ala
    1205            1210

<210> SEQ ID NO 130
<211> LENGTH: 839
<212> TYPE: PRT
<213> ORGANISM: human
<220> FEATURE:
<221> NAME/KEY: misc_feature
<222> LOCATION: (117)..(117)
<223> OTHER INFORMATION: Xaa can be any naturally occurring amino acid

<400> SEQUENCE: 130

Met Lys Lys Trp Ser Ser Thr Asp Leu Gly Ala Ala Asp Pro Leu
1               5                   10                  15

Gln Lys Asp Thr Cys Pro Asp Pro Leu Asp Gly Asp Pro Asn Ser Arg
            20                  25                  30

Pro Pro Pro Ala Lys Pro Gln Leu Ser Thr Ala Lys Ser Arg Thr Arg
            35                  40                  45

Leu Phe Gly Lys Gly Asp Ser Glu Glu Ala Phe Pro Val Asp Cys Pro
50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
            100                 105                 110

Tyr Asp Arg Arg Xaa Ile Phe Glu Ala Val Ala Gln Asn Asn Cys Gln
            115                 120                 125

Asp Leu Glu Ser Leu Leu Leu Phe Leu Gln Lys Ser Lys Lys His Leu
130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
            180                 185                 190

Ala Ser Tyr Thr Asp Ser Tyr Tyr Lys Gly Gln Thr Ala Leu His Ile
            195                 200                 205

Ala Ile Glu Arg Arg Asn Met Ala Leu Val Thr Leu Leu Val Glu Asn
210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
            275                 280                 285

Leu His Ala Leu Val Glu Val Ala Asp Asn Thr Ala Asp Asn Thr Lys
            290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr

```
                        325                 330                 335
Pro Leu Ala Leu Ala Ala Gly Thr Gly Lys Ile Gly Val Leu Ala Tyr
                340                 345                 350
Ile Leu Gln Arg Glu Ile Gln Glu Pro Glu Cys Arg His Leu Ser Arg
                355                 360                 365
Lys Phe Thr Glu Trp Ala Tyr Gly Pro Val His Ser Ser Leu Tyr Asp
370                 375                 380
Leu Ser Cys Ile Asp Thr Cys Glu Lys Asn Ser Val Leu Glu Val Ile
385                 390                 395                 400
Ala Tyr Ser Ser Ser Glu Thr Pro Asn Arg His Asp Met Leu Leu Val
                405                 410                 415
Glu Pro Leu Asn Arg Leu Leu Gln Asp Lys Trp Asp Arg Phe Val Lys
                420                 425                 430
Arg Ile Phe Tyr Phe Asn Phe Leu Val Tyr Cys Leu Tyr Met Ile Ile
                435                 440                 445
Phe Thr Met Ala Ala Tyr Tyr Arg Pro Val Asp Gly Leu Pro Pro Phe
                450                 455                 460
Lys Met Glu Lys Thr Gly Asp Tyr Phe Arg Val Thr Gly Glu Ile Leu
465                 470                 475                 480
Ser Val Leu Gly Gly Val Tyr Phe Phe Phe Arg Gly Ile Gln Tyr Phe
                485                 490                 495
Leu Gln Arg Arg Pro Ser Met Lys Thr Leu Phe Val Asp Ser Tyr Ser
                500                 505                 510
Glu Met Leu Phe Phe Leu Gln Ser Leu Phe Met Leu Ala Thr Val Val
                515                 520                 525
Leu Tyr Phe Ser His Leu Lys Glu Tyr Val Ala Ser Met Val Phe Ser
                530                 535                 540
Leu Ala Leu Gly Trp Thr Asn Met Leu Tyr Tyr Thr Arg Gly Phe Gln
545                 550                 555                 560
Gln Met Gly Ile Tyr Ala Val Met Ile Glu Lys Met Ile Leu Arg Asp
                565                 570                 575
Leu Cys Arg Phe Met Phe Val Tyr Ile Val Phe Leu Phe Gly Phe Ser
                580                 585                 590
Thr Ala Val Val Thr Leu Ile Glu Asp Gly Lys Asn Asp Ser Leu Pro
                595                 600                 605
Ser Glu Ser Thr Ser His Arg Trp Arg Gly Pro Ala Cys Arg Pro Pro
                610                 615                 620
Asp Ser Ser Tyr Asn Ser Leu Tyr Ser Thr Cys Leu Glu Leu Phe Lys
625                 630                 635                 640
Phe Thr Ile Gly Met Gly Asp Leu Glu Phe Thr Glu Asn Tyr Asp Phe
                645                 650                 655
Lys Ala Val Phe Ile Ile Leu Leu Leu Ala Tyr Val Ile Leu Thr Tyr
                660                 665                 670
Ile Leu Leu Leu Asn Met Leu Ile Ala Leu Met Gly Glu Thr Val Asn
                675                 680                 685
Lys Ile Ala Gln Glu Ser Lys Asn Ile Trp Lys Leu Gln Arg Ala Ile
                690                 695                 700
Thr Ile Leu Asp Thr Glu Lys Ser Phe Leu Lys Cys Met Arg Lys Ala
705                 710                 715                 720
Phe Arg Ser Gly Lys Leu Leu Gln Val Gly Tyr Thr Pro Asp Gly Lys
                725                 730                 735
Asp Asp Tyr Arg Trp Cys Phe Arg Val Asp Glu Val Asn Trp Thr Thr
                740                 745                 750
```

-continued

```
Trp Asn Thr Asn Val Gly Ile Ile Asn Glu Asp Pro Gly Asn Cys Glu
        755                 760                 765

Gly Val Lys Arg Thr Leu Ser Phe Ser Leu Arg Ser Ser Arg Val Ser
    770                 775                 780

Gly Arg His Trp Lys Asn Phe Ala Leu Val Pro Leu Leu Arg Glu Ala
785                 790                 795                 800

Ser Ala Arg Asp Arg Gln Ser Ala Gln Pro Glu Glu Val Tyr Leu Arg
                805                 810                 815

Gln Phe Ser Gly Ser Leu Lys Pro Glu Asp Ala Glu Val Phe Lys Ser
                820                 825                 830

Pro Ala Ala Ser Gly Glu Lys
            835

<210> SEQ ID NO 131
<211> LENGTH: 878
<212> TYPE: PRT
<213> ORGANISM: human
<220> FEATURE:
<221> NAME/KEY: misc_feature
<222> LOCATION: (876)..(876)
<223> OTHER INFORMATION: Xaa can be any naturally occurring amino acid

<400> SEQUENCE: 131

Met Ala Thr Ala Pro Ser Tyr Pro Ala Gly Leu Pro Gly Ser Pro Gly
1               5                   10                  15

Pro Gly Ser Pro Pro Pro Gly Gly Leu Glu Leu Gln Ser Pro Pro
            20                  25                  30

Pro Leu Leu Pro Gln Ile Pro Ala Pro Gly Ser Gly Val Ser Phe His
        35                  40                  45

Ile Gln Ile Gly Leu Thr Arg Glu Phe Val Leu Leu Pro Ala Ala Ser
    50                  55                  60

Glu Leu Ala His Val Lys Gln Leu Ala Cys Ser Ile Val Asp Gln Lys
65                  70                  75                  80

Phe Pro Glu Cys Gly Phe Tyr Gly Leu Tyr Asp Lys Ile Leu Leu Phe
                85                  90                  95

Lys His Asp Pro Thr Ser Ala Asn Leu Leu Gln Leu Val Arg Ser Ser
            100                 105                 110

Gly Asp Ile Gln Glu Gly Asp Leu Val Glu Val Val Leu Ser Ala Ser
        115                 120                 125

Ala Thr Phe Glu Asp Phe Gln Ile Arg Pro His Ala Leu Thr Val His
    130                 135                 140

Ser Tyr Arg Ala Pro Ala Phe Cys Asp His Cys Gly Glu Met Leu Phe
145                 150                 155                 160

Gly Leu Val Arg Gln Gly Leu Lys Cys Asp Gly Cys Gly Leu Asn Tyr
                165                 170                 175

His Lys Arg Cys Ala Phe Ser Ile Pro Asn Asn Cys Ser Gly Ala Arg
            180                 185                 190

Lys Arg Arg Leu Ser Ser Thr Ser Leu Ala Ser Gly His Ser Val Arg
        195                 200                 205

Leu Gly Thr Ser Glu Ser Leu Pro Cys Thr Ala Glu Glu Leu Ser Arg
    210                 215                 220

Ser Thr Thr Glu Leu Leu Pro Arg Arg Pro Pro Ser Ser Ser Ser Ser
225                 230                 235                 240

Ser Ser Ala Ser Ser Tyr Thr Gly Arg Pro Ile Glu Leu Asp Lys Met
                245                 250                 255

Leu Leu Ser Lys Val Lys Val Pro His Thr Phe Leu Ile His Ser Tyr
            260                 265                 270
```

```
Thr Arg Pro Thr Val Cys Gln Ala Cys Lys Lys Leu Leu Lys Gly Leu
        275                 280                 285

Phe Arg Gln Gly Leu Gln Cys Lys Asp Cys Lys Phe Asn Cys His Lys
        290                 295                 300

Arg Cys Ala Thr Arg Val Pro Asn Asp Cys Leu Gly Glu Ala Leu Ile
305                 310                 315                 320

Asn Gly Asp Val Pro Met Glu Glu Ala Thr Asp Phe Ser Glu Ala Asp
                325                 330                 335

Lys Ser Ala Leu Met Asp Glu Ser Glu Asp Ser Gly Val Ile Pro Gly
                340                 345                 350

Ser His Ser Glu Asn Ala Leu His Ala Ser Glu Glu Glu Glu Gly Glu
        355                 360                 365

Gly Gly Lys Ala Gln Ser Ser Leu Gly Tyr Ile Pro Leu Met Arg Val
        370                 375                 380

Val Gln Ser Val Arg His Thr Thr Arg Lys Ser Ser Thr Thr Leu Arg
385                 390                 395                 400

Glu Gly Trp Val Val His Tyr Ser Asn Lys Asp Thr Leu Arg Lys Arg
                405                 410                 415

His Tyr Trp Arg Leu Asp Cys Lys Cys Ile Thr Leu Phe Gln Asn Asn
                420                 425                 430

Thr Thr Asn Arg Tyr Tyr Lys Glu Ile Pro Leu Ser Glu Ile Leu Thr
        435                 440                 445

Val Glu Ser Ala Gln Asn Phe Ser Leu Val Pro Pro Gly Thr Asn Pro
450                 455                 460

His Cys Phe Glu Ile Val Thr Ala Asn Ala Thr Tyr Phe Val Gly Glu
465                 470                 475                 480

Met Pro Gly Gly Thr Pro Gly Pro Ser Gln Gly Ala Glu Ala
                485                 490                 495

Ala Arg Gly Trp Glu Thr Ala Ile Arg Gln Ala Leu Met Pro Val Ile
                500                 505                 510

Leu Gln Asp Ala Pro Ser Ala Pro Gly His Ala Pro His Arg Gln Ala
        515                 520                 525

Ser Leu Ser Ile Ser Val Ser Asn Ser Gln Ile Gln Glu Asn Val Asp
        530                 535                 540

Ile Ala Thr Val Tyr Gln Ile Phe Pro Asp Glu Val Leu Gly Ser Gly
545                 550                 555                 560

Gln Phe Gly Val Val Tyr Gly Gly Lys His Arg Lys Thr Gly Arg Asp
                565                 570                 575

Val Ala Val Lys Val Ile Asp Lys Leu Arg Phe Pro Thr Lys Gln Glu
                580                 585                 590

Ser Gln Leu Arg Asn Glu Val Ala Ile Leu Gln Ser Leu Arg His Pro
        595                 600                 605

Gly Ile Val Asn Leu Glu Cys Met Phe Glu Thr Pro Glu Lys Val Phe
        610                 615                 620

Val Val Met Glu Lys Leu His Gly Asp Met Leu Glu Met Ile Leu Ser
625                 630                 635                 640

Ser Glu Lys Gly Arg Leu Pro Glu Arg Leu Thr Lys Phe Leu Ile Thr
                645                 650                 655

Gln Ile Leu Val Ala Leu Arg His Leu His Phe Lys Asn Ile Val His
                660                 665                 670

Cys Asp Leu Lys Pro Glu Asn Val Leu Leu Ala Ser Ala Asp Pro Phe
        675                 680                 685

Pro Gln Val Lys Leu Cys Asp Phe Gly Phe Ala Arg Ile Ile Gly Glu
```

```
                       690                 695                 700

Lys Ser Phe Arg Arg Ser Val Val Gly Thr Pro Ala Tyr Leu Ala Pro
705                     710                 715                 720

Glu Val Leu Leu Asn Gln Gly Tyr Asn Arg Ser Leu Asp Met Trp Ser
                    725                 730                 735

Val Gly Val Ile Met Tyr Val Ser Leu Ser Gly Thr Phe Pro Phe Asn
                740                 745                 750

Glu Asp Glu Asp Ile Asn Asp Gln Ile Gln Asn Ala Ala Phe Met Tyr
            755                 760                 765

Pro Ala Ser Pro Trp Ser His Ile Ser Ala Gly Ala Ile Asp Leu Ile
        770                 775                 780

Asn Asn Leu Leu Gln Val Lys Met Arg Lys Arg Tyr Ser Val Asp Lys
785                 790                 795                 800

Ser Leu Ser His Pro Trp Leu Gln Glu Tyr Gln Thr Trp Leu Asp Leu
                805                 810                 815

Arg Glu Leu Glu Gly Lys Met Gly Glu Arg Tyr Ile Thr His Glu Ser
                820                 825                 830

Asp Asp Ala Arg Trp Glu Gln Phe Ala Ala Glu His Pro Leu Pro Gly
            835                 840                 845

Ser Gly Leu Pro Thr Asp Arg Asp Leu Gly Gly Ala Cys Pro Pro Gln
        850                 855                 860

Asp His Asp Met Gln Gly Leu Ala Glu Arg Ile Xaa Val Leu
865                 870                 875

<210> SEQ ID NO 132
<211> LENGTH: 875
<212> TYPE: PRT
<213> ORGANISM: mouse
<220> FEATURE:
<221> NAME/KEY: misc_feature
<222> LOCATION: (873)..(873)
<223> OTHER INFORMATION: Xaa can be any naturally occurring amino acid

<400> SEQUENCE: 132

Met Ala Ala Pro Ser His Pro Ala Gly Leu Pro Gly Ser Pro Gly
1               5                   10                  15

Pro Gly Ser Pro Pro Pro Gly Gly Leu Asp Leu Gln Ser Pro Pro
                20                  25                  30

Pro Leu Leu Pro Gln Ile Pro Ala Pro Gly Ser Gly Val Ser Phe His
                35                  40                  45

Ile Gln Ile Gly Leu Thr Arg Glu Phe Val Leu Pro Ala Ala Ser
        50                  55                  60

Glu Leu Ala His Val Lys Gln Leu Ala Cys Ser Ile Val Asp Gln Lys
65                  70                  75                  80

Phe Pro Glu Cys Gly Phe Tyr Gly Leu Tyr Asp Lys Ile Leu Leu Phe
                85                  90                  95

Lys His Asp Pro Thr Ser Ala Asn Leu Leu Gln Leu Val Arg Ser Ala
                100                 105                 110

Ala Asp Ile Gln Glu Gly Asp Leu Val Glu Val Val Leu Ser Ala Ser
            115                 120                 125

Ala Thr Phe Glu Asp Phe Gln Ile Arg Pro His Ala Leu Thr Val His
        130                 135                 140

Ser Tyr Arg Ala Pro Ala Phe Cys Asp His Cys Gly Glu Met Leu Phe
145                 150                 155                 160

Gly Leu Val Arg Gln Gly Leu Lys Cys Asp Gly Cys Gly Leu Asn Tyr
                165                 170                 175
```

-continued

```
His Lys Arg Cys Ala Phe Ser Ile Pro Asn Asn Cys Ser Gly Ala Arg
            180                 185                 190

Lys Arg Arg Leu Ser Ser Thr Ser Leu Ala Ser Gly His Ser Val Arg
        195                 200                 205

Leu Gly Ser Ser Glu Ser Leu Pro Cys Thr Ala Glu Glu Leu Ser Arg
    210                 215                 220

Ser Thr Thr Asp Leu Leu Pro Arg Arg Pro Ser Ser Ser Ser Ser Ser
225                 230                 235                 240

Ser Ser Ser Ser Ser Phe Tyr Thr Gly Arg Pro Ile Glu Leu Asp Lys
                245                 250                 255

Met Leu Met Ser Lys Val Lys Val Pro His Thr Phe Leu Ile His Ser
            260                 265                 270

Tyr Thr Arg Pro Thr Val Cys Gln Ala Cys Lys Lys Leu Leu Lys Gly
        275                 280                 285

Leu Phe Arg Gln Gly Leu Gln Cys Lys Asp Cys Lys Phe Asn Cys His
    290                 295                 300

Lys Arg Cys Ala Thr Arg Val Pro Asn Asp Cys Leu Gly Glu Ala Leu
305                 310                 315                 320

Ile Asn Gly Asp Val Pro Met Glu Glu Ala Ala Asp Tyr Ser Glu Ala
                325                 330                 335

Asp Lys Ser Ser Ile Ser Asp Glu Leu Glu Asp Ser Gly Val Ile Pro
            340                 345                 350

Gly Ser His Ser Glu Ser Ala Leu His Ala Ser Glu Glu Glu Glu Gly
        355                 360                 365

Glu Gly His Lys Ala Gln Ser Ser Leu Gly Tyr Ile Pro Leu Met Arg
    370                 375                 380

Val Val Gln Ser Val Arg His Thr Thr Arg Lys Ser Ser Thr Thr Leu
385                 390                 395                 400

Arg Glu Gly Trp Val Val His Tyr Ser Asn Lys Asp Thr Leu Arg Lys
                405                 410                 415

Arg His Tyr Trp Arg Leu Asp Cys Lys Cys Ile Thr Leu Phe Gln Asn
            420                 425                 430

Asn Thr Thr Asn Arg Tyr Tyr Lys Glu Ile Pro Leu Ser Glu Ile Leu
        435                 440                 445

Ala Val Glu Pro Ala Gln Asn Phe Ser Leu Val Pro Pro Gly Thr Asn
    450                 455                 460

Pro His Cys Phe Glu Ile Ile Thr Ala Asn Val Thr Tyr Phe Val Gly
465                 470                 475                 480

Glu Thr Pro Gly Gly Ala Pro Gly Gly Pro Ser Gly Gln Gly Thr Glu
                485                 490                 495

Ala Val Arg Gly Trp Glu Thr Ala Ile Arg Gln Ala Leu Met Pro Val
            500                 505                 510

Ile Leu Gln Asp Ala Pro Ser Ala Pro Gly His Thr Pro His Arg Gln
        515                 520                 525

Ala Ser Leu Ser Ile Ser Val Ser Asn Ser Gln Ile Gln Glu Asn Val
    530                 535                 540

Asp Ile Ala Thr Val Tyr Gln Ile Phe Pro Asp Glu Val Leu Gly Ser
545                 550                 555                 560

Gly Gln Phe Gly Val Val Tyr Gly Gly Lys His Arg Lys Thr Gly Arg
                565                 570                 575

Asp Val Ala Val Lys Val Ile Asp Lys Leu Arg Phe Pro Thr Lys Gln
            580                 585                 590

Glu Ser Gln Leu Arg Asn Glu Val Ala Ile Leu Gln Ser Leu Arg His
        595                 600                 605
```

```
Pro Gly Ile Val Asn Leu Glu Cys Met Phe Glu Thr Pro Glu Lys Val
        610                 615                 620
Phe Val Val Met Glu Lys Leu His Gly Asp Met Leu Glu Met Ile Leu
625                 630                 635                 640
Ser Ser Glu Lys Gly Arg Leu Pro Glu Arg Leu Thr Lys Phe Leu Ile
                645                 650                 655
Thr Gln Ile Leu Val Ala Leu Arg His Leu His Phe Lys Asn Ile Val
                660                 665                 670
His Cys Asp Leu Lys Pro Glu Asn Val Leu Leu Ala Ser Ala Asp Pro
        675                 680                 685
Phe Pro Gln Val Lys Leu Cys Asp Phe Gly Phe Ala Arg Ile Ile Gly
        690                 695                 700
Glu Lys Ser Phe Arg Arg Ser Val Val Gly Thr Pro Ala Tyr Leu Ala
705                 710                 715                 720
Pro Glu Val Leu Leu Asn Gln Gly Tyr Asn Arg Ser Leu Asp Met Trp
                725                 730                 735
Ser Val Gly Val Ile Met Tyr Val Ser Leu Ser Gly Thr Phe Pro Phe
                740                 745                 750
Asn Glu Asp Glu Asp Ile Asn Asp Gln Ile Gln Asn Ala Ala Phe Met
            755                 760                 765
Tyr Pro Ala Ser Pro Trp Ser His Ile Ser Ser Gly Ala Ile Asp Leu
        770                 775                 780
Ile Asn Asn Leu Leu Gln Val Lys Met Arg Lys Arg Tyr Ser Val Asp
785                 790                 795                 800
Lys Ser Leu Ser His Pro Trp Leu Gln Glu Tyr Gln Thr Trp Leu Asp
                805                 810                 815
Leu Arg Glu Leu Glu Gly Lys Met Gly Glu Arg Tyr Ile Thr His Glu
                820                 825                 830
Ser Asp Asp Ala Arg Trp Asp Gln Phe Val Ala Glu Arg His Gly Thr
        835                 840                 845
Pro Ala Glu Gly Asp Leu Gly Gly Ala Cys Leu Pro Gln Asp His Glu
        850                 855                 860
Met Gln Gly Leu Ala Glu Arg Ile Xaa Ile Leu
865                 870                 875
```

PKD LIGANDS AND POLYNUCLEOTIDES ENCODING PKD LIGANDS

This application is the U.S. national stage of International Application No. PCT/US2006/060062, filed Oct. 18, 2006, which claims the benefit of U.S. provisional Application No. 60/728,259, filed Oct. 19, 2005.

Reference To Sequence Listing Submitted Electronically Via EFS-Web

This application includes a "sequencelisting ascii.txt", 159,159 bytes, created on Jul. 20, 2011, and submitted electronically via EFS-Web, which is hereby incorporated by reference in its entirety.

FIELD OF INVENTION

The invention relates to mammalian kinase ligands, substrates and modulators. In particular, the invention relates to polypeptides, polypeptide compositions and polynucleotides that encode polypeptides that are ligands, substrates, and/or modulators of PKD. The invention also relates to polyligands that are homopolyligands or heteropolyligands that modulate PKD activity. The invention also relates to ligands and polyligands tethered to a subcellular location.

This application has subject matter related to application Ser. No. 10/724,532 (now U.S. Pat. No. 7,071,295), Ser. No. 10/682,764 (US2004/0185556, PCT/US2004/013517, WO2005/040336), Ser. No. 11/233,246, and US20040572011P (WO2005116231). Each of these patents and applications is hereby incorporated by reference.

BACKGROUND AND PRIOR ART

Kinases are enzymes that catalyze the addition of phosphate to a molecule. The addition of phosphate by a kinase is called phosphorylation. When the kinase substrate is a protein molecule, the amino acids commonly phosphorylated are serine, threonine and tyrosine. Phosphatases are enzymes that remove phosphate from a molecule. The removal of phosphate is called dephosphorylation. Kinases and phosphatases often represent competing forces within a cell to transmit, attenuate, or otherwise modulate cellular signals and cellular control mechanisms. Kinases and phosphatases have both overlapping and unique natural substrates. Cellular signals and control mechanisms, as regulated by kinases, phosphatases, and their natural substrates are a target of research tool design and drug design.

Mammalian Protein Kinase D is also known as PKD. The enzymatic activity, activation and autoregulation of PKD have been studied. Several cellular substrates of PKD have been identified. Substrates and modified substrates are generically referred to herein as ligands. Natural and synthetic peptide ligands have been studied to examine PKD substrate specificity. While peptide ligands and variants thereof have been studied as individuals PKD ligands, mixed ligands linked together as polyligands have not been demonstrated before this invention.

Design and synthesis of polypeptide ligands that modulate calcium/calmodulin-dependent protein kinase and that localize to the cardiac sarco(endo)plasmic reticulum was performed by Ji et al. (J Biol Chem (2003) 278:25063-71). Ji et al. accomplished this by generating expression constructs that localized calcium/calmodulin-dependent protein kinase inhibitory polypeptide ligands to the sarcoplasmic reticulum by fusing a sarcoplasmic reticulum localization signal derived from phospholamban to a polypeptide ligand. See also U.S. Pat. No. 7,071,295.

DETAILED DESCRIPTION OF POLYPEPTIDE AND POLYNUCLEOTIDE SEQUENCES

SEQ ID NOS:1-104 represent examples of monomeric peptide ligand sequences.

Specifically, SEQ ID NOS:1-52 are fragments of natural substrates of mammlain PKD, wherein each fragment contains at least one amino acid residue phosphorylatable by PKD. SEQ ID NOS:53-104 are fragments of natural PKD substrates, where the location of the PKD phosphorylatable serine or threonine in the natural polypeptide is designated as Xaa.

SEQ ID NOS:105-116 are example polyligands and polynucleotides encoding them.

Specifically, SEQ ID NO:105 is encoded by SEQ ID NO:106, SEQ ID NO:107 and by SEQ ID NO:108, wherein the the codons of SEQ ID NO:107 and SEQ ID NO:108 have been optimized for vector insertion. SEQ ID NO:108 includes flanking restriction sites. SEQ ID NO:105 is an embodiment of a polyligand of the structure X-S1-Y-S2-Z, wherein X is SEQ ID NO:53, Y is SEQ ID NO:55, Z is SEQ ID NO:58, wherein Xaa is alanine, and wherein S1 is a four amino acid spacer of the amino acid sequence AGAG and S2 is a four amino acid spacer of amino acid sequence GAGA. A polyligand of structure A-S1-B-S2-C is called herein a heteropolyligand, shown generically in FIG. 4B.

SEQ ID NO:109 is an embodiment of a polyligand of the structure X-S1-Y-S2-Z, wherein X is SEQ ID NO:61, Y is SEQ ID NO:65, Z is SEQ ID NO:66, wherein Xaa is alanine, wherein S1 is a four amino acid spacer of amino acid sequence AGAG and S2 is a four amino acid spacer of amino acid sequence GAGA. The PKD polyligand of SEQ ID NO:109 is encoded by SEQ ID NO:110, SEQ ID NO:111 and by SEQ ID NO:112, wherein the the codons of SEQ ID NO:111 and SEQ ID NO:112 have been optimized for vector insertion. SEQ ID NO:112 includes flanking restriction sites. A polyligand of structure X-S1-Y-S2-Z is also called herein a heteropolyligand, shown generically in FIG. 4B.

SEQ ID NO:113 is an embodiment of a polyligand of the structure X-Y-S3-Y-X, wherein X is SEQ ID NO:53, Y is SEQ ID NO:54, wherein Xaa is alanine, and wherein S3 is a five amino acid spacer with the sequence PAGAG. The PKD polyligand of SEQ ID NO :113 is encoded by SEQ ID NO:114, SEQ ID NO:115, and by SEQ ID NO:116, wherein the the codons of SEQ ID NO:115 and SEQ ID NO:116 have been optimized for vector insertion. SEQ ID NO:116 includes flanking restriction sites. A polyligand of structure X-Y-S3-Y-X is also called herein a heteropolyligand, shown generically in FIG. 4C.

SEQ ID NOS:117-132 are full length PKD substrates. These sequences have the following public database accession numbers: AAH64840, NP000354, CAA79356, NP001015053, NP009112, NP001531, NP065789, AAH00029, AAB48596, NP_536728, AAH47282, NP004283, NP005219,CAB95729,NP_057541, NP_849231. Each of the protein sequences represented by these accession numbers is incorporated by reference herein. In SEQ ID NOS:117-132, the positions of the amino acid(s) phosphorylatable by PKD are represented by Xaa. In wild-type proteins, Xaa is serine or threonine. In the ligands of the invention, Xaa is any amino acid.

Amino acid sequences containing Xaa encompass polypeptides where Xaa is any amino acid.

DETAILED DESCRIPTION OF DRAWINGS

FIGS. 1A-1C show examples of homopolymeric ligands without spacers.

FIGS. 2A-2C show examples of homopolymeric ligands with spacers.

FIGS. 3A-3C show examples of heteropolymeric ligands without spacers.

FIGS. 4A-4C show examples of heteropolymeric ligands with spacers.

FIGS. 5A-5G show examples of ligands and polymeric ligands linked to an optional epitope tag.

FIGS. 6A-6G show examples of ligands and polymeric ligands linked to an optional reporter.

FIGS. 7A-7G show examples of ligands and polymeric ligands linked to an optional localization signal.

FIGS. 8A-8G show examples of ligands and polymeric ligands linked to an optional localization signal and an optional epitope tag.

FIGS. 9A-9G show examples of gene constructs where ligands and polyligands are linked to an optional localization signal, an optional epitope tag, and an optional reporter.

BRIEF DESCRIPTION OF THE INVENTION

Figure 10A:
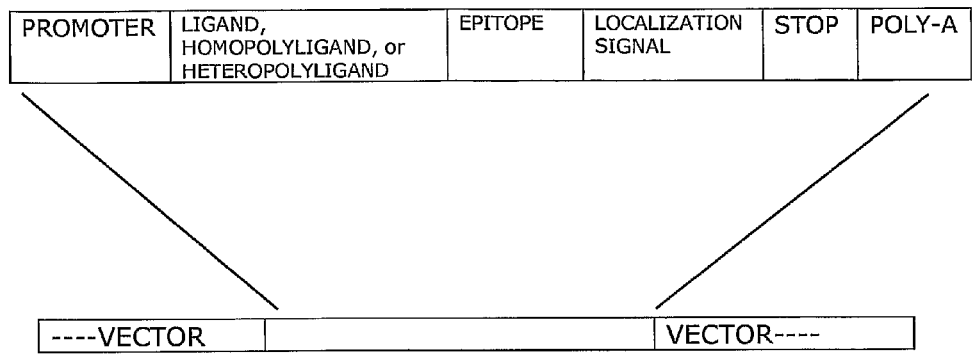
FIGS. 10A-10D show examples of vectors containing ligand gene constructs.

The invention relates to polypeptide ligands and polyligands for PKD. Various embodiments of the PKD ligands and polyligands are represented in SEQ ID NOS:1-132. More specifically, the invention relates to ligands, homopolyligands, and heteropolyligands that comprise any one or more of SEQ ID NOS:1-104. Additionally, the invention relates to ligands and polyligands comprising one or more subsequences of SEQ ID NOS:117-132 or any portion thereof. Furthermore, the invention relates to polyligands with at least about 80%, 85%, 90%, 95%, 96%, 97%, 98% and 99% sequence identity to a polyligand comprising one or more of SEQ ID NOS:1-104 or any portion thereof. Furthermore, the invention relates to polyligands with at least about 80%, 85%, 90%, 95%, 96%, 97%, 98% and 99% sequence identity to a polyligand comprising one or more subsequences of SEQ ID NOS:117-132 or portions thereof.

Polyligands, which can be homopolyligands or heteropolyligands, are chimeric ligands composed of two or more monomeric polypeptide ligands. An example of a monomeric ligand is the polypeptide represented by SEQ ID NO:61, wherein Xaa is any amino acid. An example of a homopolyligand is a polypeptide comprising a dimer or multimer of SEQ ID NO:61, wherein Xaa is any amino acid. An example of a heteropolyligand is a polypeptide comprising SEQ ID NO:1 and one or more of SEQ ID NOS:2-104, wherein Xaa is any amino acid. There are numerous ways to combine SEQ ID NOS:1-104 into homopolymeric or heteropolymeric ligands. Furthermore, there are numerous ways to combine portions or subsequences of SEQ ID NOS:117-132 with each other and with SEQ ID NOS:1-104 to make polymeric ligands that modulate PKD.

The polyligands of the invention optionally comprise spacer amino acids before, after, or between monomers. SEQ ID NO:105 is an embodiment of a polyligand of the structure X-S1-Y-S2-Z, wherein X is SEQ ID NO:53, Y is SEQ ID NO:55, Z is SEQ ID NO:58, wherein Xaa is alanine, and wherein S1 and S2 are four amino acid spacers. This invention intends to capture all combinations of homopolyligands and heteropolyligands without limitation to the examples given above or below. In this description, use of the term "ligand(s)" encompasses monomeric ligands, polymeric ligands, homopolymeric ligands and/or heteropolymeric ligands.

A monomeric ligand is a polypeptide where at least a portion of the polypeptide is capable of being recognized by PKD. The portion of the polypeptide capable of recognition is termed the recognition motif. In the present invention, recognition motifs can be natural or synthetic. Examples of recognition motifs are well known in the art and include, but are not limited to, naturally occurring PKD substrates and pseudosubstrate motifs.

A polymeric ligand comprises two or more monomeric ligands.

A homopolymeric ligand is a polymeric ligand where each of the monomeric ligands is identical in amino acid sequence, except that a phosphorylatable residue may be substituted or modified in one or more of the monomeric ligands.

A heteropolymeric ligand is a polymeric ligand where some of the monomeric ligands do not have an identical amino acid sequence.

The ligands of the invention are optionally linked to additional molecules or amino acids that provide an epitope tag, a reporter, and/or a cellular localization signal. The cellular localization signal targets the ligands to a region of a cell. The epitope tag and/or reporter and/or localization signal may be the same molecule. The epitope tag and/or reporter and/or localization signal may also be different molecules.

The invention also encompasses polynucleotides comprising a nucleotide sequence encoding ligands, homopolyligands, and heteropolyligands. The nucleic acids of the invention are optionally linked to additional nucleotide sequences encoding polypeptides with additional features, such as an epitope tag, a reporter, and/or a cellular localization signal. The polynucleotides are optionally flanked by nucleotide sequences comprising restriction endonuclease sites and other nucleotides needed for restriction endonuclese activity. The flanking sequences optionally provide unique cloning sites within a vector and optionally provide directionality of subsequence cloning. Further, the nucleic acids of the invention are optionally incorporated into vector polynucleotides. The ligands, polyligands, and polynucleotides of this invention have utility as research tools and/or therapeutics.

DETAILED DESCRIPTION OF THE INVENTION

The present invention relates to ligands and polyligands that are PKD modulators. Various embodiments of ligands and polyligands are represented in SEQ ID NOS:1-132. Polyligands are chimeric ligands comprising two or more monomeric polypeptide ligands. An example of a monomeric ligand is the polypeptide represented by SEQ ID NO:54, wherein Xaa is any amino acid. Another example of a monomeric ligand is the polypeptide represented by SEQ ID NO:1. Each of SEQ ID NOS:1-104 represents an individual polypeptide ligand in monomeric form, wherein Xaa is any amino acid. Additional examples of monomeric ligands are subsequence portions of SEQ ID NOS:117-132 containing a PKD recognition motif. Monomeric ligand subsequences of SEQ ID NOS:117-132 may be wild-type subsequences. Additionally, monomeric ligand subsequences of SEQ ID NOS:117-132 may have the PKD phosphorylatable amino acids replaced by other amino acids. Furthermore, monomeric ligands and polyligands may have at least about 80%, 85%, 90%, 95%, 96%, 97%, 98% or 99% sequence identity to a ligand comprising an amino acid sequence in one or more of SEQ ID NOS:1-104. Furthermore, monomeric ligands and polyligands may have at least about 80%, 85%, 90%, 95%, 96%, 97%, 98% and 99% sequence identity to a subsequence of SEQ ID NOS:117-132.

An example of a homopolyligand is a polypeptide comprising a dimer or multimer of SEQ ID NO:66, wherein Xaa is any amino acid. An example of a heteropolyligand is a polypeptide comprising SEQ ID NO:104 and one or more of SEQ ID NOS:1-103, wherein Xaa is any amino acid. There are numerous ways to combine SEQ ID NOS:1-104 into homopolymeric or heteropolymeric ligands. Furthermore, there are numerous ways to combine PKD recogntition motif-containing portions of SEQ ID NOS:117-132 with each other and with SEQ ID NOS:1-104 to make polymeric ligands.

Polyligands may comprise any two or more of a sequence selected from SEQ ID NOS:1-104 and recognition motif-containing portions of SEQ ID NOS:117-132, wherein Xaa is any amino acid. A dimer or multimer of SEQ ID NO:91 is an example of a homopolyligand. An example of a heteropolyligand is a polypeptide comprising SEQ ID NO:5 and one or more of a recognition motif-containing portion of SEQ ID NOS:117-132. There are numerous ways to combine SEQ ID NOS:1-104 and portions of SEQ ID NOS:117-132 into homopolymeric or heteropolymeric ligands. The instant invention is directed to all possible combinations of homopolyligands and heteropolyligands without limitation.

SEQ ID NOS:53-104 and SEQ ID NOS:117-132 show polypeptides that contain at least one serine or threonine residue phosphorylatable by PKD, the positions of which are represented by Xaa. In nature, Xaa is, generally speaking, serine or threonine. In one embodiment of the instant invention, Xaa can be any amino acid. Ligands where Xaa is serine or threonine can be used as part of a polyligand, however in one embodiment, at least one phosphorylatable serine or threonine is replaced with another amino acid, such as one of the naturally occurring amino acids including, alanine, aspartate, asparagine, cysteine, glutamate, glutamine, phenylalanine, glycine, histidine, isoleucine, leucine, lysine, methionine, proline, arginine, valine, tryptophan, or tyrosine. The Xaa may also be a non-naturally occurring amino acid. In another embodiment, the PKD phosphorylatable serine(s) or threonine(s) are replaced by alanine. The ligands and polyligands of the invention are designed to modulate the endogenous effects of PKD.

In general, ligand monomers based on natural PKD substrates are built by isolating a putative PKD phosphorylation recognition motif in a PKD substrate. Sometimes it is desirable to modify the phosphorylatable residue to an amino acid other than serine or threonine. Additional monomers include the PKD recognition motif as well as amino acids adjacent and contiguous on either side of the PKD recognition motif. Monomeric ligands may therefore be any length provided the monomer includes the PKD recognition motif. For example, the monomer may comprise a PKD recognition motif and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30-100 or more amino acids adjacent to the recognition motif.

For example, in one embodiment, the invention comprises an inhibitor of PKD comprising at least one copy of a peptide selected from the group consisting of:
a) a peptide at least 80% identical to a peptide comprising amino acid residues corresponding to amino acid residues 194-201 of SEQ ID NO:117, wherein the amino acid residue corresponding to amino acid residue 199 of SEQ ID NO:117 is an amino acid residue other than serine or threonine;
b) a peptide at least 80% identical to a peptide comprising amino acid residues corresponding to amino acid residues 191-203 of SEQ ID NO:117, wherein the amino acid residue corresponding to amino acid residue 199 of SEQ ID NO:117 is an amino acid residue other than serine or threonine;
c) a peptide at least 80% identical to a peptide comprising amino acid residues corresponding to amino acid residues 189-205 of SEQ ID NO:117, wherein the amino acid residue corresponding to amino acid residue 199 of SEQ ID NO:117 is an amino acid residue other than serine or threonine; and
d) a peptide at least 80% identical to a peptide comprising amino acid residues corresponding to amino acid residues 184-207 of SEQ ID NO:117, wherein the amino acid residue corresponding to amino acid residue 199 of SEQ ID NO:117 is an amino acid residue other than serine or threonine.

As used herein, the terms "correspond(s) to" and "corresponding to," as they relate to sequence alignment, are intended to mean enumerated positions within a reference protein, e.g., HDAC5 (SEQ ID NO:119), and those positions that align with the positions on the reference protein. Thus, when the amino acid sequence of a subject peptide is aligned with the amino acid sequence of a reference peptide, e.g., SEQ ID NO:119, the amino acids in the subject peptide sequence that "correspond to" certain enumerated positions of the reference peptide sequence are those that align with these positions of the reference peptide sequence, but are not necessarily in these exact numerical positions of the reference sequence. Methods for aligning sequences for determining corresponding amino acids between sequences are described below.

Additional embodiments of the invention include monomers (as described above) based on any putative or real substrate for PKD, such as substrates identified by SEQ ID NOS: 1-104 and SEQ ID NOS:117-132. Furthermore, if the substrate has more than one recognition motif, then more than one monomer may be identified therein.

Another embodiment of the invention is a nucleic acid molecule comprising a polynucleotide sequence encoding at least one copy of a ligand peptide.

Another embodiment of the invention is a nucleic acid molecule wherein the polynucleotide sequence encodes one or more copies of one or more peptide ligands.

Another embodiment of the invention is a nucleic acid molecule wherein the polynucleotide sequence encodes at least a number of copies of the peptide selected from the group consisting of 2, 3, 4, 5, 6, 7, 8, 9 or 10.

Another embodiment of the invention is a vector comprising a nucleic acid molecule encoding at least one copy of a ligand or polyligand.

Another embodiment of the invention is a recombinant host cell comprising a vector comprising a nucleic acid molecule encoding at least one copy of a ligand or polyligand.

Another embodiment of the invention is a method of inhibiting PKD in a cell comprising transfecting a vector comprising a nucleic acid molecule encoding at least one copy of a ligand or polyligand into a host cell and culturing the transfected host cell under conditions suitable to produce at least one copy of the ligand or polyligand.

The invention also relates to modified inhibitors that are at least about 80%, 85%, 90% 95%, 96%, 97%, 98% or 99% identical to a reference inhibitor. A "modified inhibitor" is used to mean a peptide that can be created by addition, deletion or substitution of one or more amino acids in the primary structure (amino acid sequence) of a inhibitor protein or polypeptide. A "modified recognition motif" is a naturally occurring PKD recognition motif that has been modified by addition, deletion, or substitution of one or more amino acids in the primary structure (amino acid sequence) of the motif. For example, a modified PKD recognition motif may be a motif where the phosphorylatable amino acid has been modified to a non-phosphorylatable amino acid. The terms "protein" and "polypeptide" are used interchangeably herein. The reference inhibitor is not necessarily a wild-type protein or a portion thereof. Thus, the reference inhibitor may be a protein or peptide whose sequence was previously modified over a wild-type protein. The reference inhibitor may or may not be the wild-type protein from a particular organism.

A polypeptide having an amino acid sequence at least, for example, about 95% "identical" to a reference an amino acid sequence is understood to mean that the amino acid sequence of the polypeptide is identical to the reference sequence except that the amino acid sequence may include up to about five modifications per each 100 amino acids of the reference amino acid sequence encoding the reference peptide. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exist several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at both ends, relative to the query sequence, the percent identity is corrected by calculating the number of amino acids of the query sequence that are N-and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N-or C-termini of the reference or subject sequence, respectively, may be considered for the purposes of manually adjusting the percent identity score. That is, residues that are not matched/aligned with the N-or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N-and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N-or C-termini of the subject sequence which are not matched/aligned with the query. In this case the percent identity calculated by FASTDB is not manually corrected.

The polyligands of the invention optionally comprise spacer amino acids before, after, or between monomers. The length and composition of the spacer may vary. An example of a spacer is glycine, alanine, polyglycine, or polyalanine. Specific examples of spacers used between monomers in SEQ ID NO:105 are the four amino acids AGAG, and the four amino acids GAGA. Spacer amino acids may be any amino acid and are not limited to alanine and glycine. The instant invention is directed to all combinations of homopolyligands and heteropolyligands, with or without spacers, and without limitation to the examples given above or below.

The ligands and polyligands of the invention are optionally linked to additional molecules or amino acids that provide an epitope tag, a reporter, and/or localize the ligand to a region of a cell (See FIGS. 5A-5G, FIGS. 6A-6G, FIGS. 7A-7G, and FIGS. 8A-8G). Non-limiting examples of epitope tags are FLAG (Kodak; Rochester, N.Y.), HA (hemagluttinin), c-Myc and His6. Additional examples of epitope tags are given in Jarvik & Telmer 1998 Annual Reviw of Genetics 32:601-18. Non-limiting examples of reporters are alkaline phosphatase, galactosidase, peroxidase, luciferase and green fluorescent protein (GFP). Non-limiting examples of cellular localizations are sarcoplamic reticulum, endoplasmic reticulum, mitochondria, golgi apparatus, nucleus, plasma membrane, apical membrane, and basolateral membrane. The epitopes, reporters and localization signals are given by way of example and without limitation. The epitope tag, reporter and/or localization signal may be the same molecule. The epitope tag, reporter and/or localization signal may also be different molecules.

Ligands and polyligands and optional amino acids linked thereto can be synthesized chemically or recombinantly using techniques known in the art. Chemical synthesis techniques include but are not limited to peptide synthesis which is often performed using an automated peptide synthesizer. Pepetides can also be synthesized utilizing non-automated peptide sythesis methods known in the art. Recombinant techniques include insertion of ligand-encoding nucleic acids into expression vectors, wherein nucleic acid expression products are synthesized using cellular factors and processes.

Linkage of a cellular localization signal, epitope tag, or reporter to a ligand or polyligand can include covalent or enzymatic linkage to the ligand. When the localization signal comprises material other than a polypeptide, such as a lipid or carbohydrate, a chemical reaction to link molecules may be utilized. Additionally, non-standard amino acids and amino acids modified with lipids, carbohydrates, phosphate or other molecules may be used as precursors to peptide synthesis. The ligands of the invention have therapeutic utility with or without localization signals. However, ligands linked to localization signals have utility as subcellular tools or therapeutics. For example, ligands depicted generically in FIGS. 7A-7G and FIGS. 8A-8G represent ligands with utility as subcellular tools or therapeutics. PKD ligand-containing gene constructs are also delivered via gene therapy. FIGS. 10B and 10C depict embodiments of gene therapy vectors for delivering and controlling polypeptide expression in vivo. Polynucleotide sequences linked to the gene construct in FIGS. 10B and 10C include genome integration domains to facilitate integration of the transgene into a viral genome and/or host genome.

Figure 10B:
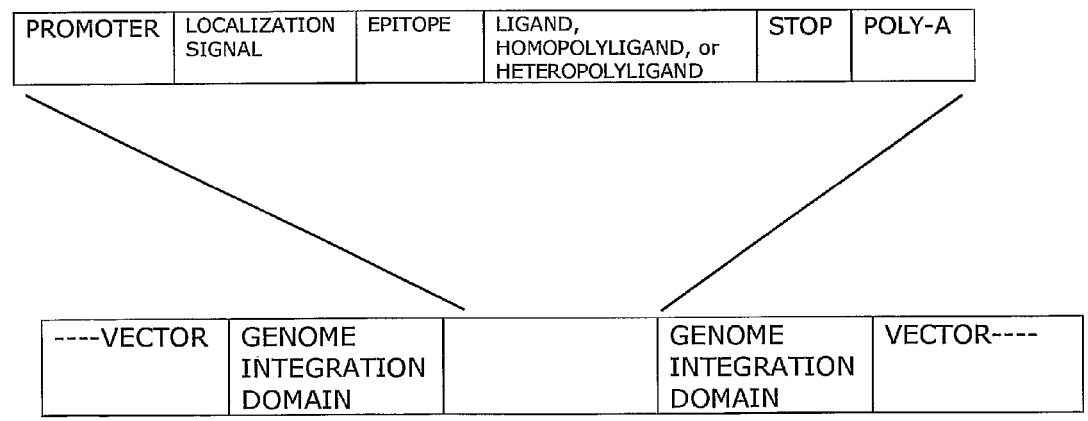
Figure 10C:
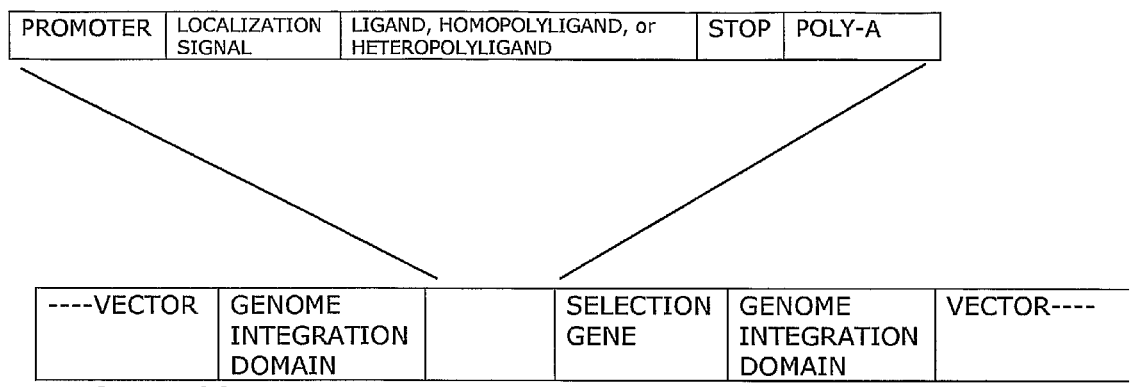

FIG. 10A shows a vector containing a PKD ligand gene construct, wherein the ligand gene construct is releasable from the vector as a unit useful for generating transgenic animals. For example, the ligand gene construct, or transgene, is released from the vector backbone by restriction endonuclease digestion. The released transgene is then injected into pronuclei of fertilized mouse eggs; or the transgene is used to transform embryonic stem cells. The vector containing a ligand gene construct of FIG. 10A is also useful for transient transfection of the trangene, wherein the promoter and codons of the transgene are optimized for the host organism. The vector containing a ligand gene construct of FIG. 10A is also useful for recombinant expression of polypeptides in fermentable organisms adaptable for small or large scale production, wherein the promoter and codons of the transgene are optimized for the fermentation host organism.

Figure 10D:
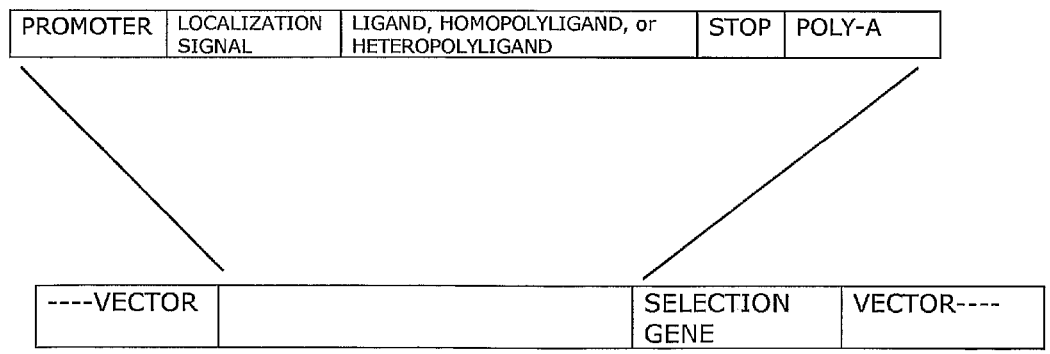

FIG. 10D shows a vector containing a PKD ligand gene construct useful for generating stable cell lines.

The invention also encompasses polynucleotides comprising nucleotide sequences encoding ligands, homopolyligands, and heteropolyligands. The polynucleotides of the invention are optionally linked to additional nucleotide sequences encoding epitopes, reporters and/or localization signals. Further, the nucleic acids of the invention are optionally incorporated into vector polynucleotides. The polynucleotides are optionally flanked by nucleotide sequences comprising restriction endonuclease sites and other nucleotides needed for restriction endonuclese activity. The flanking sequences optionally provide cloning sites within a vector. The restriction sites can include, but are not limited to, any of the commonly used sites in most commercially available cloning vectors. Examples of such sites are those recognized by BamHI, ClaI, EcoRI, EcoRV, SpeI, AflII, NdeI, NheI, XbaI, XhoI, SphI, NaeI, SexAI, HindIII, HpaI, and PstI restriction endonucleases. Sites for cleavage by other restriction enzymes, including homing endonucleases, are also used for this purpose. The polynucleotide flanking sequences also optionally provide directionality of subsequence cloning. It is preferred that 5' and 3' restriction endonuclease sites differ from each other so that double-stranded DNA can be directionally cloned into corresponding complementary sites of a cloning vector.

Ligands and polyligands with or without localization signals, epitopes or reporters are alternatively synthesized by recombinant techniques. Polynucleotide expression constructs are made containing desired components and inserted into an expression vector. The expression vector is then transfected into cells and the polypeptide products are expressed and isolated. Ligands made according to recombinant DNA techniques have utility as research tools and/or therapeutics.

An example of how nucleotide sequences encoding ligands, homopolyligands, and heteropolyligands are produced is as follows. Complimentary oligonucleotides encoding the ligands and flanking sequences are synthesized and annealled. The resulting double-stranded DNA molecule is inserted into a cloning vector using techniques known in the art. When the ligands and polyligands are placed in-frame adjacent to sequences within a transgenic gene construct that is translated into a protein product, they form part of a fusion protein when expressed in cells or transgenic animals.

Another embodiment of the invention relates to selective control of transgene expression in a desired cell or organism. The promotor portion of the recombinant gene can be a constitutive promotor, a non-constitutive promotor, a tissue-specific promotor (constitutive or non-constitutive) or a selectively controlled promotor. Different selectively controlled promotors are controlled by different mechanisms. RheoSwitch$^R$ is an inducible promotor system available from RheoGene. Temperature sensitive promotors can also be used to increase or decrease gene expression. An embodiment of the invention comprises a ligand or polyligand gene construct whose expression is controlled by an inducible promoter.

Polyligands are modular in nature. An aspect of the instant invention is the combinatorial modularity of the disclosed polyligands. Another aspect of the invention are methods of making these modular polyligands easily and conveniently. In this regard, an embodiment of the invention comprises methods of modular subsequence cloning of genetic expression components. When the ligands, homopolyligands, heteropolyligands and optional amino acid expression components are synthesized recombinantly, one can consider each clonable element as a module. For speed and convenience of cloning, it is desirable to make modular elements that are compatible at cohesive ends and are easy to insert and clone sequentially. This is accomplished by exploiting the natural properties of restriction endonuclease site recognition and cleavage. One aspect of the invention encompasses module flanking sequences that, at one end of the module, are utilized for restriction enzyme digestion once, and at the other end, utilized for restriction enzyme digestion as many times as desired. In other words, a restriction site in one part of the module is utilized and destroyed in order to effect sequential cloning of modular elements. An example of restriction sites flanking a coding region of interest are sequences recognized by the restriction enzymes NgoM IV and Cla I; or Xma I and Cla I. Cutting a first circular DNA with NgoM IV and Cla I to yield linear DNA with a 5' NgoM IV overhang and a 3' Cla I overhang; and cutting a second circular DNA with Xma I and Cla I to yield linear DNA with a 5' Cla I overhang and a 3' Xma I overhang generates first and second DNA fragments with compatible cohesive ends. When these first and second DNA fragments are mixed together, annealed, and ligated to form a third circular DNA fragment, the NgoM IV site that was in the first DNA and the Xma I site that was in the second DNA are destroyed in the third circular DNA. Now this vestigial region of DNA is protected from further Xma I or NgoM IV digestion, but flanking sequences remaining in the third circular DNA still contain intact 5' NgoM IV and 3' Cla I and Xma I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences.

Figure 11:
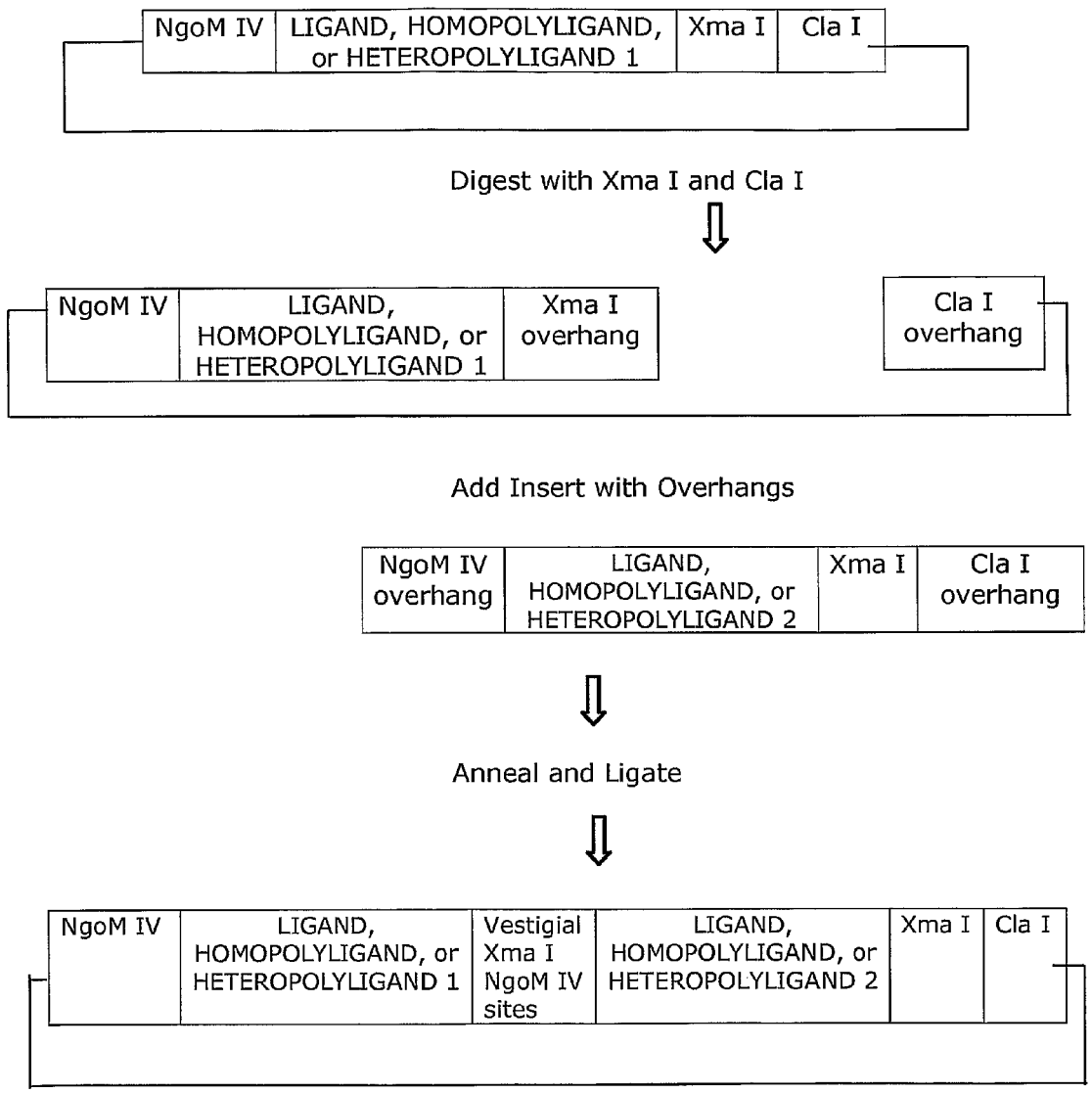
FIG. 11 shows an example of a sequential cloning process useful for combinatorial synthesis of polyligands.

Another way to assemble coding region modules directionally and sequentially employs linear DNA in addition to circular DNA. For example, like the sequential cloning process described above, restriction sites flanking a coding region module are sequences recognized by the restriction enzymes NgoM IV and Cla I; or Xma I and Cla I. Referring to FIG. 11, a first circular DNA is cut with Xma I and Cla I to yield linear DNA with a 5' Cla I overhang and a 3' Xma I overhang. A second linear double-stranded DNA is generated by PCR amplification followed by digestion, or by synthesizing and annealing complimentary oligonucleotides. The second linear DNA has 5' NgoM IV overhang and a 3' Cla I overhang, which are compatible cohesive ends with the first DNA linearized. When these first and second DNA fragments are mixed together, annealed, and ligated to form a third circular DNA fragment, the Xma I site that was in the first DNA and the NgoM IV site that was in the second DNA are destroyed in the third circular DNA. Flanking sequences remaining in the third circular DNA still contain intact 5' N NgoM IV and 3' Cla I and Xma I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences. This process is depicted in FIG. 11.

One of ordinary skill in the art recognizes that other restriction site groups can accomplish sequential, directional cloning as described herein. Preferred criteria for restriction endonuclease selection are selecting a pair of endonucleases that generate compatible cohesive ends but whose sites are destroyed upon ligation with each other. Another criteria is to select a third endouclease site that does not generate sticky ends compatible with either of the first two. When such criteria are utilized as a system for sequential, directional cloning, ligands, polyligands and other coding regions or expression components can be combinatorially assembled as desired. The same sequential process can be utilized for epitope, reporter, and/or localization signals.

Polyligands and methods of making polyligands that modulate PKD activity are disclosed. Therapeutics include delivery of purified ligand or polyligand with or without a localization signal to a cell. Alternatively, ligands and polyligands with or without a localization signals are delivered via adenovirus, lentivirus, adeno-associated virus, or other viral constructs that express protein product in a cell.

EXAMPLE 1

A polypeptide comprising a heteropolyligand, an endoplasmic reticulum cellular localization signal, and a His6 epitope is synthesized. Examples of such polypeptides are generically represented by FIGS. 8B, 8D, 8E and 8F. The polypeptide is synthesized on an automated peptide synthesizer or is recombinantly expressed and purified. Purified polypeptide is solubilized in media and added to cells. The polypeptide is endocytosed by the cells, and transported to the endoplasmic reticulum. Verification is performed by immunohistochemical staining using an anti-His6 antibody.

EXAMPLE 2

A transgene is constructed using a human cytomegalovirus (CMV) promoter to direct expression of a fusion protein comprising SEQ ID NO:113 (POLYLIGAND), green fluorescent protein (REPORTER), and a nuclear localization signal (LOCALIZATION SIGNAL). Such a transgene is generically represented by FIG. 9A-9D. The transgene is transfected into cells for transient expression. Verification of expression and location is performed by visualization of green fluorescent protein (GFP) by confocal microscopy.

EXAMPLE 3

A transgene construct is built to produce a protein product with expression driven by a tissue-specific promoter. The transgene comprises a synthetic gene expression unit engineered to encode three domains. Each of these three domains is synthesized as a pair of complimentary polynucleotides that are annealed in solution, ligated and inserted into a vector. Starting at the amino-terminus, the three domains in the expression unit are nucleotide sequences that encode a PKD ligand, a FLAG™ epitope, and an endoplasmic reticulum localization signal. The PKD ligand is a monomeric ligand, homopolymeric ligand or heteropolymeric ligand as described herein. Nucleotide sequences encoding a FLAG™ epitope are placed downstream of nucleotide sequences encoding the PKD ligand. Finally, nucleotide sequences encoding the localization signal are placed downstream of those encoding the FLAG™ epitope. The assembled gene expression unit is subsequently subcloned into an expression vector, such as that shown in FIG. 10A, and used to transiently transfect cells. Verification is performed by immunohistochemical staining using an anti-FLAG™ antibody.

EXAMPLE 4

Ligand function and localization is demonstrated in vivo by making a transgene construct used to generate mice expressing a ligand fusion protein targeted to the endoplasmic reticulum. The transgene construct is shown generically in FIG. 10B. The expression unit contains nucleotides that encode a tetramer of SEQ ID NO:33, a hemagluttinin epitope, and a mitochondrial localization signal. This expression unit is subsequently subcloned into a pBluscript-based vector (Stratagene; La Jolla, Calif.) between nucleotide sequences including a promoter and an SV40 polyadenylation signal. The completed transgene is then injected into pronuclei of fertilized mouse oocytes. The resultant pups are screened for the presence of the transgene by PCR. Transgenic founder mice are bred with wild-type mice. Heterozygous transgenic animals from at least the third generation are used for the following tests, with their non-transgenic littermates serving as controls.

Test 1: Southern blotting analysis is performed to determine the copy number. Southern blots are hybridized with a radio-labeled probe generated from a fragment of the transgene. The probe detects bands containing DNA from transgenic mice, but does not detect bands containing DNA from non-transgenic mice. Intensities of the transgenic mice bands are measured and compared with the transgene plasmid control bands to estimate copy number. This demonstrates that mice in Example 4 harbor the transgene in their genomes.

Test 2: Tissue homogenates are prepared for Western blot analysis. This experiment demonstrates the transgene is expressed in tissues of transgenic mice because hemagluttinin epitope is detected in transgenic homogenates but not in non-transgenic homogenates.

These examples demonstrate delivery of ligands to a localized region of a cell for therapeutic or experimental purposes. The purified polypeptide ligands can be formulated for oral or parenteral administration, topical administration, or in tablet, capsule, or liquid form, intranasal or inhaled aerosol, subcutaneous, intramuscular, intraperitoneal, or other injection; intravenous instillation; or any other routes of administration. Furthermore, the nucleotide sequences encoding the ligands permit incorporation into a vector designed to deliver and express a gene product in a cell. Such vectors include plasmids, cosmids, artificial chromosomes, and modified viruses. Delivery to eukaryotic cells can be accomplished in vivo or ex vivo. Ex vivo delivery methods include isolation of the intended recipient's cells or donor cells and delivery of the vector to those cells, followed by treatment of the recipient with the cells.

Disclosed are ligands and polyligands that modulate PKD activity and methods of making and using these ligands. The ligands and polyligands are synthesized chemically or recombinantly and are utilized as research tools or as therapeutics. The invention includes linking the ligands and polyligands to cellular localization signals for subcellular therapeutics.

What is claimed is:

1. An isolated polypeptide comprising the amino acid sequence of SEQ ID NO: 105, 109 or 113.

2. The polypeptide of claim 1 linked to a subcellular localization signal.

3. The polypeptide of claim 1 linked to an epitope.

4. The polypeptide of claim 1 linked to a reporter.

5. A composition comprising the polypeptide of claim 1.

6. An isolated polynucleotide comprising a polynucleotide encoding the polypeptide of claim 1.

7. A vector comprising the polynucleotide of claim 6.

8. A recombinant host cell comprising the vector of claim 7.

9. The polynucleotide of claim 6, wherein the polynucleotide is flanked on one end by a sequence cleavable by a first restriction endonuclease, and wherein the polynucleotide is flanked on the other end by a sequence cleavable by a second restriction endonuclease, and wherein the first and second restriction endonucleases generate noncompatible cohesive ends.

10. A method of inhibiting PKD in a cell comprising transfecting the vector of claim 7 into a host cell and culturing the transfected host cell under conditions suitable to produce at least one copy of the polypeptide, thereby inhibiting PKD.

11. The isolated polypeptide of claim 1, wherein the polypeptide comprises the amino acid sequence of SEQ ID NO: 105.

12. The isolated polypeptide of claim 1, wherein the polypeptide comprises the amino acid sequence of SEQ ID NO: 109.

13. The isolated polypeptide of claim 1, wherein the polypeptide comprises the amino acid sequence of SEQ ID NO: 113.

14. The isolated polynucleotide of claim 6, wherein the polynucleotide comprises the polynucleotide of SEQ ID NO: 105.

15. The isolated polynucleotide of claim 6, wherein the polynucleotide comprises the polynucleotide of SEQ ID NO: 109.

16. The isolated polynucleotide of claim 6, wherein the polynucleotide comprises the polynucleotide of SEQ ID NO: 113.

17. The method of claim 10, wherein the vector comprises the polynucleotide of SEQ ID NO: 105.

18. The method of claim 10, wherein the vector comprises the polynucleotide of SEQ ID NO: 109.

19. The method of claim 10, wherein the vector comprises the polynucleotide of SEQ ID NO: 113.

* * * * *